US007560259B2

(12) United States Patent
Weinshilboum et al.

(10) Patent No.: US 7,560,259 B2
(45) Date of Patent: Jul. 14, 2009

(54) GLUTATHIONE S-TRANSFERASE SEQUENCE VARIANTS

(75) Inventors: Richard M. Weinshilboum, Rochester, MN (US); Baidehi Mukherjee, Rochester, MN (US); Linda L Pelleymounter, Rochester, MN (US); Oreste Salavaggione, St. Louis, MO (US); Eric D. Wieben, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/103,444

(22) Filed: Apr. 15, 2008

(65) Prior Publication Data

US 2008/0248549 A1    Oct. 9, 2008

Related U.S. Application Data

(62) Division of application No. 11/482,525, filed on Jul. 7, 2006, now Pat. No. 7,390,894.

(60) Provisional application No. 60/697,128, filed on Jul. 7, 2005.

(51) Int. Cl.
*C12N 9/10* (2006.01)
*C07K 14/00* (2006.01)
*C12P 21/00* (2006.01)
*C12N 15/00* (2006.01)
*C12N 1/21* (2006.01)
*C12N 5/10* (2006.01)
*C12Q 1/48* (2006.01)
*C07H 21/00* (2006.01)

(52) U.S. Cl. .................. 435/193; 435/320.1; 435/69.1; 435/325; 435/352.3; 435/15; 530/350; 536/23.2; 536/23.5

(58) Field of Classification Search ................. 435/193, 435/69.1, 15, 320.1, 325, 252.3; 530/350; 536/23.2, 23.5
See application file for complete search history.

(56) References Cited

U.S. PATENT DOCUMENTS 5,451,683 A    9/1995   Barrett et al.
5,733,729 A    3/1998   Lipshutz et al.
5,770,722 A    6/1998   Lockhart et al.

FOREIGN PATENT DOCUMENTS

WO    WO 9820019      5/1998
WO    WO 99/57318    11/1999

OTHER PUBLICATIONS

Whitbread et al., Pharmacogenetics 13:131-144; 2003.*
GenBank Accession No. NM_183239 dated Nov. 17, 2006.
GenBank Accession No. NT_030059 dated Aug. 29, 2006.
GenBank Accession No. AF389745 dated Aug. 2001.
GenBank Accession No. BP190660 dated Jul. 2003.
GenBank Accession No. AZ909555 dated Mar. 2001.
Adjei et al., "Human estrogen sulfotransferase (SULT1E1) pharmacogenetics: gene resequencing and functional genomics," *Br. J. Pharmacol.*, 2003, 139:1373-1382.
Altshuler et al., "A haplotype map of the human genome," *Nautre*, 2005, 437:1299-1320.
Bardelli et al., "Mutational Analysis of the Tyrosine Kinome in Colorectal Cancers," *Science*, 2003, 300:949.
Board et al., "Identification, Characterization, and Crystal Structure of the Omega Class Gluathione Transferases," *J. Biol. Chem.*, 2000, 275(32):24798-24806.
Branden et al., *Introduction to Protein Structure*, 1991, Garland Publishing Inc., New York, p. 247.
Brodde and Leineweber, "$\beta_2$-Adrenoceptor gene polymorphisms," *Pharmacogenet. Genomics*, 2005, 15:267-275.
Chadwick et al., "Heterozygote and Mutation Detection by Direct Automated Fluorescent DNA Sequencing Using a Mutant *Taq* DNA Polymerase," *BioTechniques*, 1996, 20:676-683.
Chen et al., "Cancer potential in liver, lung, bladder and kidney due to ingested inorganic arsenic in driking water," *Br. J. cancer*, 1992, 66:888-892.
Drysdale et al., "Complex promoter and coding region $\beta_2$-adrenergic receptor haplotypes alter receptor expression and predict in vivo responsivness," *Proc. Natl. Acad. Sci. USA*, 2000, 97(19):10483-10488.
Excoffier and Slatkin, "Maximum-Likelihood Estimation of Molecular Haplotype Frequencies in a Diploid Population," *Mol. Biol. Evol.*, 1995, 12:921-927.
Fullerton et al., "Apolipoprotein E variation at the Sequence Haplotype Level: Implications for the Origin and Maintenance of a Major Human Polymorphism," *Am. J. Hum. Genet.*, 2000, 67:881-900.
Hacia et al., "Detection of heterozygous mutations in *BRCA1* using high density oligonucleotide arrays and two-colour fluorescence analysis," *Nat. Genet.*, 1996, 14:441-447.
Hartl and Clark, "Organization of genetic Variation," *Principles and Population Genetics*, 1997, Chapter 3, Sinauer Associates, Inc., Sunderland, MA, pp. 71-109.
Hayes et al., "Glutathione transferases," *Annu. Rev. Pharmacol. Toxicol.*, 2005, 45:51-88.
Hedrick, "An Introduction fo Gametic Disequilibrium," *Genetics of Populations*, 2000, 2nd edition, Jones and Bartlett (Sudbury, MA), pp. 396-406.
Hopenhayn-Rich et al., "Lung and kidney cancer mortality associated with arsenic in drinking water in Córdoba, Arentina," *Int. J. Epidermiol.*, 1998, 27:561-569.
Ivanov and Hei, "Combined treatment with EGFR inhibitors and srsenite upegulated apoptosis in human EGFR-positive melanomas: a role of supression of the PI3K-AKT pathway," *Oncogene*, 2005, 24:616-626.
Ji et al., "Human phenylethanolamine N-methyltranferase pharmacogenomics: gene resequencing and functional genomics," *J. Neurochem.*, 2005, 95:1766-1776.

(Continued)

*Primary Examiner*—Delia M Ramirez
(74) *Attorney, Agent, or Firm*—Fish & Richardson P.C.

(57) ABSTRACT

Isolated GSTO2 nucleic acid molecules that include a nucleotide sequence variant and nucleotides flanking the sequence variant are described, as well as GSTO2 allozymes. Methods for determining if a subject contains a GSTO2 sequence variant also are described.

2 Claims, 35 Drawing Sheets

OTHER PUBLICATIONS

Landi, "Mammalian class theta GST and differential susceptibility to carcinogens: a review," *Mutat. Res.*, 2000, 463:247-283.
Long et al., "An E-M Algorithm and STesting Strategy for Multiple-Locus Haplotypes," *Am. J. Hum. Genet.*, 1995, 56:799-810.
Maeda et al., "Effective treatment of advanced solid tumors by the combination of arsenic trioxide and L-buthionine-sulfoximine," *Cell Death Differ.*, 2004, 11:737-746.
Maeda et al., "Tumor growth Inhibition by Arsenic Trioxide ($As_2O_3$) in the Orthotopic Metastasis Model of Androgen-independent Prostate Cancer," cancer Res., 2001, 61:5432-5440.
Maiorino and Aposhian, "Dimercaptan Metal-Binding Agents Influence the Biotransformation of Arsenite in the Rabbit," *Toxicol. Appl. Pharmacol.*, 1985, 77:240-250.
Marnell et al., "Polymorphisms in the Human Monomethylarsonic Acid ($MMA^V$) Reductase/hGSTO1 Gene and Changes in Urinary Arsenic Profiles," *Chem. Res. Toxicol.*, 2003, 16:1507-1513.
Martin et al., "Human methylenetetrahydrofolate reductase pharmacogenomics: gene resequencing and functional genomics," *Pharmacogenet. Genomics*, 2006, 16:265-277.
Mathews et al., "Single-agent arsenic trioxide in the treatment of newly diagnosed acute promyelocytic leukemia: durable remissions with minimal toxicity," *Blood*, 2006, 107(7):2627-2632.
Minamoto et al., "Arsenic-Contaminated Water and Extent of Acute Childhood Malnutrition (Wasting) in Rural Bangladesh," *Environ. Sci.*, 2005, 12:283-291.
Mulder and Ouwerkerk-Mahadevan, "Modulation of glutathione conjugation in vivo: how to decrease glutathione conjugation in vivo or in intact cellular systems in vitro, " *Chemico-Biol. Interact.* 1997, 105:17-34.
Nebert and Vasiliou, "Analysis of the glutathione S-transferase (GST) gene family," *Hum. Genom.*, 2004, 1:460-464.
Paul et al., "Skin cancers in chronic arsenic toxicity--a study of predictive value of some proliferative markers," *Indian J. Pathol. Microbiol.*, 2004, 47(2):206-209.
Pool-Zobel et al., "Modulation of xenobiotic metabolising enzymes by anticarcinogens-focus on glutathione S-transferases and their role as targets of dietary chemoprevention in colorectal carcinogenesis," *Mutat. Res.*, 2005, 591:74-92.
Prince et al., "Robust and Accurate Single Nucleotide Polymorphism Genotyping by Dynamic Allele-Specific Hybridization (DASH): Design Criteria and Assay Validation," *genome Res.*, 2001, 11:152-162.
Ratnaike, "Acute and Chronic arsenic toxicity," *Postgrad. Med. J.*, 2003, 79:391-396.
Salavaggione et al., "Thiopurine S-methyltransferase pharmacogenetics: variant allele functional and comparative genomics," *Pharmacogenet. Genomics*, 2005, 15:801-185.
Schafer and Hawkins, "DNA variation and the future of human genetics," *Nat. Biotechnol.*, 1998, 16:33-39.
Schaid et al., "Score Tests for Association between Traits and Haplotypes when Linkage Phase Is Ambiguous," *Am. J. Hum. Genet.*, 2002, 70:425-434.
Schmuck et al., "Characterization of the monomethylarsonate reductase and dehydroascorbate reductase activities of Omega class glutathione transferase variants: implications for arsenic metabolism and the age-at-onset of Alzheimer's and Parkinson's diseases," *Pharmavogenet. Genomics*, 2005, 15:493-501.
Seffernick et al., "Melamine deaminase and atrazine chlorohydrolase: 98 precent identical but functionally ifferent," *J. Bacteriol.*, 2001, 183(8):2405-2410.
Shastry, "Gene disruption in mice: Models of development and dissease," *Mol. Cell. Biochem.*, 1998, 181:163-179.
Soignet et al., "Complete remission after treatment of acute promeylocytic leukemia with arsenic trioxide," *N. Engl. J. Med.*, 1998, 339(19):1341-1348.
Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Strange et al., "Glutathione S-transferase: genetics and role in toxicology," *Toxicol. Lett.*, 2000, 112-113:357-363.
Strange et al., "Glutathione-*S*-transferase family of enzymes," *Mutat. Res.*, 2001, 482:21-26.
Tajima, "Statistical Method for Testing the Neutral Mutation Hypothesis by DNA Polymorphism," *genet.*, 1989, 123:585-595.
Tchounwou et al., "Carcinogenic and Systemic Health Effects Associated with Arsenic Exposure--A Critical Review," *Toxicol. Pathol.*, 2003, 31:575-588.
Tchounwou et al., "Important Considerations in the Development of Public Heath Advisories for Arsenic and Arsenic-Containing Compounds in Drinking Water," *Rev. Environ. Health*, 1999, 14(4):211-229.
Terwilliger and Ott, "Linkage Disequilibrium between Alleles at Marker Loci," *Handbook of Human Genetic Linkage*, 1994, The Johns Hopkins University Press, Baltimore, pp. 188-193.
Thomae et al., "Human catecholoamine sulfotransferase (SULT1A3) pharmacogentics: functional genetic polymorphism," *J. Neurochem.*, 2003, 87:809-819.
Thomae et al., "Human sulfotransferase SULT2A1 pharmacogenetics: genotype-to-phenotype studies," *Pharmacogenomics J.*, 2002, 2:48-56.
Underhill et al., "Detection of Numerous Y Chromosome Biallelic Polymorphisms by Denaturing High-Performance Liquid Chromatography," *Genome Res.*, 1997, 7:996-1005.
Vahter, "Genetic polymorphism in the biotransformation of inorganic arsenic and its role in toxicity," *Toxicol. Lett.*, 2000, 112-113:209-217.
Wang et al., "Human thiopurine S-methyltransferase pharmacogenetics: Variant allozyme misfolding and aggresome formation," *Proc. Nat. Acad. Sci. USA*, 2005, 102(26):9394-9399.
Wang et al., "Thiopurine S-methyltransferase pharmacogenetics: chaperone protein association and allozyme degradation," *Pharmacogenet.*, 2003, 13:555-564.
Weinshilboum and Wang, "Pharmacogenetics: Inherited variation in amino acid sequence and altered protein quantity," *Clin. Pharmacol. Ther.*, 2004, 75:253-258.
Whitebread et al., "Characterization of the human Omega class glutathione transferase genes and associated polymorphisms," *Pharmacogenet.*, 2003, 13:131-144.
Whitebread et al., "Glutathione transferase Omega class polymorphisms in Parkinson disease," *Neurology*, 2004, 62(10:1910-1911.
Witkowski et al., "Conversion of a beta-ketoacyl synthase to a malonyl decarboxylase by replacement of the active-site cysteine with glutamine," *Biochemistry*, 1999, 38:11643-11650.
Wood et al., "Human Arsenic Methyltransferase (AS3MT) Pharmacogenetics. Gene Reseqencing and Functional Genomics Studies," *J. Biol. Chem.*, 2006, 281(11):7364-7373.
Yang et al., "Role of the Glutathione Metabolic Pathyway in Lung Cancer Treatment and Prognosis: A Review," *J. Clin. Oncol.*, 2006, 24(11):1761-1769.
Yu et al., "Genetic Variation in Genes Assocaited with Arsenic Metabolism: Glutathione S-Transferease Omega 1-1 and Purine Nucleoside Phosphorylase Polymorphisms in European and Indigenous American," *Enciron. Health Perspect.*, 2003, 111:1421-1427.
Zakharyan and Aposhian, "Enzymatic Reduction of Arsenic Compounds in Mammalian Systems: The Rate-Limiting Enzyme of Rabbit Liver Arsenic Biotransformation Is $MMA^V$ Reductase," *Chem. Res. Toxicol.*, 1999, 12:1278-1283.
Zakharyan et al., "Enzymatic Methylation of Arsenic Compounds: Assay, Partial Purification, and Properties of Arsenite Methyltransferase and Monomethylarsonic Acid Methyltransferase of Rabbit Liver," *Chem. Res. Toxicol.*, 1995, 8:1029-1038.
Zakharyan et al., "Human Monomethylarsonic Acid ($MMA^V$) Reductase Is a Member of the Glutathione-S-transferase Superfamily," *Chem. Res. Toxicol.*, 14:1051-1057.

* cited by examiner

Figure 1 – page 1

| | | | | | | |
|---|---|---|---|---|---|---|
| 1 | CAGGCATTGA | ACCTGGGGTG | GACGCCTTCG | TCCTCTTACT | TTCGGGAACA | CCCTACTCTG | 60 |
| 61 | TCTATGGAGT | AGCTGTTTTT | TCACCACTTT | ACTTCTTAA | TAAACTTGCT | TTTGTTTTGC | 120 |
| 121 | ACGGTGGACT | CGCTCTGAAT | TCTTTCTTAT | GCGAGATCCA | AGAACCCTCT | CTTGGGTCTG | 180 |
| 181 | GATCAGGACC | CCTTTCCCGT | AACATCTATG | CAGGAGGAAT | AACATGTGTT | CCATCTTATT | 240 |
| 241 | TTACAGGTGA | GGAAACTGAA | ACACACTGAG | GTTAGTGACT | TCCCCATGTT | CACAGTTAAT | 300 |
| 301 | AAGTGGTTGT | TACGGGTTGA | ATTGTGCTCC | CCCAATTTCA | TACATTGATG | TTCTAATCCC | 360 |
| 361 | CAGTGCCCCA | GTATGTGACC | TTATTTGGAA | ATAGGGTTGT | TGCAGATGTA | ACTAAATTAA | 420 |
| 421 | AATGAGGTCA | TACTGGAGTG | TGAATGAAGA | TGAAGGCACA | GATGGGGTGG | GTGGTGCTTC | 480 |
| 481 | TGCACTCCAA | GGGACACCAA | AGATTCCCTC | AAACCACTAG | AAGCTGGGAG | AGAGGCATGG | 540 |
| 541 | AACAGACTCC | CTCACAGACT | CCCTCCTCAG | AAGGCAGCAA | CCCTGCTGAC | ACCTTCATCT | 600 |
| 601 | TGGACTTGTA | GCCTCTAGAA | CTGTGAGGCA | ACACACTTCT | GTTATTTAAG | CCACTCTGCA | 660 |
| 661 | GTACTTTGTT | ACCCTAGTCC | TAGCAACTGA | ATACAGGGGT | GGAGCCAGGA | TCAAAACAGG | 720 |
| 721 | CAGGGTGCTC | CAACACTTGG | TGCTTTTCAC | CTCATTCTCT | GCTCCTCCCA | TAATAGGGCT | 780 |
| 781 | AATCAAAATA | AAAATAGACA | TCTACCCCAA | TCTCACCCCA | ATAAATGGCA | CAGGAGTTAC | 840 |
| 841 | CAGCTTTCAA | ATCTAGGCAA | ACAAGGAAAT | CATTGAATAG | TCTTTTTCCT | CATCTGTATG | 900 |
| 901 | ATGGCCCTGG | AACCCCTCTT | TCCTGACCCC | TAAGTTAAAA | GAGCTGTTTG | AGAGGACTCT | 960 |
| 961 | CTGGCCAGAC | CTTTATTCCC | AGACCCAAAA | CTAAATTCAC | TCATGCCACC | TGCTTGATTC | 1020 |
| 1021 | TGAGCCTGTG | CCCTTATTGT | AACTGAAATG | CAGGTTCAGT | TGCTTCCCGC | TTTCAGAGTC | 1080 |
| 1081 | CAATTATTAA | TAAGAAGAGC | AAAGTCTGGT | ATAAAGAAAG | TGATTTTTA | TTCCAAAGCT | 1140 |
| 1141 | AGCTTAGGGG | GAGCAAAACA | GGCTTCCTGC | CTTAAGGGTA | CCACTTTGCT | TCTGGGGCAG | 1200 |
| 1201 | AAAGCAGGGG | CTTTTAAAGG | GGGCAGTTGG | TATGAACTGC | ATGCTGGGGA | GGGAGCGAGT | 1260 |
| 1261 | GGGTGGGGGT | TCGCATGACT | CACTTTGGTG | CTTTATCTGC | TGGGTTGTGC | CATCATGGGC | 1320 |
| 1321 | AGAAGTCATT | TGTAAAGTGG | CCTTGTCTCA | GGCATACTTT | TGGATGTAAA | TGGACTGTTA | 1380 |
| 1381 | TCTCTGGAGG | CAGTCTCCTG | GGGGTGAGA | GTCCTGCTCT | GGAGCTTTTA | AGTAAACACC | 1440 |
| 1441 | CAGTTAGATA | AGCTTGCCCT | GTAGGGAGTG | TCAGGTGAAG | GGAAGGTAAA | AGATGATAAT | 1500 |
| 1501 | TGCATTTCTA | AAGAGCTAAG | TAGGAAGTGG | GGAACAGGGA | GAAAGGAGGA | AACAGAGAAG | 1560 |
| 1561 | ATGGGAGAAA | TAAATAATGT | AAAAAATAAC | TCATCCTCTA | TCTCTTAGAA | AAATGGGAGT | 1620 |

Figure 1 – page 2

```
1621  ACTGTTATAT TACCAGGGCT CCAAAACACA AATGTTTAAT AAGTGGGAGA GTTTTGAAAG  1680
1681  CAGCACCATT ATTCTGAGGT TGATAATATC CAGGTTTGTG CTGTCTCCTA TGGGTTAAAA  1740
1741  TGAAAAGGAT GTATCCTACA GGTGACGGTA GGGACAGAGG CCCTCCCAGT AGTCACGTTA  1800
1801  AGCTAGTACT GACAGAAAAA GGAAAAGCCT GTCCAGGTGG CTGGGCAACC CTGCAGCGAG  1860
1861  GCATAGATGA GCTTGTAAAT CAAAGGAAAT GACCAAGGTG AGTCTCAATC CTTTTAGAGG  1920
1921  TTTATTTTGC CAAGGTTGAG GACACATCTG AGAAAAAGGA ACACAAAATC ACAGGAACAT  1980
1981  CTGTGATCTG TGCTCTTTCC AAAGAGGGCT TGAGGACTTC AATATTTAAA GGGAAAGAGC  2040
2041  AGGCAGTAGG GGAAAGTGGA AAGTAAAAAG GGAAGGTAGA TAAAAGGGGA GAGTAGTTGC  2100
2101  ATTCTTTGGG GCCTTTGATC AGCATTCACT GAATGCGCAT GTTACATTCG TGAAAGGAGG  2160
2161  TCGTAGAGGA ATAGTCAGTT ATGCATTCGT CTAGTGCTTG GTGAATCTGC ATTTTACAA   2220
2221  GATTAAATAT AGGGTAGAGG AAGCGGTCAA ATTGCATTTT TCTCCAGCGA GAGGAAGGAT  2280
2281  GACTCCTAGA CCTGTCTTTG TCCCATACTT GGGAAGATAA GCTGTTAGTT TACATTGCCA  2340
2341  AGATGAAATT CAACTGATCT GTTTTAGAGT AAAGATCTTG CGGGCCAACA AGGAATTTCC  2400
2401  TTGGGGAGGT GTGTGGCCTT TGATCTTTGT AGCTATTTAG CAACAAAATG GGAGGCAGTG  2460
2461  TTGCCTGACT CAGTTTCCAA GCTTGACTCT TCCCTTTGGC ATAGTGAGTT TGGAGTCAAG  2520
2521  AGATTTTTAT TTTCCCTTCA CAAGCTGAAC AGGAGCCTTT GGAGAGAACG CTCTGGACCG  2580
2581  GTGAGTGAGC CATGAGGTCG GGCCACAGGC TCTGAAGTCG TGAAGCCTTG GGACGGAGCG  2640
2641  GGTGGTGCTT CGAGGTCAGT GTCACGGGAG GGAGGTCAGG GTCAGGGTCA GACGTGGAGC  2700
2701  CCCGTGGAGT GCGGAGTGGT GACCCCTTCG TTCGGGGGCG GAGGGATGAC TGAGCATTTA  2760
2761  TAACTTTTGT GTATCTCCCC GTGGGTGCAG CCCTTGGCCA GCGAGATGCT TTGACACAGC  2820
2821  CCCTTAAGAT GTTTTAAGGG CTATCCCATA AAGCCGGGAA GGCACAACGG GTGGAGCTGG  2880
2881  CGGCCGCCGG GGGCAGGCAC TTTTGAGCTA AGGAGGAAGC GGGGGAGGGA AGGAGGGCGG  2940
2941  GAAGGACGCG CCACCTACTT CCTGAATCCC CTGCAAACCC CAGAGGAGCT CGGCCTGCGC  3000
      GST-Omega 1 Exon 1
3001  TGCGCCACGA TGTCCGGGGA GTCAGCCAGG AGCTTGGGGA AGGGTGAGGC CTGCCCGCCG  3060
3061  CGAAGAGGGG GTGATCTCGG CGACCCCCGG CGGCATGTTC GAGGCTGCTC CGGGAGCCCA  3120
3121  GCCGCCCGGG AGCGCCCCAC CGGCGGGGAA CGGGTCGGAG CTGCAGTGGG ACGCGGGGGC  3180
```

Figure 1 – page 3

```
3181    GGTGGGATAC GGGGGGTCTC GACACCTCTC TGGGCCGTAA TCGCCTTCGC TTCTCCCCGG    3240
         GSTO1 Exon 2
3241    CAGGAAGCGC GCCCCCGGGG CCGGTCCCGG AGGGCTCGAT CCGCATCTAC AGCATGAGGT    3300
3301    TCTGCCCGTT TGCTGAGAGG ACGCGTCTAG TCCTGAAGGC CAAGGGAATC AGGTGGGCAC    3360
3361    CCAGGCGGGG GACGCTCCCC GAGCCGTCCG GGAGCCTGCT GCAGGCGGCG GGGTGGGGTG    3420
3421    GGGTCTCAGC CCCCTTCTAC CCCCCTCCCA CCAGCGTCCT TTACTGCACA TTAAACTATT    3480
3481    CTCGGCCCTT TGGAAAATAG CAAGTTATAG GCCATTCCCC TAGGAAAAAT AGGCCACAGA    3540
3541    TTCCAACGGT CTAGGACACC TCATTTAGAT TAACCAACCA TTTAATGGAT TAGAAAAGCT    3600
3601    GAGGCTCCAG TGATGTTAGT GATTTGCCCG GTAATAACCG GCAGCAGCTC TTTTAGCTTT    3660
3661    GGTAGGTCAC GAATTCCTGG TCCAGAGTCC TTTCGCTTTC GCCCTATTGT GATTTCCCGT    3720
3721    TCTTATTCCA GCTTAACTGT TAGTTGTTAT TCTGAATGTA TTGTTCCCTC CTAGAATAGT    3780
3781    AATTTACCCC AGTACAGCAG AGTTTAGACC CTGACCCTCC TAGGGTAGTG CTGAGTTTAC    3840
3841    TGCACATATT CCTGTGGATT GGGCTGTTGG TTGAGTCAAA TAGAGGGAAG TGTCTGTCTA    3900
3901    GCTCATCCTT CTGCAGAGCC TGTTTTGAAA CTAGCATAGT TTTTGACTTA CGGGCTATCC    3960
3961    ACAGGATATG TGCAACAGTC ACTTGACTTT TCTCTGACAC CAAGTATCCA TTGGAACCAC    4020
4021    TTCCCTTCCC ATGACCTTTG GATGTCTGTT GATTAGACAT TTATTAGATA CCTTTGGTGT    4080
4081    GGAAGGTTCT GTGGAAGTTT AAAACAAACC CCCTATTCTT AAGGAATTTT CTGTCTGTGT    4140
4141    GCTTAGTGTT TGTGAACTAA TTTTAGTCTT CTAAGGGGAT AATCTTTAGG GGTAGGCAAT    4200
4201    TATTTTCCCT AAAAGAAAGG TAAAATGCAT TTAAAAAATA CATTTGAAGG GGATTTGTCA    4260
4261    TTACTTCACT AAGAAATGCA TCTCATTTGG ATGAGATTAT GATTCTGAAC ACATAGAGTA    4320
4321    CTTACTATTT CATAATGTTT CTCAAAAACA CTGTCATATT TGCTGTGATA GAACTCTTTT    4380
4381    ATTGTACTAA GAGAAATCTA ATGTAACCAA AATTGAAAAA AGACATTTTT TGGTACTCAT    4440
4441    TTATTTGAAA AGTCCAGGAG CATGACACAG CTGGATTCAG AGGCACAAAG TCCTGGGTTA    4500
4501    TGTGCTTCAC CCTGGACCTT TAGTTTGAAA ACAACCCTAC CTTATTTACT GGGGCAGTTT    4560
4561    TCCAAAGGAA CATTGAAACT ATCTTCCCCT AATAGTGTGG GGTAGAGGGG AGGAAGAGAG    4620
4621    TGGTTAACAG CTTCCAGACA GTGCAAACAA CAAAGGTCTA CTACATTAAT AGACCAGTTT    4680
4681    TAAGCTTGAG CCCGAGGAGG CTTTTACTGG GAAAGTACTA GATTTTAACC ACATGATATG    4740
```

Figure 1 – page 4

```
4741  ACTTAACAAA GCATGGTTTT CTCTAAAAGA TGCATCTTCC AACTTGCTGT GGCAGGTGTG  4800
4801  TAGACTTGTT GGCTCACAAT GCCAGCTTAC CAAAATTCAT GTGTGTTCTG ACATACTTTT  4860
4861  TTTTTTTTAA ATAACAAAAG CCCAGGATCT TTTTGTTTTC ATAGTAACAA AAGTTTTTGT  4920
4921  TTTATAGTTC AAAAATGTTG ATAATTCTTT GGCAAGGAGC CAAATAATTT TTTTTTTTTT  4980
4981  TGCAATGGCT GGTACTTAAG TGTCCAGTAT TGTCAGCACA TGAACCTTTT AAATTACATG  5040
5041  CACACCTGTG CTCATGTTCA AATTGGATGT TCCTTTGTTT ACATGGGGGA TTATGTATTT  5100
5101  AAATCCTCAA ATGAAATGCT GTTCTAGCTA CAGCTGTGGA TGGGAAAATA GAAAACAAAA  5160
5161  GGTATTGGTG TCTATTTTTT TTTTAGTAAT CTGTTCTATT GAACATTTAT TCAGCCTTGA  5220
5221  CAATCATATG GACCTAGCTC CTTTCTCTTA GTTCCTCTAC AGTCTCAGGC AACATACAAG  5280
5281  ATAGACCTAA ATACAATCTG ACTATAGCCT GGACTTCACC TGTTTCTTC CTTTTGGTT   5340
5341  TACTTTGTAT GATTACTCA GACAACATTT TTTAAAAAAT CAGTACATGG AGATTTAATC  5400
5401  TGAAAGCTTA TTTTGTGGGT GGATTTTTTT TTTTTTTTCG AGACAGGGTC TCGCCCTGTC  5460
5461  ACCCAGGCTG GAATGCAGTG GTGCAATCAT GGCTCACTGC AACCTCTGCC TCCAGGGCTC  5520
5521  AAGCAATCTT CTCACCTCAG CATCCGGAGT AGCCGAGACT ACAGGTGAGT ACCACCACAC  5580
5581  TTGGCTAATT TTTATATTTT TTGTAGAGAT AGGGTTTCAT CATGTTGCCC AGGCTGGTCT  5640
5641  TGAACTCCTG GGTTTAAGCA ATCCGCCCAC TGCAGTCTCC CAAGGTTCTG GGATTACAGA  5700
5701  TGTAAGCTAC CAAGCCTGGC CTTGTGGGTG GATTTAAGG ATTCCTTAAT ATCTTCATAA   5760
5761  AAACCAAGAA ACTTTTTACT CAAATTAGCA AAATAAATTG AATTTTATGT TGGTTCTCAT  5820
5821  ATAGTGGATA GTGGACACAA TTCAATTAGT TGCCTCATAT GATTTATAAC TAAGATACCT  5880
5881  CTTAGCCATA AATGGAGTAT CTTATTGACA ATTTTGAAGC ATTTCCACAG ATTTATTCAT  5940
5941  TCATTTATAT GAAATATTTC AAAACAAAAA TATTTACTGA GTCCTTATTT GAAACTTTTT  6000
6001  ATTTTCTTCA GAGCATTTAT ATCTATATAG CATTTTGCTC ATTTACATGT TTGTTTATTA  6060
6061  CTATGAACAG ATACACAAGA TCCCACCTTT CGTGAAGCTT ACATTCTAGG AAGATAACAA  6120
6121  ACTTGTAAAT AAGTGAGCAA AGTAATTTCA GATACATATT ATCAGTTCAA TGAAGAAAGT  6180
6181  AAAACATGAT AATCATGTAA TAGAAGCTGC TCAGCAACTT CAGAGCTATG GTCAGGGAGG  6240
6241  GCCTGGGGAT GTGTGTTTGA CCTGGGAAGA CCTGGGAAAA GGCAGGCAGA GGAGGCAGAG  6300
6301  GACCATCAAG TGCAAAGACT CTAAGGTGGA AACACATTTG GCAAATTCAA GGAATATAAA  6360
```

Figure 1 – page 5

```
6361    AACCGCCAAC GTGTAAAAGA AAACATAGGG GAAAAGCTTC ATGACACTGG CCTTGGCAAT    6420
6421    GATTTCCTGG ACATGACACC AAAGACCAGG CAACAAGACC AAAAATAAAC ACATGAGACT    6480
6481    ACAGCAAACA AGCTTCCACA CAGCAAAGGA AACGATTAAC AGAGCAAAAA GGCAACCTAT    6540
6541    GGAATAGGAG AAAGTACTTG CAAACCACAT ACCTGGTAAG GGGTTAATCT CCAAAATACA    6600
6601    TAAGGAATCT CTACAACTCA ACAACAAAAA AACCTGATTT AACATGGGC TAAGATCTTA     6660
6661    CATAGACACT TCTCAGGCTG GGCATGGTAG CTCACGCCTA TAACCCCGAG GCAGACAGTT    6720
6721    CACTTGAGCC CAGGAGTTCA AGACCAGCCT TGGCAACATG GCAGAATCCT GTCTCTACAA    6780
6781    AGAAATTAGC TGGGTGTGAT GGTGCACGCC TGTGGTCCCA ACTACTCGGG AGGTAGGAGG    6840
6841    ATCGCTTTAG CCCAGGAGGT CGAGGCTGCA GTGAGCTGCG ATCAAGCCAC TGTACTCCAG    6900
6901    TCTGGGAGAC AGAGTGTCAA AAAAATTAA AAATTAAAAA AATAGACATT TCTTCAAAGA      6960
6961    GGATATAAAA ATGGGCAACA CATATATGAA AAAGTTCTTA TCACTAATCA TCAGGAAAAT    7020
7021    GCAAATCAAA ATCACATAAT AACCTCACAC TTGTCAAGAT GACTATAATG AAAAAAGACA    7080
7081    AGTGTTAGCA AGGATGTGTA GAAATCAGAA CCTTTGCACA CTGTTGGCGG GAATGTAAAA    7140
7141    TGGTACAGCT GCTATGGAAA ACAGTATAGA TGTTCTTCAA AAAATTAAAA CTAGAACTAC    7200
7201    CATGTGATTC AGCAATCTCA CTACTGGGTA TATATCCAAA TTAAATGAAA TCAAGTTCTC    7260
7261    AAAGAGATAT TAGCACTCTC ACGTAGACTG CAGCACTGTT CACAACAGCA TAATGTCAAT    7320
7321    GTCCATCAGC AGATGAATGG ATAAAGAAAA TGTGTTAATG CTATTCCACC TAAAAAGGAA    7380
7381    GGAAATTCTG CAATATGTGA CAACATGGAT GGACATTGCG GACATTATGC TAAGTAAAAT    7440
7441    AAGCCAGACA CAGAAAGACA AATACTGCAT GATTGTTCTT AAAAGGTGTA TCAAAAGTAG    7500
7501    TCAGATTCAT AAAATCAAAA ACTAGAATGG AAGGAATCTA GGCAGACTCC TAAATTTGGG    7560
7561    GTCTGATCAG CTAAGTGGAT GGCAAAGCCA GTGAGAATTT ATCCAAAAGC ACAAAAGTTG    7620
                                                       GSTO1 Exon 3
7621    TTTCCTTCTC TTCATAGTCT CCTATGTGTC TTTCAGGCAT GAAGTCATCA ATATCAACCT    7680
7681    GAAAAATAAG CCTGAGTGGT TCTTTAAGAA AAATCCCTTT GGTCTGGTGC CAGTTCTGGA    7740
7741    AAACAGTCAG GGTCAGCTGA TCTACGAGTC TGCCATCACC TGTGAGTACC TGGATGAAGC    7800
7801    ATACCCAGGG AAGAAGCTGT TGCCGGATGA CCCCTATGAG AAAGCTTGCC AGAAGATGAT    7860
7861    CTTAGAGTTG TTTTCTAAGG TTTGTGCATA AGAAATTTCA GCTCCTATTT GAAAACCTG     7920
```

Figure 1 – page 6

```
7921   TTTTTTAAAG CGAAATCAGT GCTGCCATTT ATGGTTCAGT GATTTGGGAG AGAAAAACAA   7980
7981   AACAGGAATA TGCTTGTCAG CTCTGAGTGT CCTGCAAGTC CTTTCACGAT CCAGTTCCTG   8040
8041   TTTACCTCCA AAATTATCCC TTTTCACTCG TCTCCTGACA CTTTATATAT GCCAGCCATA   8100
8101   CTAAACTTTT CTCAGAATTC CCAAATTCGC CCCTTTCTCT TTCAATTCTT GCTGTCAGAT   8160
8161   TCTTCCCACT TCTCACTGTG CCTGGTTATC TCCACGTCAT TTTTCACATG TCTGCTCCGA   8220
8221   CACTGCTGCC TTTTCAGGAG CTTGGCAGGC TGGTTAGTGC TCTAGCTTCT GAGTTCCCAT   8280
8281   CCGTGTGAAC TTTTGCCTGC CTTCTTGCCT GTGTACTGCA CTGGGGCTGT GAGCTCCTTG   8340
8341   AGGGTGAGGG CTGTGTTTTG ATCACTGTTA GTTCACTGCC TAGTTTTATG ACTGGCTCTG   8400
8401   CTACTTTCTT GTGACTCTGA GCAAGTTACT TATTACTTTG CCTCTCCGTT CATCATTGGT   8460
8461   AAAATGGATA TAGTAATTGT TCCCACCTCA TAAGATAAAA ATCAGTTAAT ATAAAACACC   8520
8521   CAGAACAGAG TCTGACACAT GGGAACTACT TAATTCTTGT CCTTATAGCC ATAGCATCAA   8580
8581   GCAGTGAGCA TCTACTTTGT GTTGGCAATA ACTCAGATGA CTGAATAAAT AGCAATCCTG   8640
8641   TAGAAGAACT GTTTGTACCT TACTTAGCAT CAACACTGTG GATTAGTTCA AACAATTAGT   8700
8701   ATTAACAAAG AAATGACTAA AAGATGTGTG TTTAGACACC AAGAATAGCA TGTCTGGTTA   8760
8761   TATGCCTATA ACATTGTCAC CTTGGTAGTA CGGTCAGTAT ATAAAGGATT ATCTTTAGAG   8820
8821   AAAAAGATGG TTAAAGAAAT GCCCTAAGAG AGAGTTATAG GGAAAACATT CTGTTTTAGG   8880
8881   AGACATTATA AAGGGAAGCC AATGGGACAG GAAGAGTGAG TCATCTGCTT AGTAAGATGA   8940
8941   GGGTGAAAGA ATAGTAGAGG CGGCTGCTGT GAAAGATAAT GTAAAGGGAA CATGACATTT   9000
9001   TCAAGAACGA TGTGGGAGAG TTTTACAAAG TAGTAACAAG TTAAAGGCAT GCAGCTTCAA   9060
9061   GACACGAAGT CATCAATACC AACCAAAAAA AATAAGCCTA AGTGGTTCTT AAAGAAAAAT   9120
9121   CTCTTTGGTC TGGTGCCAGT TCTGGAAAAC TTTTTTTAGT ATGGCTGGAA TATAAAGTGT   9180
9181   CAGGAGAAGA GATAAAAGGG GTAACTTTGG AGAGGTAAAC AGGAACTGGA TCGTGAAAGG   9240
9241   ACTTGTAGGA CACGTCAGAG AAAATGAGCT TTAAAAGTAA AGCTTTTAGA CATGAAGCTT   9300
9301   TACTTTCATG CATAAAGCTA CTACTTTAAA AAGTAGTCAC AAGAGATTCA TTGTACTATC   9360
9361   TAGAAAGAAA ATGAGATTTA AAAGTAATGC TGAAGATGCC CACCTTTACT TCCCTGCTTG   9420
9421   GGTTTTAAAG GAGAGGTGGC TTTATGTACA TATGACCCTG CTCTCCTGGC CACAGCCCAT   9480
9481   CAGAACAGAA ATGTACCCCA CCCCACACAC CTGGGCCAGT TATCTTCTCT CCTGGGAACT   9540
```

Figure 1 – page 7

```
9541   TGGAAATGAG ACACAGAACT AAGACAGTAA AGGTTAGGAC AGTAAAGACA ACTAAGCGTT   9600
9601   GGGGCTCAAA TAATGTTAAT TAGAGGCTAG AAAAACCAAA GCCACTTAAG AAATAAATTT   9660
9661   TTAGAGGAGC AAGAATTAAA AACATTGCAA AGGGACTGAA GTATGCAAAG TAATATGGAG   9720
9721   CAGAAATGTG AGGAAAACA  GACGAAAGAC CAGGCAGACC CAGGTGGAAA TGTGGATGAA    9780
9781   AGGGCTGCCT GAAAGCCTTC AGTCCCAGTG AAGGCAGGCT GAACTGATGT GGATGGGATT   9840
9841   TCATGGGATT CTATATTTTT ACAAGTGCCT GTTTACTTAA ACTAGGATGA GTGGACTTCT   9900
9901   GCGTCTTGCA ATAAAATGAT ACCAAAGACC AAAGTATTAA AACACATAAA CACCATCACG   9960
9961   AGCATTAAAG CATCTGATGC TACACCCATC AAGTCTTTAG GTAGTCGGTC CCTTTTGAAC  10020
10021  AGTCTCCTGG TGTCCTCCCC AACAAAGAAA TCAGAAAAAT TTTCTTCCCT AGCTCTTTGC  10080
10081  AGTTGGGGCC AAGTTTTGTG ACCTAGGCTC TTCCTGTCAG ACACACACAT AGAGTTCAAA  10140
10141  TCAGAAACGA GCAAGGTAAG GAAACAGGCT TGGTGGGATA TCTGCTTAAG ATATTCAGCT  10200
10201  CTCCACTGGT TTTCCTGGTG AGAGCAGCGG CAGAGCTTCT GGGTTTCAGC AGTGTGGGTT  10260
10261  ACAAGATAAA ATTCCAGAGT AGAAATGGCA TCAGTGCCAG TGGTGTTAGC AGTTATCTCA  10320
10321  GACTCTACTT TCTGGCAGCC TCACAAACTG AAGCATCTGG TGCTCAGCTT GGACTGGCAG  10380
10381  CAGTGAGTGC TTCCCATTAG GCCATTTCTC AGCATGAATT TGGGATGTTC TGTCTTAATT  10440
10441  CCAAGCCTGT TTGTTCCGCC TCCCAATAAT CTATGAGCC  ACTCAGTCTC CTTTAAAGAA  10500
10501  AGTTGTGTTG GCCGGGCGTG GTGGCTCAAG CCTGTAATCC CAGCACTTTG GGAGGCTGAG  10560
10561  GCAGATGGAT CACCTGAGGT CAGGAGTTTT CAGACCAGCC TGGCCAATAT GGTGAATCCC  10620
10621  CATCTCTACT AAAAATACAA AAATTAGCCT GGCGTGGTGG CGCACGCCCA TAATCTCAGC  10680
10681  TACTAAGGAG GCGGAGACAG GAGAATTGCT TGAGCCCGGG CAGTGGAGGT TGCAGTGAGC  10740
10741  TGAGATCGTG CCACTGCATT CCAGCCTGGG TGATAGAGCA TGACTCCATT TCAAAAAAGA  10800
10801  AAGAAAGTTG TTTCTTAAAC GTGCCAGGGT AGCTTCTGTT ATTTGTAATT TATAAAATCC  10860
10861  TGACCAAGCC AGCATTTTAG GCCACAAAAC TGTTCCTAAG ACCAGTCCAT TACCTCTGTG  10920
10921  AGCGCAGGAA CTTGATGCAC CCTTGGTGTT TCTAGAACAC CTTGACACCA GGACTGTAAG  10980
10981  GGTTCTACCA TATTTTTATG TGAGGGGGCC GATACAGTTA GCCATAAACT GATAAACTAA  11040
                                     GSTO1 Exon 4
11041  GAAATTATTC TCTGTCTAGG TGCCATCCTT GGTAGGAAGC TTTATTAGAA GCCAAAATAA  11100
```

Figure 1 – page 8

```
11101  AGAAGACTAT GCTGGCCTAA AAGAAGAATT TCGTAAAGAA TTTACCAAGC TAGAGGAGGT  11160
11161  AATTATTTCT CCTAGCTATC ATCAGAGTAA ACGATAACTA TATCTACCCT CCTTTTCCTC  11220
11221  CTATTCTTTT CTTTATATTC CCACTTTCCA AGTCACTTTA AGGTAATTAG GAAAATTCCC  11280
11281  CTAAACATTT TTGTTTACAG CAGACTGCTG TTATAAAGCA GAAAGCTGTC CTGCTTAAGA  11340
11341  TATAAATCAA AACACCTAAA CAGACTTTGT CATGGGCTTG CTTTTAAAAT ATTCTGCTAA  11400
11401  TGTTAAAATA ACAAGGAAAA AGGAAATTGT ACCCACGTTT CCACAAGTTT TTATGTATCC  11460
11461  AGTTTTCCAT GCTTGTTTGC AGTCCTTGTC CATATATTTA AAAAAAATTA ATATAGCTCT  11520
11521  AATCAGAGCA TAGATATCAT TCTGTGTCCT GCTTTTTTTC CTGTGTCCAC TTAGTATTAC  11580
11581  ATACTAAATA TTTCCCACCA GAAAAAGTTT GCAATGAACA GTACAGACAC TTGAGGGAAG  11640
11641  CCCAGATGTA TTTTACCTTC TTTTGGGGAC AGCTGACATT TGGGCCTTGG AGTCTGTCTC  11700
11701  TTGGCCTTGA AATATTTCAT TCATGCTAAG CCTGAAGTTT TTACTGACAG AAGACATAGT  11760
11761  TCCTGTCTTT CATGGGAATG CATTTTAACA TTTTATCAGT AAGCATGATG TTTGCTGTAG  11820
11821  GTTTTTCAGA AACCTTTTTT TCATTATAAA GTTCTCTTCT ATTACTAGTT TGCTAATTTT  11880
11881  TAAAAAAGTC ATAAATGTTG AATTTTATTG AATGGTTTTT CTGCATCTGT TACATCTATT  11940
11941  GAAATGTTCA TAGAATTTTT TCCTCTTAAT CTGGTGAATA TGGTGCTATT GACAAATTTT  12000
12001  TTTTTTTTTA ATGTTTAACC ATCCTAGCAT TCCTAAGATA AAACCTACTT GTTCTCTATG  12060
12061  GATTTTTATA TGTACTGTAG AATTAGCTAA TGAATGATTT TTGTATGTGT GTTCATAAAT  12120
12121  GAGATTGGCC TATAAATTTT CTACTCTTAT AGTATCATTA TTGGCTTTTG GTTTCAAGGA  12180
12181  TATTCTGACC TCATAAAATG AGTTGGGTAA CTAACCTGTT TTTCTAATCT CTGAAACCAT  12240
12241  TTGGTAGGGA CTAGCGGTTT CTTTAAAACA TTTGAGCCTG GTGTCTTTAA CAGGGGTAGA  12300
12301  TTTTTCATTA CTAGTTTGAT TTCTTTAATG GTAATTGGTT TTTTGGTTTT ATATTTCTTC  12360
12361  TTGAATCAGT GTTGGTACTT TTATATTTTT CTGCTGAACA GTGTGGGAGC TGGAAAGTAA  12420
12421  GATGCAGTCC ATATTCTTCA GATAATTAGT TTAGTAGTAG ACAGAACACA GTAGGTAGAT  12480
12481  ATAAGCAATC TAAATGCAT ATTATGCATT GAAAAAAAC TATGGAGGTT ATTTATAAAG  12540
12541  GGCAAATTAG TTTGGTGGTT TAAATAGCCA GATAATATTC TCAATCACCC CCTTTGGCAA  12600
12601  ACCCTGTAAC CAATTCGCCT TCTTAAAATT TCAGAAACAT ACAATTTGTG TTTTGTTTTC  12660
12661  AAATGATTGT CATCTGTTTA GCAGTTAATC CAGTCTATTT CCAGTATATT TTAAGTACAA  12720
```

Figure 1 – page 9

```
12721  ATGCTTTTGC ACTTACAATG GGGTTACATC CAATAAACCC ACCGTAAGCT GAAAATATCA  12780
12781  TAAGTGGAAA ATGCATTTAA TAAACCCAAC CTACAGAGCA TCATAGCTTA GCCTAGCCTG  12840
12841  CTTTAAATGT GCTCAGAAAA CTTCCATTAG CCTGCAATTA GGCAAAATCA TCAAACATAA  12900
12901  AACCATCAAA CATAAAATAT TTATAAAGTG TTGAATATCT CATATAATTT ATCGAATACC  12960
12961  TGCATCCAAA AGATGCTGGC AACACAGCAC ACTTTAGAGC ATTGGTTGTT TACTCTCTTG  13020
13021  ATGGTATGGC TGCCCAGCAT CAAGAGTTAT CATACTGCAA ATCGATAGCC CAGGAAAAGA  13080
13081  GCAAAATTCA AAGTTCAAAG TAGAGTTTTT ACTGAATGCT TGCTTTTGCA CCGTCGTAAA  13140
13141  GTTGAAAAGA ATTTAAATTG AACCATCATA AGCTGCAGAC TGTGCATTTT ATATTGAAAA  13200
13201  GTTAATATTT TTAATTTTTA ATGCAGAGAA GTACCCAAAG CATAAAAACA CAACACGTTT  13260
13261  TCACAAAGCG AACACAGCCA TGGAACCAGC ACCCATATCA ACTAACAAAA TACTAGTTTG  13320
13321  GGCTTTTTTG TACTTTATAC AAATGGACTC ATATAATGTT CATCTTTTGG GTCTGCCTGC  13380
13381  TTTCATTCAA TATTAGGTTT GTGGGTTCAT CTCTGCTGTG TGTAGTTCTT TCCTGTTCTT  13440
13441  TATACAGTGT TCCAAAGTAT AGTATATTAC ACTTTACCCA TTCTACTCTT GATAGTAAAC  13500
13501  GTTTTCACAT TTGGGCTATT ACAAATAGTG CTGCAGTGAA CATTCACATA ACATATCTTT  13560
13561  TGGTGAACAT GTGTTACATT GCCAAGTACA ATTGCTGGGT GATGAGTATG CATACTCTTA  13620
13621  AAACATGGTT GTACCAATTT ACACCTCTAC GACAGTGGTT CCATACCCTT GCCAACTTCA  13680
13681  TTTTGTTCAT TGTAGGCATT CTCTTGGGTG TATAGTGTTA TTGCATTTTG GTTTTAATTT  13740
13741  GCATTTCCCT AATGACTAAT GCAGTTGAAC ACCTTTCCAA ATGATAATTG GCCATTTGGA  13800
13801  CATCATCTTT CTTGAAGATC AAGTCTTGCT CATTTTTCCA ATGGGTCGTT TGCTATTTTT  13860
13861  CTTACTGATT CCCAGGAATC CTTTCTATAT TCTGAATACC AGTCCTTTGT ATTACAAATA  13920
13921  TGTTGTACTC TGTGACTTGT TTTATTTTTC AATTTTCCAG TTTATGTTGT TGATTGTTTT  13980
13981  ACTTCATCCC AGACCAACAG ATTCTAAAGC TTAATTAAGC TTTTTGATCA GAAAAAAACC  14040
14041  CAACTTGGAT ACATCGGAGT AAAAACTGCT TCTCTCACCT GCTCTACTTA TTTCCCTTCA  14100
14101  GCATTTCTAG TGAGTCTTAC TACATGCACA AGTAAGAAAT ACTTTTATGC TGTTTAATGT  14160
              GSTO1 Exon 5
14161  TCAGGTTCTG ACTAATAAGA AGACGACCTT CTTTGGTGGC AATTCTATCT CTATGATTGA  14220
14221  TTACCTCATC TGGCCCTGGT TTGAACGGCT GGAAGCAATG AAGTTAAATG AGTAAGATAT  14280
```

Figure 1 – page 10

```
14281  TTGAATATTT TGTGCATAAT TTAGGATGAC AGGTGGAATA GTATATATTG ACCTTTCTTT  14340
14341  ATAACAGAAG TTGAAATATT TAATACAACT GGTCTGAATG AGAACAAGCA GACAGGGGAA  14400
14401  TCTTGGACTA TCCCAGGCAT GTCATATACC TACACTAACT ACTCTCCATC ACTGCAATGG  14460
14461  GGCAGGGGAT TTCTGAGACA TGTAGTAAAG TGCTTTAAAA TTTATTCCTT CCTTCCTGAT  14520
14521  TAAAAACCCA TAAGGGGAAG GATATGGTAG CTTACGCCTG TAAGCCCAGC ACTTCGGGAG  14580
14581  GCCGAGACGG GTGGATCATC TGAGGTCAGG AGTTAGAGAC CAGCCTGGCC AATGTGGTGA  14640
14641  AACCCCATCT CTACTAAAAA TACAAAAATT AGCTGGGCAT GGTGGTACAC ACCTGTAATC  14700
14701  TCAGCTACTC GGGAGGCTGA GGCAGGAGAA TCACTTGAAC CCGGGAGGCA GTTGCAGTGA  14760
14761  GCTGAGATCA TGTCACTGAA CTCCAGCCTG GGCAAGAGCA AGACACTTCA TCAAAAAAAA  14820
14821  AAAAAAAATT CCATAAGGTT GTAAATTTTT GTAAGGATGT TGTTGCGGGA TTGTACGACC  14880
14881  AGTGTTACCT CCCATTTACC GTAAGATTTC CACATTATTT TCCAAATTCT GTTTTGAGTT  14940
14941  TGGCAGCCAC CTTGCCTTAC TCCGGCTTCT TGGACGATAG AGCTATTCAG GGTTACTTTT  15000
15001  GGTCATAATC TGGGTGTAGA ATAATTAACA TAGAACATTC CTGATTGTAT TCCCTGTTCT  15060
15061  TATTTTAATA AATTGTCAGT TTCTCTCTTT GGGCAAGTTC TCACATTAAC TGAACAAATT  15120
15121  GCTTCACTCT AGTCTCATTC CTTTTGTGTA AAAAGGGAC CTCTATAGTG TCTTTCAAAT  15180
15181  TGAATATTCT ATTACAGGCA TTTTTAAATA TTTTTAATGA ATATTTAAG GGAAAAAAGT  15240
15241  GAAACTGTAG AGTAATAATT ACATATGGGA GACTCTGTGA TGTCATCCTA GTTGACCTAG  15300
                                                       GSTO1 Exon 6
15301  CTCACACCTT TCATTTTTTC CTCTTCCCAC AGGTGTGTAG ACCACACTCC AAAACTGAAA  15360
15361  CTGTGGATGG CAGCCATGAA GGAAGATCCC ACAGTCTCAG CCCTGCTTAC TAGTGAGAAA  15420
15421  GACTGGCAAG GTTTCCTAGA GCTCTACTTA CAGAACAGCC CTGAGGCCTG TGACTATGGG  15480
                 [3'UTR of GSTO1 F(730)]
15481  CTCTGAAGGG GGCAGGAGTC AGCAATAAAG CTATGTCTGA TATTTTCCTT CACTAATATG  15540
15541  AATAATAGCA TGCTTTTATT TTACCAAGGT TCAGGTTGCA TGGGATCATC TTCTCTGACT  15600
15601  GATTTGACAT CAACAGCCAA ACGGTGGGGG TCTCCTTAAC GCCCCCTAC AGAAATGAAA  15660
15661  ATGCATTTCC TGTCTCAGGA TGCTGAAACG ACTCTGAGGG TTCTATCATA GTCCATGCTG  15720
15721  AAAACCCCCA AATTATCATC TTTAGCAAAA TCTGGACTTG AATCTTTTTT TTTTTTTGA  15780
15781  GACGGAGTTT CACTCTTGTT GACCAGGCTG GAGTGCAATG GCCTGATCTC AGCTCACCGC  15840
```

Figure 1 – page 11

```
15841  AACCTCCGCC TCCTGAGTTC AAGCGATTCT CCTGCCTCAG CCTCCTGAGT AGCTGGGATT  15900
15901  ACAGGCATGC GTCACCACGC CTGGCTAATT TTTTTGTATT ATCAGTAGAG AAGGGGTTTC  15960
15961  TCCATGTTGG TCAGGCTGGT CTCCAACTCC CGACCTCAGG TGATCGGCGC GCCTCGGCCT  16020
16021  CCCAAAGTGG CATGAGCCAC CGTACCCGTC CACAATCTAA CTTTATAACT GCTCACAGGA  16080
                                                      [5'FR F(-1462)]
16081  AATACCCACT CAGTTACCCT GTTGTGTGAT TTCATGAGAT GCTCTCTTGT TGCTTGTCTT  16140
16141  CTGGTTTCTT AGTTGAGAAG CTTTCAATTC CTCCTTCTTT CATTTCCATC ATCAACTTAA  16200
                          [5'FR R(-1348)]
16201  TTTCACATTC TCTCTATTGT TGGCCCTGAA GACCAGACGC ACATTACCCG AAAGCTGGGT  16260
16261  GGCTGGGCAG ACTCCTATTT GGTCTCCCTG TCTCTAACCC CTTCAAATCC TTCCTATCAA  16320
16321  ATCCCATGTT GGGCACATAG GTGGTGTCCC ATTTATGTAA TTAAATACTG TGTAGGCTGC  16380
16381  ATCAGTCAAT TCTGCCTACA AGGTTGATGA GTAATAGGTA AGAGCCCCAC TGAGAAATAG  16440
16441  AAATGCCATC TTCCACACAT TTCCATAGCC CACTGCGTTG CTCACTATTC AATTTTTATT  16500
16501  ATCACATCAC CACCACGAGA AGGTAGGTCG GAGAGCAATC ATTTCATTCT ATAGATGATG  16560
16561  CAACTAAGGT CCCGAGGTTA AGTGAGGCCT TAAGGTGCTG GCAGAAAGAT CACACCCAGC  16620
16621  GCACTGCTCT TACCATTGGA ATCAGGGCTG TCGGTCCGCT CCAATTGTCT GGTTTCCTGA  16680
                    [5'FR F(-888)]
16681  ACTTATTTTC AAGTTCGCCA TTGAGAGAAA CCTCCGAATG ACTAATTCTT AAATTTAAGG  16740
                                                   [5'FR R (-791)]
16741  GTGCATAATA ATCACCTATG GCTCACCGCT GCATTTCCGA TTCAGCAGGC TGGGGTGGGT  16800
16801  AGCGAAGTCT GTATTTCAAA TGAGCCCCTC AACCCAGGTG ACGCAGGCGG TGTGGGGACC  16860
16861  GCATCCGGAG GGCGACCTGG AGCCGACTGA CTTCACAAAG GCCTCCTGCC GCAAACCTTC  16920
                                           GST-Omega 2   [Exon 1]
16921  AGCGGCCACC AAAGCCCCGG CTGCCGCCGG CGGACCACCT CTGCTGCCGC GCGCCTACCG  16980
16981  GAGCCGCTTG GCCCTAGTGC TTTCCAGCGG ATTTCCCCTC AGGTGCGGAG CCGGGTGCCG  17040
17041  GGGTCCCACA GCCAACCACT ACCGGTTCCT CTTTCGTCAG CCACCGGCGC CGGCAGGACC  17100
17101  CGCGAATCCC GATCTCCAGG AGCCTGTAAG GAGGCCGCCC ATTGGCTCAG CCGCACTGCT  17160
                                                             [5'UTR F(-368)]
17161  GGGCAGGTAC TTCCAAAGCT TGAGGATTG GCTGATGCTC TGGGCGCCGG GGCTAGTTGG  17220
17221  CGGGTAGGAT CACGTGCGAG GGGCAGGCCC CGTCTAGGCC CCGCCTCCTT GCTGCTGCTG  17280
```

Figure 1 – page 12

```
17281  CCGCCGCAA TCCTGGTCCG GTTGCCCGAG TTCCCGGAGG TCTCTCGCGG GACCTCTCTC  17340
                                              [I1R48]
17341  ACCGCCACCG GTGGGTCCGT TCGGCCTGCG TTGTATTGGA AGGGAAGAGG GGTTTGAGGT  17400
17401  CAATTCTGTT TCCTGGGGTT TTCACGAATT TCGGGCCCA CAGTAGGCTT GCCAACTTTA  17460
17461  ACTTTTGCCT AACACTTTAC GAGAAATCCT ATTTAGCCTT GGCCACTGTT GCATCAAAGA  17520
17521  ATTTCACATC CAACAAAGTG CAGCCTAAGA ATAAGAACA GGTCTTTAAA CCGCATACCT  17580
17581  TTAATTAAGG TGTTCTTATT TTTTCTGATT TGGCTGGAAA CAGGCAGAGA CCACCCCAGA  17640
17641  TAACCAGTTC TCAGCCTTGC GTGGGACACC ACGAGTCCCA CGTGTTTACG TGTTTAAGGC  17700
17701  ACTGGCAAGC AGGGGAATTT GGTTTCTGGG AATGTGCTGT CTTTGTGAAA ACTGTGAAAA  17760
17761  GTCTTCCCTG CTACATTGAA ATAATCATAA AATAATAATA GCTAATGTTG AACACTTACT  17820
                                                         [I1R539]
17821  ATGTATCAGA CACATGCTAA GCATTCAATA TTTCTCATCC AGTTTCTGAA TGAAACCTTC  17880
17881  GCAAACCACA TAATGTACTG GTACTATTAG CTACGAATTA CATATAAGAA CACCCGAAAG  17940
17941  TTGTTGTCAT TTGCCCAAGG TCACCCAGCT AATAAATATT GAAGAGATTC GAATCTAGCC  18000
18001  TGAACTCTTA CAGTAAGACC GTTCGTGAGA TGAATTTATA TGTGCTATTT TTCCAGTCTC  18060
18061  TTTATCCAAC AGCTCTGACA GAGGATAGTA TCTACCTTTT TTTTTTTTT TTGAGACGGA  18120
18121  GTCTCGCTGT TCTGCCCAGG CCGGACTGCA GTGGCGCGAT CTCGGCTCAC TGCAAGCTCC  18180
18181  GCCTCCCGGG TTCACGCCAT TCTCCTGCCT CAGCCTCCCA AGTAGCTGGG ACTACAGGCG  18240
18241  CCCGCCACCG CGCCCGGCTA ATTTTTTGTA TTTTTAGTAG AGACGGGGTT TCACCGTGTT  18300
18301  AGCCAGGATG GTCTCGATCT CTTGACCTCG TGATCCGCCC GCCTCAGCCT CCCAAATCGC  18360
18361  TGGGATTACA GGCGTGAGCC ACCGCGCCCG GCCTGTATCT GCCTTTTTGA CCACACCATT  18420
18421  ATTCGTGGGA TTTAACAGGA GTTAATGAGT TAATAATGTT CCTTTTCCAA ACTCAGTGGT  18480
18481  TTTGATTTTA CAAATTATTT GACTTTTCCT GATTTCAGGA TCTTGACAAT TTGCCTTTAC  18540
18541  TTATTCAAAT GTTATTATAC CAAATATTTA TTTAAAAAGT TTTTTTTTC TTTGATTCCT  18600
18601  CAAGTTGTAG AGAGAAATAG GGATAGGGAA GCAGAATCAA GTAGTTAAAA AGATAGCCTC  18660
18661  ATTTGACCCT GATTTCCCAA TTGGGAATAT GAAATTTTTC CTGAATATAA GCACATTTGA  18720
18721  GAATAGAACC TTTTACCTAA CGTATCTCAC TTTTTGAACT CATTGGACAA TAAGGGAACA  18780
18781  CCCAGTAATA TAATCTTTCA TATAAATTAG GCTTCTAACT TATTAAGAGG AATGTACTCC  18840
```

Figure 1 – page 13

```
18841  AGTCCAGTTT CTGCTACTAT CAAGAGATGG CGTGACAAAA AATTTTGAAA AGTTGCCGAA  18900
                                                                 [I1F(1608)]
18901  TGCAAACCAC AGTTCCTCTT CTCAAAACAA ATGCATGTAA ATAGAGTGTA AGCTATTTCT  18960
18961  TTGGTGGCAT TATTTTCCTA GAAGGCTTAA GTCGTTAATC ACCCATGACC GAAGATCCAA  19020
19021  ACATTTTCAA AGCAGATCCG ATCATATTTC AGGTGGCTGA AAATGGATTT GGAGTAGGTT  19080
19081  TAATATGGTC TACTTACAAT TTGTTTCATG ATTGAGTGGG TCAGTATAAT AAAGGTATAA  19140
19141  ACATGAAATA ACATAGAAGG AAAGTTTGCA AGAGGATTT CAAAGAAGTA CCTGTTGGGT  19200
19201  ATTCAAAGA AAGTAGGGAT AAGCTTAAGG TTAAAATCTT TCTAGGGAAA GTATAGTGTT  19260
19261  CAGAGGTAAG ATTAAAAACC ACATTACTGA AATGGAGTCT GCAGCATTCA GCCCATTCAA  19320
19321  TTGGCATTAA ACTGGTAACT GGTGAAATAA GTATTGTGAG TTGAACTTTA ATTCTAATAT  19380
19381  GCTTGGCAAA GCCGAATCAC AGTGTGCTTC ATCTTTGTGG ATACAAAATT GGAATGCACT  19440
19441  CTGCTATTTA AAATGTGTTC TTACTCACTA GCGTTTGTCA TTAACTTTGA CGTATACTGA  19500
19501  GCTCTTACTA TACTGACGAT GCCCTGGACT ATTTGATTCG ATACTCACAA TTCATAAAGT  19560
                             [I1R(2265)]
19561  AGGTATTATT GGTGTTCTCA TTTTGCAGGT GAGGAAAGTG AAATCCAAAA AGGTTAGATA  19620
19621  GCTTGCCTAA GTGCCAAAGC TGGGTCTCAA AAAGTCAGCC CATTGGGCTC CAGGGCCTGT  19680
19681  TCTGAGAACC TTGACACTAG ATTGTTTCCC TTTAGAGGAG AACAGCTTCC ATCCCTGTCT  19740
19741  TCTAACTCTA CCAAATTAAC TTGGCATTTC AGAACTTGAT TTCCCACATA CAGATACACT  19800
19801  TTTCATGAAC ATTTCCCAAC TCTCAGAGTT AGTTTCTTTT AAAAGGTGGG AATGAAAAAA  19860
19861  CAAAACTTGG AAAATCATCC TCTTCTGGCA AAGTAGAAAG GTGGATCCAG GAACCTTTTA  19920
19921  ATTTACAAAT GGAATTCCCA GTTTGGCCAT TATCCAGAGA CCATGGATGG GCAAATTAAG  19980
19981  GCCATTGGGC TAAATCCAAC CAATTGTTGG TTTTTTTATA GCTCAATATC TAAGAATGAT  20040
20041  TTTTTACATT TTTAAAGGGT TGAAAAGAA AAACCAGTCA CAACGTGATA TGTGAAAATT  20100
20101  ATATGAAATT CACCAAGAGT GAGCCCTAAT ATATTAACTA TGGATGTTGG GTGATAATAT  20160
20161  GTCAATGTGG GTTCATTGAT TGTAATAAAT GTACCTCTCT GATTGGAATA TTGATAGTGG  20220
20221  AAGAGACTGT GCATGTGCGG GGGCACAGGG TATATGGGAA ATGTGTATTT TCTGCTCAAT  20280
20281  TTTGCTGTGA ATCTAAAACT TTTTTTTAAA AAAGGCTAT TAAAATACAT ATATGCAGTT  20340
20341  CAAATTCAGT GTGTCCATAA ATACAGCCAC ACCCATTTGT TTATTTATCA TCGATGGCTG  20400
```

Figure 1 – page 14

```
20401  TTTTTACACT ACAAGTGTAG AACTAAATAG TGGAGACCAG ATGGCCTGAA AAGCCTGAAA  20460
20461  TATTTAATAT ATGTAAAAAC ATTTGCCAAT CATTCAGTTC ATGGCATCTG ATAAAGACTA  20520
20521  AGATACTGGT TGAGATTGTT GCCGCTGGAG TCAAACTTCC AGGGTTCCTA GTCCTCCCTC  20580
20581  TTTCACTTAC TAGTTGAGAA GTGCTTAACT ATGCTAGTCT CAGTTTACTC ATCTTTTAAA  20640
20641  GTGAATCAAA ATAGAACAGT TATGGGACTT TTTTTTTTTT TTTTTTTTTT TTTTTTTTT  20700
20701  TTTTTTTTTT TTGAGACGGA GTCTCGCTCT GTCGCCCAGG CTGGAGTGCA GTGGCGCAGT  20760
20761  CTCGGCTCAC AGCAAGCTCC GCCTCCCGGG TTCACGCCGT TCTCCTGCCT CAGCCTCCTG  20820
20821  AGTAGCTGGG ACTACAGGCG CCTGCCACCG CGCCCGGCTA ATTTTTGTGT TTTTAGTAGA  20880
20881  GACGGGGTTT CACCACGTTA GCCAGGATGG CCTCAATCTC CTGACCTCGT GATCCGCCCG  20940
20941  CCTCGGCCTC CCAAAGTGCT GGGATTACAG GCATGAGCCA CCGCACCCGG CCCAGTTATT  21000
21001  GGACTATTTT AAGAATTAAC TGGGTCAATA CACATGAAGC ACCAAATATA TATTAGTAAT  21060
21061  AATTTATTTT GATTTGAGA TTTTGCAACC CTCTTATGGC CTTTTTTAGG CTATGGATAT  21120
21121  ATTTTTCTCA ACTATCTTGA AATCTGCTTT TTTTATATGA GGGATGCATG TGTATGCCCA  21180
21181  GAAGTCATCT TACCTACCAG GAGCTCTAAG ATGACATGGT TGTGTTTCTT GCTTCTATTT  21240
21241  TACCATCCAA TTTGTCCTTC TTGATCAGAA TTAGCTCCAA AGTAGTAGAA GTTACTCTGT  21300
                                                             [I1F(-1423)]
21301  TACTTTCTCT GTCTTCTTAA ATGAAAAGTT GTCAGCGTAG CAAGCCGGGA ACCAATATGT  21360
21361  CTTCTCCAAC ACCAGATTTC TTGCTGACAT ATATGCATTT TATTTTCAGA GAACATTTAT  21420
21421  TCAAACATTT TTGCCATTCC CTGATTCTTA TAAAATGTTA ATACTTTCCA TATTATTATC  21480
21481  TAAGCTTATT TCACATGAAA TCATTGAATG ACAGCAAAAA ATGTAGTTGA GTCACTATTC  21540
21541  TGAAGATTTG CAAAGATTCT TATTCACTAG CAAAAAATGT TAACACTATT ATTAACCAAG  21600
21601  AAGTTCTGGA TAGACTGGAA TTCCAAAGGC CAAACAGTAC CCAGTTATAA GCTACATAAT  21660
                                                     [I1R(-1042)]
21661  TAGGCTCTGT CATTTTAATA AAAGATATTT AGATTCAAGT ATTATTTGTT GAGCAGCCAT  21720
21721  TACGTGCTAT ATCTTTTCCT GGACTTAAAA TCCTTTCCTC CTAACACTAT TACCAGTTTT  21780
21781  AAAGGTCAAG ACAACGAGTC AAGCTTTGGA CTTTTAAAGT TCTTCAACCC TACTAGCTGG  21840
21841  TCACTTTGGG CAAATAATTT CATTTTTCTG AAGCTGTTTT CTGTTTTGAA AGTAGAAAT  21900
21901  AATATGAGTT GCCTGACTGA GCAATTGTAG GAATCAAGGT AATCTATGGA ATAATTTAG   21960
```

Figure 1 – page 15

```
21961  TCAGTATGAG TGAGACACAG AAAATATTTT TCTTTCCTTC ATGATCTGTT AATCCTACAA  22020
22021  AATGCATTTA CAAGCAATTC CCACATCAGC TCAATTCTGG AAAATTTAAG GAATTATTTT  22080
22081  TTTACCTGCT GAAATTCAGG ATCTCAGCTT ATCAGCATCA GAGCCAAAGC CACGTCTATT  22140
22141  ATCTCACGTA AACAGAAAAG CTGTGCAAGT CGCCCCTATA TGGCTGGGCT GTTGGCAATG  22200
22201  TATCCTTGGC AACTAGTAAG AGTGTTCTCA AAAATTTATG CTGGGGAACG GGGGAAGCTC  22260
22261  ACAAATTGTT CTTTGCCTCC AGGTATCTTA ATTTATTCA TTGCCAGTTT TTCAGAGCTT  22320
22321  GGGTAAAATC TCACAAGTAG GGCCAGGACT GGGATGAGGC AACTGAGGTG TCTAGGGTGC  22380
22381  AAAATGTGAG TTGTCTAGAC ACCAAAGTTG TCTAGGTGTC TAGGAGGCAC TCACTCTCTG  22440
22441  GGGTATGTGA GATTTCAACA CCAATGACTT TTTCTTTCCT AGTTGCTGTA TCATGAGAAT  22500
                             I1F(-242)
22501  GTTTGGCCTT ATTATTTTTT AAAGCTGTAC TTACTTACCA AGAGTGGCC AGTTTAGTGA  22560
22561  TGCAAGAGAT TCAGAATGGG AAAAAAAAAG TCAGCTTTAC CCTAGTCAGT TTTGATTAAA  22620
22621  CTCCTTTGAA ATCCATGTTG GAGTTTAAAT GCCCATTCTT GAGGGATTCT TGATGTAGAG  22680
22681  GAGGCCCCTC CAAAGCTTTA AGCACATGTC CAGAGCAAGG GGGAGCTTTT CTGGTGTTAT  22740
                             GSTO2 Exon 2
22741  TTTGTCTTGT TTTGTTTTTT GCCAGCTCCT ACTCTCGGGC TTCCAAATCT GGGGCGATGT  22800
22801  CTCCCCAGGT TAAATTACCC TAGCTCCTGC TCCAGATCGC TTCCCCGTGC CCCGCCAGAG  22860
22861  CCCAGTAGTT CAAAAATTAA ATTTGGGGCA AGGGGTGCGC GCCAGAGCGC AGCTGTTTCT  22920
                                                      [E2F(-34)]
22921  GGAGCCTGCG GCAGCGGTGG CGAGCCACAG GGCGGCGACC GTGAGCTCCG GGAGCTGCGC  22980
                  1     2  3  4  5     6  7  8     9  10  11 [I2R21]
22981  AAACCACCTG GAGACCATGT CTGGGGATGC GACCAGGACC CTGGGGAAAG GTGAGTGCTC  23040
                            M   S  G  D  A   T  R  T   L  G  K  (SEQ ID NO:2)
23041  TCCATGGGGT CCGCGAGCTG GGGGCGCCGC GTGACAGAAA ATGTTGGCTT CGGCGGAGCT  23100
23101  GCCTGGCCTT GGCCTGCAGA CCGGCGGGGC AGGAAGGGAC TTGGAGGGCT CTCCTGAAGA  23160
23161  AAAGCCACAT GCAGCACTGC CCTCTCTGGG ACTTGGGAGT TGGAGCTCCC ACAGCCATCT  23220
23221  TGGGATCTGG GCAAGTGAGC GAGCTCCTTC CTCACCGGGC TGACTAGCCT CTCCTTTCCC  23280
                              GSTO2 Exon 3
                             12 13   14 15 16    17 18 19   20 21 22 23
23281  TGTCCCCCTC CATCGCTGCT CTGCAGGAAG CCAGCCCCCA GGGCCAGTCC CGGAGGGGCT  23340
                              G  S    Q  P  P     G  P  V    P  E  G  L
```

Figure 1 – page 16

```
               24 25 26   27 28 29   30 31 32 33  34 35 36   37 38 39   40 41 42 43
23341   GATCCGCATC TACAGCATGA GGTTCTGCCC CTATTCTCAC AGGACCCGCC TGGTCCTCAA   23400
          I  R  I    Y  S  M   R  F  C  P   Y  S  H    R  T  R    L (V) L  K 44 45 46   47 48                               [I3 R(+54)]
23401   GGCCAAAGAC ATCAGGTGAG AAGCGGGAAC CCAGAGCCCC CGAGCAAACC CAGCGCCTCA   23460
          A  K  D   I  R  (SEQ ID NO:3)

23461   CAGGAGCCCG GGAATGTTTA ACATCTGGGG CGCCCTGCTC AGCTTTTACA AGGGGCTCCC   23520
23521   TGTCCCTTTT TTCGGAGGCA AAGTCAACAA ATAGCAAAGG GCGAGCTTTT TTTTAGCGGG   23580
23581   CCCTACTGAA ATGCGGAGCC CTTTTCCGAG TCACGCCTAT GCATGAAACT TCTAGCCCAG   23640
23641   CGCAGAGTAA TGTGAATGAT GGGGCTGGTG AACTGGTTCC CTCCCAGAAT GTTTAAGGGC   23700
23701   ACAGCCAACA CTACTGAGGC CTTACCTGAC TGCTCCACAG AGGTAGTTCC CCCACCACAC   23760
23761   CCCAGGCATC TTAGGTCACT GTTTCCTTTC TTTATTGAAC TTACTGCATC CAGCATTTTC   23820
23821   TTATTTGTTC ATCCATCTCC CCTCCCCAGT CCCCTTCACC CATGTGCGTT CTCGAGGGTA   23880
23881   GGAACTCTGT CTCTTTTATT CATGAGCTAG GAGAGAGCCT GTCACATAGT GGATGCTCAA   23940
23941   AAAACATCTG TTAAATGAAT GAACAAATCT TTCCAAACAA TGAAATAGAA GGAATTGCTA   24000
24001   TCAAGAGGTG TCTGGAAGTT TTCAAGCACC CTTGAAAACT TGAGAAATGG GTACAGATGC   24060
24061   TTCCAAAAGG AAGTTTGCAA AACCAGCTCC TGCAGGTCTG GATTTGGAGG GCAGAGCAGC   24120
24121   TTTGCTGGGA TGTGGACTGC ATAATGCAGC TGGCCTCCAA GCTAGAGTGT TGAGAATATG   24180
24181   TCACTCCAGG CTCCCGACTC TTGTCTCGGA GAGTCCATCA CAAGGGGGTG ACTTCAGAGT   24240
24241   TTCAGACTCA TGTCAGAGAG ATACAAAGAC TAATACAGAG ATGTTTTAAA TAAAATTATG   24300
24301   TAAATCTGCC TTGTTGAGTA TATAGGGCCT GTATTTCCAC ATTCTTCCCT TTTGCTCAAA   24360
24361   TTAAGCTGAC CTTAAGGTTA CCTGTTTTTT GAGGAAAATA ACAACAACTG GATGTTTTGC   24420
24421   CCATTTGGTG ATAAATTATC AGCTTAGGAG CTGATGTATT TCCTTAGGTC AGCGTTTCTC   24480
24481   AAACTTGGCA CTGTTGACAG TTTAGGCCAG ATAATTCTTT GTTGGAGAGG TGGGATAGAA   24540
24541   GCTGTCCTGT CCATCACTGG ATGTTAGCA GTATCCTTGG TCTCTACCCA TTCAATGACA   24600
24601   GTAGAGTCCC CCTTCCCTAT GCACTACCTT CAGTTGTGAC AACAAAACCA TGTCTCCAGA   24660
24661   CATAGTGATA TGTCCCTTGG GAAGGAGGCC AAAAATCACT TCTAGTCGAG ACCCATTGCT   24720
24721   TTAGGTTGAG ACCCACTGCT TTAGGTCTTG CTATGTGGCC TATGCTGGTC TCGAAATCTT   24780
24781   GGGCTCAAGC AATCCTCCCA CCCTGGCCTC TCAAAGTGCT GAGATTACAG GTGTGAGCCA   24840
```

Figure 1 – page 17

```
24841  CCTCATCCAG CCTCTGCTGT AGGTTTAAGA CAATCTCCTA GACTAAGCAA TGAACGTTCC  24900
24901  CATTTGTTTC CTTTCATGTT TTTAAACATA CGTTCATGCT TCTGGTAACT ATATAGTTAT  24960
24961  CTAAATAATA ATTGTATTAT GTGAACATTA AATAATAATA GTATTATTTG AACATCTAAT  25020
25021  AATTAGAAGA AGAATTAAAA AAGTTATTGC ATGCTTATGT GCCAGGCACT GTCCTAAACA  25080
25081  CTTTATACAT ATCCCCACCA CAGTACCAAG AGATGGGTGT AATTATTAGC CCCATTTTAT  25140
25141  AATTAAGGAC ACTGAGCACA GAGAGGTTAG GAATTCGGTT AAGGTCCCAA GCTAGACCGT  25200
25201  TTATTCTGAT GCCAAAACTC ATACTCTTAA TTGTTAACAT TTACCATATT CTGTTGTGAC  25260
25261  CTGTTAATAC CAGATTTGTA TTTTCAAGCT GTAGAATGTA CTAAACTCTC TAATGCCATG  25320
25321  GTTAAGTGTG TGAGCTCTGA GTCTGTCTGC CTGGCTGTGA TCTTGGCTCT ACTACTTTTT  25380
25381  TTTTTTTTTA GATGGAGTTT CTTGCCCAGG CTGGAGTACA GTGGTGTAAT CTCAGCTCAC  25440
25441  TGCAACCTCC ACCTCCCGGG TTCAAGCAAT TCTCCTGCCT CAGTCTCCCA AGTAGCTGGG  25500
25501  GTTACAGGCG CCCGCCACCA TGCCTGGCTA CTTTTTTGTA TTTTTTAGTA GAGATGGGGT  25560
25561  TTTGCCATGT TGGCCAGGCA GGTCTTGAAT TCCTGACCTC AGATGATCTG CCCGCCCCAG  25620
25621  CCTCCCAAAG TGCTGGGATT ACAGGTGTGA GGCACCGCGC CCGGCCAGCT CTACTACTTC  25680
25681  TTAGTGGGTG GTATTGGGTG TGAGATTCAA CCCCCTTGAG TCTTCTTTCC TATGAGGTGA  25740
25741  GCCTACTTCA GGGGGAATTA TGAGGAACAA CTGAGATAAG GCATGGAAAA CATCCGACAC  25800
25801  ATCTTACTGC AGGAAGGAAG ATGATGATGT TATGTATTTT ATACAAAACT TAAACCTTAA  25860
                                                     I3 F(-85)
25861  AACACTAATT GCAAATTTTA ACTTTTAAAC TGATTGCTTC TGCTTTCAAG AAGAGTGCCT  25920
                                                                GSTO2 Exon 4
                                                                   49 50
25921  GCCTGCAGAT GCCTCTCATT TTTGTTCTGT CTTGTTTTCC TTTTGCTTTT TAAGACATGA  25980
                                                                    H  E
        51 52 53   54 55 56  57 58 59 60  61 62 63  64 65 66  67 68 69 70
25981  AGTGGTCAAC ATTAACCTGA GAAACAAGCC TGAATGGTAC TATACAAAGC ACCCTTTTGG  26040
        V  V  N    I  N  L   R  N  K  P   E  W  Y   Y  T  K   H  P  F  G 71 72 73   74 75 76  77 78 79 80  81 82 83  84 85 86  87 88 89 90
26041  CCACATTCCT GTCCTGGAGA CCAGCCAATG TCAACTGATC TATGAATCTG TTATTGCTTG  26100
        H  I  P    V  L  E    T  S  Q  C   Q  L  I   Y  E  S   V  I  A  C 91 92 93   94 95 96  97 98 99 100 101 102 103 104 105 106 107 108 109 110
26101  TGAGTACCTG GATGATGCTT ATCCAGGAAG GAAGCTGTTT CCATATGACC CTTATGAACG  26160
        E  Y  L    D  D  A    Y  P  G  R   K  L  F   P  Y  D   P  Y  E  R
```

Figure 1 – page 18

```
       111 112 113 114 115 116  117 118 119 120 121 122
26161  AGCTCGCCAA AAGATGTTAT TGGAGCTATT TTGTAAGGTA TATTCAATTT AAAAAGTCAC  26220
       A   R   Q   K   M   L    L   E   L   F    C   K (SEQ ID NO:4)

26221  TCACACTGTA TTTTACTTTG CATGTCTTTC CCAAACCTCA ACCCATTTTA AAGCCAAATC  26280

I4R(+140)
26281  ATTGGTGAAA CTGTTTTGTT TTGATACCAT GTGATCCTCA GGAGATTAGC TAGCATGGAA  26340

26341  TTAGGGTAGA GCATGGCCAC TGATATTAAA GGCTTAACTG CTAGGCGCTT CTCCATTTCA  26400

26401  ACTGGCAGGC TCAGGAGGTA TGGTTATGAC ATGGCAATGA CCGTGTAACT TGAAGCAGGA  26460

26461  ATACTGAAAG AACTGAAAAC TGGTGATCCT TAAAGGGAGT ATTTCTCCAG CTTCAGGTAA  26520

26521  AAAGTAATGG AGTGCGAAGA TTATGCATAG AAGGTGATGC TTTTTTATTA TTTTTTTTTT  26580

26581  GAGACGGAGT CTCGCTCTGT CACCCAGGCT GGAGTGCAGT GGCACCATCT CGGCTCACTG  26640

26641  CAACCTCTGC CACCTGGGTT TAAGCAATTT TCCTGCCTCA GCCTCCTGAG TAGCTGGGAT  26700

26701  TACAGGCGCA TGCCACCACA CCCCCTAATT GTTGTATTTT TAGTAGAGAT GGGGTTTCAC  26760

26761  CATATTGGCC AGGCTGGTCT TGAACTCCTG ACCTCAAGTG ATCTGCCTGC CTCGGCCTCC  26820

26821  CAAAGTGCTA GGATTACAGA CGTGAGCCAC TGTGCCTGGC CAGTGATGCT CTTTAGAAGC  26880

26881  ATAAGAGTGC CTGCTGTCCA GGAAATGTGA AGAATAGATA AATGGTGGCA GCTTTGATAA  26940

26941  TGAAAGAAAA AAGAATGGAG AAATTTTAAG ATGGTGTCTT TGAAAAGGAA TTTTTAAAAA  27000

27001  CCTCAATGAT ATTAACAGCT GACATATATC GAACACTTAT GATGTGCCAG GCACTGTCCT  27060

27061  AGTTACTTTG TAGGAGCTAA CTCATTTAAT CCAACTGCCC TTTGAAGTGG GTACTGCTAT  27120

27121  CGTATCCATT TTTCAGATGA GAACACTGAG GCTTAGAGAG GTTGAGTGTC CCACCTAAGA  27180

27181  ATGTATAGCA TGGAAGCAGC TGATCAAGTA AGGAGCACTG GAGAAACCCT CCTAAAGCAC  27240

27241  CCTGCTTTCC CAGGGTACTA TAAGAAGTAG ATTCCTACTG AGAACCGGAA CCACAGAGAA  27300

[I4F(-94)]
27301  AACCTAGTGC CTCTCACAGG GAGCTGGGGG GTCTGATGTG GGTGTTGCCC TGTTAGGCTG  27360

27361  GAGTTATAAA GCTTCGCTGC CTTTTCAGGC AGAACAGGAA CTGGAAGTTT CCACAGACTT  27420

GSTO2 Exon 5
                      123 124 125  126 127 128 129 130 131 132
27421  CTCCACTGAG AACCTGTGTC CTCTGATTAG GTCCACATT TGACCAAGGA GTGCCTGGTA  27480
                                     V   P   H   L   T   K   E   C   L   V 133 134 135  136 137 138 139 140 141 142 143 144 145 146 147 148 149  150 151 152
27481  GCGTTGAGAT GTGGGAGAGA ATGCACTAAT CTGAAGGCAG CCCTGCGTCA GGAATTCAGC  27540
       A   L   R    C   G   R   E   C   T   N    L   K   A   A   L   R    Q   E   F   S
```

Figure 1 – page 19

```
              153 154 155 156
27541  AACCTGGAAG AGGTACAAAA AGGGGTCCCT CTCCTGGTCA GCTACAGTGG AGGAAGCTAG  27600
         N   L   E    E  (SEQ ID NO:5)

27601  GCAGGGTCGC TAACCTGGTC ACTCTAACAC CAGCTTTCAC AGGCTTATTC TTTCTGCCTT  27660

27661  TGATAAGTCA GACTTCTGAT CATCTGATTG CATGTTTGCC CTCCTCTAAC CTGGTCTAGA  27720

[I5R(+227)]
27721  ATTATTCTGG AAAATCTGAT GAGGAGTTGG GGAGGACATG CCATGAATTG CTTCCTTTCC  27780

27781  CAGAGTCACC CCATCTCCCT GAGTAGCTCT GCATGGCTTC TGTAGCTTCT GCCAATGAGG  27840

27841  TCAAGGTCTG TAAAGGTTAG GGGTTGTGTT TGGCTGCTGA AGTCTAACTA CTGTAAATTC  27900

27901  ATGTTGTAAG GGTTTACTCT CTCACATAAC ATTCTTTCTC ACGTATTATA AGGGTTTATT  27960

27961  CTCACACATA CGGTGGCTCA CACCTGTGAT CCCAGCACTT GGGGAGGCTG AAGCAGGAGG  28020

28021  ATCACTTGAG CCTAGAAGTT TAAGACCAGC CTAGGCAACA TAGCAAGACC CTCCTCTAC   28080

28081  AAAAATAATT TTAAAAATTA GCCAGGCATA ACGATGTATA CCTGTAGTCC CAGCTACTTA  28140

28141  GGAGGCTGAG GCAGGAGGAT TGCTTGAGTC TGGGAGGTCA AGCTGCAGT  GAGCCATGAT  28200

28201  TGCACCACTG CACTCTAGCC TGGGTGACAG AGTAAGTAGG ACTGACAAAA AAAAAAAAA   28260

28261  AAAAAAAAAA AAGCCAGAGG TAGGCAGTTC AGGCCTATCT TGATGGCTTC TTCATGACAT  28320

28321  TATCAGGAAC TGAAGCTTTT TCTCTTTATG GGCTCTGTCA TCCTTAGCAC AACTTAGTAC  28380

28381  AAGGGTATCA TCCTCAAAAT AACAAGATAG CTGCTGTCAC TGCAGCCATC ACATCCAAGT  28440

28441  TCCAGGCTCT GAAAAGGAGA ATATAAAGAA AAAAATGGCA AATGGTCATA CCCCTTTAAA  28500

28501  GGGCTTTAAA TCCTACCAGA AATTCTACTC AATGGCTATT TACATTTCGT TGGCCAGAAC  28560

28561  TTAGTTGTGG GGTCATAACT ATCTTAGAGA AAGCTGGGAA ATACAGTCTT TTAGCTGGGA  28620

28621  TACCCTGAAT AAAATCAGAG GTCTGTAATT AAGGAAGAAG GGGGAAATGG GTGCGGTGGC  28680

28681  AGGAATACTC TTTGCCAGTA GATGCTTCAT TAACCTGGCA GTAATGGAGC TACTTATCCT  28740

28741  GTACTTCTAG AATAATCAGG AAGGCAGTTC TTTTACTTCC TTTATTTTTG CTCCAGAAAC  28800

28801  TGACAAATTC ACCTTATGGG TGGGTGGTTC CTCTATTGGC AGCCAGAGAA TACAATTTTT  28860

28861  TTCCCCTTAA GGGAAGACTG GTTATTAATA CTCTTCCATT TGACCTTTAT CAAGTGGAAA  28920

28921  CAGATTAAAT GTATTGATAT TTCCAGTTGC CTATCTCAAA TTTGTACGAT TAAGTATTTA  28980

28981  TGGATGACGA ATGGTCATGT GTAGGAAATG TCAACCTTTT GTCCTGAGGT CACCAACTGT  29040
```

Figure 1 – page 20

```
29041  GGCCTTGACT CCAAGGAGGC CATATGATGT GGTGGAAAGA ATCTTGGATC TTAGGCTTGG  29100
29101  CTTTACTGAA TTCCAGAACC TTGGGCAATG TTCTGTACCT CTCTGGGCCT TGGTTTTCCC  29160
29161  ATGTGTAAAA TGAGGGATTA TTTTGAAATG TGTGTTCCTC AGAGCCTCTG GGTTCTGCAG  29220
29221  GGGACTGCCC AGTGAGTGGA GGCCTGGTAG ATTGTTCTAG ACACTGCTTT ACTTAGGTCA  29280
29281  GCACTGCCTT CAACCACCAT GTTCAACCTG ACATCTAAGA AGATGGCATT TGGGGAGAGA  29340
29341  GGAGAGCTGC TGCTTTAAAA AAGAAGTTCG AAAATCTTGT GAATAGAGAA TTTATAGTCT  29400
29401  ATTTTAAAGA TCAGCTGAAT GGACCCCATC ATGCCTGGTT ACCTTCTCAC AGATAAACAA  29460
29461  ATACTGGACC AGGGAAAGGA GCTGGGAAAA AAAAAACTCT TGAATTCAA CGATACAGTA   29520
29521  ATTGAAACAT TTTCATCAGT TTCCCTTCTA CCTCCATTTG GATGATGGAT GAACTTTTTA  29580
29581  AATTACAGAT TGCTAGATGA AGTATAGGG TTATGATGGA GATACAGTTC TTCTTCAGTC    29640
29641  GGGGGTCTTT TCCAGGGCAA ATGAACCAGT ATTTTGTGCC ATGAATCGTG CTGCAGATAC  29700
29701  TTGCATACAT CATCTCATTC AATCTTTCCA ACAACCTTCT CAGGTACAAA TGGTACTAGT  29760
29761  CCTGTTTTGC AAATTGGAGT GGCCTCTCTG TAAAGGCTCA GAACTAGGTA CTAGGAATAA  29820
29821  AAAGAAATTA AAGACCCTCG AGGGGCTCAA AGCCTGGACA GGGAGATAGG CTGTTAAGCC  29880
29881  CATTTAAAAC CTGGGTGTGT TGAGTGCTAG GCTGGAGACA TGCATACAAG AAGGCTGGTC  29940
29941  TGTGGGGGTA GATAATGCCT CTGTTGACTC TTAGGATGAA TTAGAGGCAC AAGGGTGAGA  30000
30001  GCCTGGTGTG TTCGGCAAAC AATAATCAGT GAGGGGTTGA CAGCGAGGGA GTGATTGGTA  30060
30061  AGAGGTGAAT GTGGAGGGTG GACCAGAGTC AGATGCTAAA AGGCCTTTTC CACTGTGCCC  30120
30121  AGGGATTTGC ACTTTATTTC AGAGTTGATG GTGAGTAATT GAAGCCTGTC AAGCAGGAGA  30180
30181  GTGGTGTACT CCTTCATGCT TTTAAAGTA TTCAGTCCAT CACTTGAACC CAGGAGGGGG    30240
30241  AGGTTGCTGT GAGCCAAGAC TGCGCCACTG CACTCCAGCC TGGGCAACAG AGTGAGACTC  30300
30301  TGTTTCAAAA AAAAAAAAA AAAAGAAAAG AAAAGAAAAA GTATTCAGCC CAGCTGAGCA    30360
30361  CAGTGGCTCA TGTCTGTAAT CCCAGCACTT TGAGAAGCCA AGACGGTAGG ATCGCTTGAG  30420
30421  CCCAGAAGTT TGAGAACACC CTGGTCAACA TGGCAAACCT CCATCTCTTT AAAAAATACA  30480
30481  AAATGTTAGC TTGGCATGGT GGCTTATGCC TGTAGTCCTA GGTACTTGGG AGGCTGAGAT  30540
30541  GAGAGGATCA CTGGAGCCTA GGAGGTTGAA GCTGCAGTGA GCTATAATTG CACCACTGCA  30600
30601  CTCCAGCCTG GACAACACAG TGAAACCCTA TCTCAAAAAA AAAAAAAAAG AAGAAGAAGA  30660
```

Figure 1 – page 21

```
30661  AGTTCAGCCC AGCAAGAATG TAGAGGATGG ATTAGAGTGT CCAAGAGGAG GGACTGGGAA  30720
30721  GGGACAAAGA GGACCCCACT AACGAGGGTT GGAGAGGGAG GTTTAATTAG AGAGATTTTG  30780
30781  AGGAACTAAG ATGAGATGAA ATCTGAGGAA GGAGTAGGAG TTATGGAGGA TGGTTTCCAA  30840
30841  GTTTGTGGCC GGTAAATGTG ATGCTTTTCA CTAAGAGTTT GAGGGAAGAC ACATTTGTC   30900
30901  AAATTTGTGG TGTTGATGGG ATATTCATAT GCGGGCAGAG CTTAGAAGAA CAATGTATGG  30960
30961  TCTCTACTGG ACCTTTGGAA TGGTTTTATG GGCTAGGAGC TTTCACCAGA GAGTTTAGGA  31020
31021  ATGTCATTAG TGGGGTGGTG ATAAATGTTT AAGAATCAAT TTTCTCTTAA AAGAGAAAGA  31080
31081  AAAAGAAAAA GCACGGATTT ATAGCATTTG CTGATTTGGG TGGTGTAAAC ACTTCCGTCA  31140
31141  AGGTTAATTT TGAGCTACCA ATGTGCTATT TCTAAACTCA AGAGCTGGCA AAAGATGTGG  31200
31201  GCAGCTCCAG CATGTCACTG AATAAGAAAT TTCACTTTAT CTTCAATAAC TGAGCCCCAG  31260
31261  GAACACTGTT GTTAACCAGC CTCTATATAG GTAGCTTTCA CTAACCAGCC TCGGTGTAGG  31320
31321  TAGCTTTCAC TGATGCTATT TAAGGACCAC TGAGTACTCC ACATTGTCCT AACAGGTTTG  31380
31381  AATGTGGTTT TGTCCCATAG AATGTTAGCA AGAATTGTAG CTATGGCTGG GCGTGGTGGC  31440
31441  TCACACTTGT AATCCAGGCA CTTTGGGAGG CCAAGGAGGG AGGATCACCT GAGGCCAGGA  31500
31501  GTTCAAGACC AGCCTGGGCA ACACAGTGAG ACTATGTTTC TACTAAAAAT TAAAACATGA  31560
31561  ACTGGTCATG GCAGTGCGGG TCTGTAGTCC CACCTTCTCT GGAGGCTGAG GCGGGAGCAT  31620
31621  CTTTTGAACC CAGGAGTTTG AGCTTGCAAT GAGCTATGAT CGTGCCACTG TACTCCAGCC  31680
31681  TGGGTGACAC AGCAAGACTC TGTCTCAAAA ACAAATAAAC AAAGAATTAT AACTACAATG  31740
31741  TAGGAAATAT TGAAATCTGA AAACATGACC AATGTACTTG AATTATGCGA TCTGTTCCTT  31800
31801  TAAATGCCAA ATATTTATT CCAGGAGATT CTAGTGAAAT TGAAATTTAT CAGAATAATT   31860
31861  CTAATGGAGA GGATCCCCTG ATTTATGTAA CTCTTTCACA TGGTTTTGCA CAATCAGGAT  31920
31921  TTTTTGTGAG CTAAAAATAT ATTAAATACT CATTGTCTTT CTGAGTGATA AGCAAGCCAA  31980
31981  GATTTCATGC ATAATCTTCT GCTATGTTAT CCTGAAACAG AAGGCTCAGT TAACCTTTTG  32040
32041  TGGCCTTAAA CTCTGACACT TCTTCTTTT GAAATAACTG CCTTGTCTAA CTTTTTAAGT   32100
32101  TTTTTTTTT TTTTGGCTTG TTTTTTTGTT TGCTTGTTAG TTTTTTAAAT CTAGTTTCAG   32160
32161  GTGGGTTCAG TGGCTCATGC CTGCAATCCC AGCACTTTGG GAGGCCGAGG CGGGCAGATC  32220
32221  ATTTTAATCC AGGAGTCCGA GACAAGACTG TACAACATGG CAAAACCTTA TCTCTACAAA  32280
```

Figure 1 – page 22

| | | | | | | |
|---|---|---|---|---|---|---|
| 32281 | AAATACAAAA | ATTAGTTGGA | TGTGGTGATG | CATACCCGTG | GTCCCTGCTA | CTTGGGAGGC | 32340 |
| 32341 | TGAGGTGGGA | GGATCACTTG | AGTCCAGGAG | GTCAAGGCTG | CAGTGAGCTA | TGATCATGCC | 32400 |
| 32401 | ACTGTACTCC | AGCCTGGGTG | ACAGAGTGAG | ACTTTGTCTC | AAGAAAAAA | AAAATTAAGT | 32460 |
| 32461 | TCCATCAAAA | TCAAAGATTT | ATTGTGCTTG | TTATATAACC | ACATTTTTCT | CTAATATCTT | 32520 |
| 32521 | TTACAATTCT | TTGAGATATA | TTACTGCCAC | TTTTATTATC | AAACTAGCAG | CCTGCTCACT | 32580 |
| 32581 | GGCTTTCCTG | TTCTGAACAT | TGGCATGAGT | TTTAAAACTA | TGACACTTGT | CTTGTCTTGC | 32640 |
| 32641 | TGCACTTTAT | GTCTTCAAGC | AGATTTTCTA | GCCCTTACTG | AATCATTACT | CTAAGCAGCA | 32700 |
| 32701 | CACATTTTTT | AGTTTTATTC | TTTTTCAGGT | ATTGACTTTC | CCATTTCAGA | ATGGGACTTG | 32760 |
| 32761 | AGCCAGGCTT | CATTTGATCT | TTGTGGATTT | GAATGTGGCA | GGACCTCTTG | GTGTCACTTT | 32820 |
| 32821 | TTATCTGTGC | CTTCCAAAAA | TATTTTCATT | ATGGAAGTAG | TCAAATCAAG | TCCAAGTGCA | 32880 |
| 32881 | GTGAAAGGTG | GATTTGGTCA | GATTTCCTTG | AGGCTTTGGA | GTTTTGCTTT | AAATCTAGAA | 32940 |
| 32941 | AGTGTTCGTG | GCTTCTGAAT | TGGTTCTGCA | CTCTGACTAT | TGCTTGGTCC | TTTCTTCGTC | 33000 |
| 33001 | ATCATCAGAG | CTCCATAAAA | GAGAGCGGGG | AGGGGATAAC | ATAAATAATG | CTGAAATAGC | 33060 |
| 33061 | CCTGAGGGAT | GAGACATGGC | CCAGCAACTG | AAGCCTTCGT | CTGCCCGTGG | CCACAGGGCA | 33120 |
| 33121 | CTTTATGGTT | TTGCTTCTTG | TCATTCAACC | ACCTGCCTTG | GGGTGCTTCA | CTTTGCATTT | 33180 |
| 33181 | CCACGCAGAG | TTTCCCGCAT | TGCCAAACTT | GATCATGTGC | CTTATGTGTA | GCAGTTTGCA | 33240 |
| 33241 | TGAGGTGGAA | TTTGCATAAA | TTATGTGTGC | ATCACCCAGG | AGCATCTGTA | GTTAAATACT | 33300 |
| 33301 | TTATTGATTC | TAAATTTTGC | CCATAATCTT | AATTTTTTAA | TTATTTTATT | TTCTTTTCCT | 33360 |
| 33361 | CTTTTAGAGA | TTGGGGTCTC | TCTCTATTGC | CCAGGTTGGA | GTGCAGTGGC | ACAGTCATGG | 33420 |
| 33421 | CTCACTGTCG | TCTTGAGCTC | CTGGGCTCAA | GCAGTACTTC | CACCTCAGCC | TCCCGAGTAG | 33480 |
| 33481 | CTGGGATTAC | AGGCTGAAGC | CACCGAGCCT | GCCTCCGTTA | TCTTAATTAT | TATTATAATT | 33540 |
| 33541 | ATTTTTTTGA | GTCAGGGTCG | CACTCTGTCA | CCCACATTGG | AGTGCAGTGA | CACAATCACG | 33600 |
| 33601 | GCTCACTGCA | GCCTCAGCCT | CCTGGGCTCA | AGTGATTCTC | TCACCTCAAC | CTCCTGAGTA | 33660 |
| 33661 | GCTGGGACCA | CAGGTTCAGG | CCACCATGCC | CAACTGTTTT | GTTTTTGTTT | TTATTTGTTT | 33720 |
| 33721 | TAATTTTTTG | TGGAGACGAG | GTCTCACTAT | GTTGCTCAGG | CTGGTCTTGA | ACTCCTAGGC | 33780 |
| 33781 | TCAAGTGATT | CTCCCACTTC | AGCCTCCCAA | AGTGCTATGA | TTACAGGCAT | GAGCCACTGC | 33840 |
| 33841 | ACCTGGTAAT | CTTAATTTTT | AAACTGTTCT | TCTTCTCAT | CAAAAAGAC | ATTTATTCAA | 33900 |

Figure 1 – page 23

```
33901  GTTAGATTAT ATTGTCTTGG TTTAGTTTTG CTTTTGCTCT TTCTTAATTT TTATTAATTT  33960
33961  CCAGTGATGA AATTATTTAT ATATTGTTTA ATTGTTTCTC CTTTGATATC ACCAGGATAG  34020
34021  GAAGAAAAGA AAGTTTATAC CTGGTTAATT CGTCACTGAA AACAATTTTC TGTATCCTTT  34080
34081  TATATATAGT AGACTACAAG CTAAATTTTT TATCATCTAA GTTAACATGT CTATAAACTA  34140
34141  AATTCATTAT TACTAGCTAT TTTTAATAAG TTATTGAGAT ATAATTCATA TGCCACAAAA  34200
34201  TTCACCCTTT TCCAGTGTAC AATTCACTGG CTTTTAGTAT ATTAAGTGAG TTGTGCAACT  34260
34261  ATCACCAGTA TTTAATTTCA GAGCGTTTTT TTTATCATCC CCCAGAAAAA CTGCTCACTT  34320
34321  GTAAGCTGTC ATTTTCCATT TCTTCTCAAT CCCTGTGGCT GTACGCAGCC ACTGATCTGC  34380
34381  TTTCTGTCTC TATGGATTGA CTTATTCTAG ACACTTCATA TAAGTGGAAT CATACAACAT  34440
34441  GTAGCATTTC ATGAGCTATT TTCACATACC ATAATGTTCT TAAGGTTCAT CCTTCATTCT  34500
34501  TTTTTATGGC TAAATAATAT TCCATGTGTG AATACGCACA TTTTGTTTAT CCACATCTGG  34560
34561  GAAGGTTCCA CTCTTGGAAC TAATATGGAT AATGTTGCTG TGAACACCAT GCAGGTTTTT  34620
34621  GCATGAATAT ACGTTGTTAT TTCTCTTGGA TTTGCTAGCT GATTTAGCAT GTTTACTAAC  34680
34681  ATGCCATTTT AGTTGTAACC ACCATTCTTT CACACTTGGG AACTGATTAT CCCTGACTCA  34740
34741  GGATGCCTCG TTAAGTGTAT TAGTGCTGTT GCTAGTTGGG TTACTTCCTT CATCATCCAA  34800
34801  TTCTGACAGC TGCTAATATT TGCTGTACTT CTTTCAATAG CTTTCTGATA TACCCTTTCC  34860
34861  CATCACATAA ATAATAGAAT AATAATTATT CTTATTATTT AAAAATTAAT TTTACTCTTC  34920
34921  TCCAATTATA AAGTAATACT TGTTCATTAG AGAGAATTTG GAAAATACAG GAAAACATAG  34980
34981  AAACTAAGGA AAAAAATTA TAATCCCACT ACCCAGAAAC AACCACTGTT ATTATCTTGG  35040
35041  GGACTTTTTT GTTTTTGTTT TCTGTCCTTT TCTGCTATGT ATATTTTATG TAGTTGAAAC  35100
35101  TTGGTTACTA TTATGATGTA AATATTCCCC ACACCCCTG CCATTTTATT TTGAGACAGG  35160
35161  GTTTTACTCT GTTGCCCAGG CTGGAATGCA GGGTGCAATC ACGCCTCACT GCAACCTTGA  35220
35221  ACTCCTGAGC TCAAGGGAGC CTCCCAACTC AGTCTCCTGA GTAGCTGGGA CTACAGGCAT  35280
35281  GTGCCACCAT GCCTAGCTAG TTTTCTTTTT AACTTTTGTA GAGACAGGGT CTCCCTCTGT  35340
35341  TGCCCAGGCT GGTGTCGAAC TCCTGGGCTC AAGTGACCCA CTTGTCTTTG CCTTCCAAAA  35400
35401  TGTTGGCATT ACAGGTGTGA GCCACCACAC CTGGCCAATT TTTATAAACT CTGTAAATGC  35460
35461  TTATTTACAT ATATAAGAGT GTTCCTTAGA GCAGCAGCAT TATTTGTGAT GATGACAAAT  35520
```

Figure 1 – page 24

```
35521  TAGGAAACAA TATTCATTAG ATGGTGAGTG GTTAAGTAAA TCATGTCTGT CTTGTGGAAT  35580
35581  TCTGTGGAAC GGCTGAAAAT GAATGAGGTA AATCTATGTG TACTGACATT AAAAGATTGC  35640
35641  CTAGAAATAT TAAATGAATC ACACAGTAAT ACAGGTGGTA TGATCCCATT TTAGCAGAAG  35700
35701  AAAACAAAAC TGAACCATGC AGGTGTGCAC ATACATGTAA ATAAGTGGCT AGAAAAGTAT  35760
35761  CTAGAGAGAA ACACATCCAC CTCCTAGTAA TGTCTCACAC TGGGAAGGGG GCTGATTAGA  35820
35821  ATTAGGGTGG GTAAGAAAAG TGGTTAAGGG CAGGGACCGG GAGGGAAGAT TTTGTCTTTT  35880
35881  ACATTATTTT CTGTGTTTGA TTTTTTTTTT AATGATGGGA ATGTATTTCT GTATTAAATA  35940
35941  TGTAAGTTTT AAAAGTAGAA AAAACACTT TTTTTTTTTT TTTTTGGGA CGGAGTCTCG  36000
36001  CTCTGTCGCC CAGGCTGGAG TGTAGTGGTG CTATCTCGGC TCACTGCGAG CTCCACCTCC  36060
36061  CAGGTTCATG CCATTCTCCT GCCTCAGCCT CCCAAGTAGC TGGGACTACA GGCACCCGCC  36120
36121  ACCACGCCCG GCTAATTTCT TTTTGTATTT TTAGTAGAGA TGGGGTTTCA CTGTGTTAGC  36180
36181  CAGGATGGTC TCCATCTCCT GACCTTGTGA TCCATCTGCC TCGGCCTCCC AAAGTGCTGG  36240
36241  GATTACAGGC GTGAGCCACC TCACCCGGCC GAAACACTT TTAATGTCTG CATACTTTGC  36300
36301  CATGTTTATA AACCATAAAG TTATTTATCC AGCACACTAA TTAGGAGTGT TTAGATGGTT  36360
36361  TTCAGTCCTT TACTGTTTTG AATGGTGCTG CAGGGAACAT CAGCTTCTTT GCATAAAAAG  36420
36421  CATTTCTCT ATTTTAGAAT ATGTTCTTAA GCTGGACTCT CAGGAATGGA ATTACCAGAT  36480
36481  CAAAGGGTAT AATGAGCACA TTGGAGGCTT GGACTGTATT TCACTAAATT GCTTCCCAAA  36540
36541  AGACTTGTGT TGTTTGCCCC TCACCAGCAG TATGTGAAAA TGCTCTTTGC CCTATATCCT  36600
36601  TTTCACTGGT GGGAGACTTC ATTCAAAAAG ATATTTGTTT GTTGAATAAT ATTTGCTGTG  36660
36661  GAGATACACT GTAGTTCCTC ATTGTTGACT TAATGCATAT TTCTTTGATG GCCAGGGAAG  36720
36721  TGGAAGGTTT TCCCGGAAGT ATGTCATCCC TTGCTCCTGG TCTTGCAAAA TTTGTCTGTT  36780
36781  CAGTTCAGGG GCTTTGCCTA TCTGGCCATC AGAGTCTTAC TAATTTTCTT TGTTGATTTG  36840
36841  TAAAAGTTCC TTTTAAAGCG TTCCTTGTAT AGAAAAGATA TTTGACTGGT TTTAAAACAC  36900
36901  ATTTTTGTTT TCTTTTGACT TTTAATTTGG CTTATATATT TTTGCATATG GAAGTACAGC  36960
36961  ATTTGAAAGT ATTGTGCTAT AAGGCTTTCC TTATATGTGC TATGATTTCC TCCACTGTTT  37020
37021  TATGTGTAGG AAGTCCTCTC CCCACTTCAG AGACTTGATA AATATTCATT TATATTTTCA  37080
37081  TCTACCACCA ATCACTTTAC AGACATTTGA CTGGTCAAGC ATTACCCTCC TAGCTTTTCC  37140
```

Figure 1 – page 25

```
37141  CCCCACACTA TCTTACAAAT ATATTGTGAT TTGTTTTAGT TTTTGTTTTT TGTTTTTGAG  37200
37201  ACAGGGTCTC ACTCTGTCAC TCAGGCTGGA GTGCAGTGGC ATGATCATGG CTCACTGCAG  37260
37261  CCTCGACCTC TCAGGCTCAG GTGATCTTCC TACCTTAGCC TCCTGAGTGT CTAGGACTAC  37320
37321  AGGCACCACT ATGCCTGGCT AATTTTGTGT ATTTTTTGTA GAGATGGGAT TTTGCCATGT  37380
37381  TGCCCAGACT GGTCTCGAAC TTCTGGGCTG AAGCGATCCT TCCACCTTGG TCTCCCAAAG  37440
37441  TACTAGGATA AAAGGTGTGA GCCACCACAC CCAGCCCTAC AAATATATTT TGAAGATACG  37500
37501  AATTAAGCTC ATTAAAAGGA TGCCAGCATA GAATTTTCAG AGTGGTCCTT TAATCCCCAA  37560
37561  ATTTTGACAG TTGTATTCTG CACCTTCATG GAGAATCTAG GTCATAACTG ATGGGCAGCA  37620
37621  GGAGGGGCAT GTTCTGCTGC AGGTCCTCCC TCTAAGGCTC CTTCCCAGAG GAGAAAATGG  37680
37681  TCTTAAATAT GCCCTAGGTT TGTTCCACAC CCTAGGTTTG TTTTACAGGG AACTGGGTCA  37740
37741  TCACATGGTT AGCTCAGCCT CAGCTATATC ATTTTAGCAG GGATCTGAGA TTTGAAATCT  37800
37801  TAAGAACCTC CATTTATCTT TTATGAGCTC AAAACATTTC TGCCCTCCAA AAGACTTGAA  37860
37861  TAGACATTTC TCAAAGAAG ACACACAAAT GGCAAACAGA CATATGAAAA GGTGCTCAGC  37920
37921  ATCATTGATC ATCAGAGAAA GGCAAATCAA AACTACAATG AGATATCATC TCACCCCAGT  37980
37981  TAAAATGGCT TACATCCAAA AGACAGGCAA TAACGAATAC TGGTGAGGAT GTGGAGAAAA  38040
38041  GGGAACCCTC GTTCACTGGG GCGGGAATGT TAATTAGTAT AACCATTGTG GAGAACAGTT  38100
38101  TGGAGGTTCC TCAAAACACT AAAAATTGAG CTACCATATG ATCCAGCAAT CCCACTGCTG  38160
38161  GGTACACACC CAAAAGAAAG GAAATCAGTA TATCAAAGAG ATACCTGGAC CCTTATGTTT  38220
38221  GTTGCAGCAC TGTTTACAAT AGCTAAGATT TGAAAGCAAC CTAAGTGTGC ACGAATAAGG  38280
38281  AATGGATAAA GAAAATGTGA TACAGGCCGG GTGTGGTGGC TCACTCCTGT AATCCCAGTA  38340
38341  CTTTGGGAGG CCAAGGCTAG CGGATCACTT AAGGTCAGGA GTTCGAGACC AGCCTGGCCA  38400
38401  ACATGGTGAA ACCCTGTCTC TACTGAAAAT ACAAAAATTA GCTGGCATGG TAGTGCATGC  38460
38461  CTGGAATCCC AGCTACTCAG GAGGCTGAGG CAGGAGAATT GCTTGAATCT GGGAGGCAGA  38520
38521  GGTTGCAGTG AGCTGAGATC ACACCACTGC ACTCCAACTT GGGTGACAGA GTCACACTCT  38580
38581  GTCTCAAAAA AAAAAAGAA AAAGAAAAT ATAGTACATA TACACAATGG AGTACTATTT  38640
38641  GGCCATGAAA AGAATGAGAT CCTGTCATTT GCAGCAACAT GGATGGAACT GGAGATCATG  38700
38701  TTAAGTGAAA CAAGCCAGGC ACAGAAAGAC AAACATCACA TGTTCTCACT TATTTGTGGA  38760
```

Figure 1 – page 26

```
38761  ATCTAAAAAT CAAAACAATT GAACTCATGA ACACAGAGAG TAGAAGGATA GTTTGCAGAG  38820
38821  GCTAGGAAGG GTAGTGTGAG CTGGCAGGGA GGTGGGGATG GTTAATGGGT ACAAAAAACA  38880
38881  GAAAGAATGA ATAAGACCTA CTATCTGATA GCACCACATG GTGACTATAG TAAATAATAA  38940
38941  CTTAATTGCA CATTTAAAAA TAACTTAAAC AGTGTAATTG GGTTGTTTGT AATTGAAAGG  39000
39001  ATAAATGCTT GGGGGAGTGG ATACCCCATT CTCCATGATG TGCTTATTGC ATACTGCATG  39060
39061  CCTGGACCAA AATATGTACC CCATAAATAT ATACACCTAC TATGTGCCCA CGAAAAATAA  39120
39121  AATTAATAAA AGATTTCTGC CCTGGAGTTG AGTACTTTTC CACTGCTTCT GGAAAAGGGC  39180
39181  CAGTATTGCT GATGTACTGG CATGTTGCTT TGTGTCTTTT TAGGGGCCAC AGAGGGTGGA  39240
39241  GGATGGCTTC TGCTTTTTTG GGGGGCAGAG AGTAGGGGAT GACCTCTGCA TTTTCAGAAC  39300
39301  GATTTTCATG AGGAAAAACT TTCTTCCTCC TCCAGCAAGT ACAGCAGCCC CCACTGGGAG  39360
39361  CCACCACACT GTTTCGAGAT TGGGGGCTTG GGATTTCTTG GCAATGGTGT AGAGGATGGT  39420
39421  GAAGGTGAGC TGGCCTCTTC AAGGTTTGAA GCTCAATTAT TGAGGCTGAA CCAAAGAGTT  39480
39481  GAAGACTGGA GCTCTCTCGA ATGCCTGGTT TGGAGATGTC TGGGATTCGC TTCTCCTAAT  39540
39541  GATCTTGCTT CTCTCGCGAA AACTGCAGAT TTCTTCATCC TCCGGTTGAA CGTTCTTGGG  39600
39601  GAGCCGCGGC CGACGCGCCT CGCACTGATG GCCACCAGGG GGAGCCCCGC GCGCTTCCTC  39660
39661  CTTCCCCTTG TGTTCCAGGG CGCACTTCAA AACGCTGACG TTCTCCTTCG TCCCTCTGGG  39720
39721  GGCGCCCGAG GGGCCCTCGC AGAAGATGAG GTGCCTTTCC AGCCAGGCTT CTCGCGTGCA  39780
39781  GGGCTTGGGA ACAGTGCATC CCCATCCTAC CAAGCAGTCC CTTCCTCTTC ATTTGCATCG  39840
39841  CGTCCGTAGT CTTATTTTTC AGTGAACTGG AGAACAGAAA ATTTTAAAAT AGATTTTTCT  39900
39901  AATATTCCAG AAGGTCAAAC ACCTTTCTGC AAAGTATCTA GCATACTAAA GGGGAAGTAA  39960
39961  TTTTACATGT CTGGAAGGTA CCATGTTTGC ATTAGAAAGG AGCTCTTCTA TTGTACTAAA  40020
40021  GTCTCCAACA AACCTCTTGA ACTCTTAAGC CTGAATTGAA AATGTGTCAA TGTTTTCAGA  40080
40081  AAATCTGAGG CCTAGAAGCT AGAGCCTCAG TTCCCTCCCC TGCCATTTGT AGAAGCCTTA  40140
40141  TAGGGGATAT CTGGGGTTTT TGAAGAAAAA CACTTTCTAA GTAGGCTATT TTGCTTTGCT  40200
40201  TGTTCATACA AAAGACAGGG GTTCTGAAAG TGAGGGATGC CATTGTGAGG GAAGCTATTC  40260
40261  AACATTAAGA ATGGCCAATA TCTTTTTTTT TTTTTTTGT CTTTTGAGAG GGGGTCTTGC  40320
40321  TGTGTTTGTT GCCCAGGCTG GAGGGCAGTG ATGTGATCAT AGCTCACTAC AGCCTCGAAC  40380
```

Figure 1 – page 27

| | | | | | |
|---|---|---|---|---|---|
| 40381 | TCCTGGGCAC | CACTACACCC | AGCTAACTTT | TTTTATTTTT | TGTAGACACG | GTCTCACTAT | 40440 |
| 40441 | GTGCTCTAGG | CTGGTCTCGA | ACTCCTGGCC | TCAAGAGATC | CTTCCACTTT | GACCTTCCAA | 40500 |
| 40501 | AGCACTGGGA | TTACAGGCGT | AAGGCACAGT | GTCTGACCAC | CAATATCTTT | TTTTTTTTT | 40560 |
| 40561 | TGAGACAGGA | TCTCACTCTG | TCACCTAGGC | TGGAGTGCAG | TGGCGTGATC | ACTGCTCACT | 40620 |
| 40621 | TCAGCCTCTA | CCTCCCAGGC | TCAGGTGGTC | CTCCCACCTC | AGCCTCCCAA | GTAGCTGGGA | 40680 |
| 40681 | CTGCAGGCAC | AGACCACAAT | GCCCAGTTAG | TTTTTTTGTA | GAGACAGGGT | TTTGCTATGT | 40740 |
| 40741 | TGCCCACGCT | AGTCTCGAAC | TCCTGGGCTC | AAGCAGTCTG | TCCACCTCAG | CCTCCCAAAG | 40800 |
| 40801 | TGCTGGGATT | ACAGGCATGA | GCCACCATGC | CTGGCTGTAT | CTTTATATGT | GATATATAAT | 40860 |
| 40861 | CAGGTGGAAG | AACTCAACAT | AGAATTCTTT | AAAAGGATGG | ATTGGATATT | AACATAACTA | 40920 |
| 40921 | CTGCTAAGTG | GATCTAGATC | TAACACCCAT | TTTTCATTCC | ATTTCTGATG | ATAAAACACT | 40980 |
| 40981 | TAAGAAAGAC | AAGACATTGG | ATGTTAAGTC | TGTCAGTTTA | TTTTGCCTCT | GCCTCTATCC | 41040 |
| 41041 | TAAAATTTTT | TCAGAGGGGT | AAATGCAAGG | GACTTGTTTT | AAATTGAGTA | CAAGAAAGAA | 41100 |
| 41101 | CTATTTTAGT | AAAGTTGCCT | GAAGATCTGC | TCATCAGTGG | AATAAAACAG | GAAGGACAGA | 41160 |
| 41161 | ATTCTGATAA | GCTCTTTCAT | AATGACTATG | TTGGAATGTC | TCATCCCTCT | GTCAGTTGCT | 41220 |
| 41221 | TTGGCTTGAG | CTTCTGATTC | AGAGAGCATG | AAAAGGTGAG | ACTAAGGAGG | AAATTCTTTT | 41280 |
| 41281 | CACAGAGAAG | CTCAGAGCCG | AACCAATCCT | TGGCTGTAGA | GAAGGAGGAG | CTTTCAGAGT | 41340 |
| 41341 | TTGCTGGTTC | CAAGCTTTTT | TCTGTTACTT | AAATTTAAAG | CTGGAACAGA | AGGTCAAGAA | 41400 |
| 41401 | ACAGGAAGGA | AAACCGTATC | AAGATATCAA | GTCATGGTAT | TCTTTTTCAT | TCTTACAGAA | 41460 |
| 41461 | AAGAATTCAC | AAGAGACTTG | AGGAAGCTTT | TTTATTTTTA | TTTTGTTCTG | TTTATTTATT | 41520 |
| 41521 | TATTTTAAGA | TGGGGTCTCA | CCCTGTTGCC | CAGGTTGGTC | TCAAACTTCT | GGGCTCAAGT | 41580 |
| 41581 | GATCTGCCCA | CTTCGGCCTC | CCAAATTGCT | GTGATTACAG | GCATGAGCCA | CTGCGCCTGG | 41640 |
| 41641 | CCAATTTTTT | TTTTTTTTT | TTTTTGCGA | CAAGGTCTTT | CTCTAGAGTG | CAGTGGCATG | 41700 |
| 41701 | TTCACAGCTT | AGTGCAGCCT | TGACCTCCCA | GCCTCAAGTG | ATCCTTCCAC | CTCAGCCTCC | 41760 |
| 41761 | TTAGTAGCTA | GGACTACAGG | CATCACTAGG | ACTACAGGTG | CCACCACCAC | GTCCAGCTAA | 41820 |
| 41821 | TTTTCGTATT | GTTTGTAGAG | ACGGGGTTTC | ACCGTGTTTC | TCAGGCTGGT | CTCAAACTCC | 41880 |
| 41881 | TTGGCTCAAG | CAATTTAAGG | AAGCTTTTCA | TTAGAGTCTA | AAAATACATA | TTTGAATTGA | 41940 |
| 41941 | ATGACACAGG | GTTGACACTA | GTCAGAGAAT | TAGGAAAATG | TGATATGCGT | GTTAGTTCCA | 42000 |

Figure 1 – page 28

```
42001   GTGCAAACCG GAGAGCCCGT TAACCTCCCT GGGACTGGGT TTCCTCCTCT GCACAGCAAG   42060
42061   GCTCCCCTGT CCTTCCCCAT GGGAGACAAG AATCACATCA CCAGCATGTT TTCCTCTCCC   42120
42121   CTTTGGCTGC CAGGAAACTC AAGAGTCAAA TTCAAGGCTT TATTGAAGGA ACTCTGCAGG   42180
42181   ACCCAGGACG TGATATCTTG ATACTGTTTT CCTTCCTGGT TTTTGACCTT CTGTTCCAAC   42240
42241   TTGCGTTTTC CCTGATTATA GCATTTTATT ATTTTTCATA TTTAGTATGT AGTGCACATT   42300
42301   TTTACACTAC ACTTCTAATC CTTTGTGTAA TGATCATGGT AGAAATAAAT GGTGAAATGA   42360
42361   GGAGGTCCCA CTTAGATGAG TTTCAGGGGT CCTTCCAGTC CCAATTTTCC AGGATTCTTA   42420
42421   AGGGGAAAAA GTAATTTTAC ATGTCTGGAA GGTTCCAGGT TTGCACAGAA GGGAACTCTC   42480
42481   CTATCGAGAG TCCTGAGGAC TTCAGCAGAC CTCCAGGGAG GCCTGTCCAG GATGTTCTCC   42540
42541   TACGTCTGTA AAGGAGTGAG CACTTGTGC TAGTTTAGGG AAAGACAGCT TTTCTGTTGG   42600
42601   GATTTTAGAC TTACCCTGCT TGAAATTGGT GGAAAAATAC CTGTCTGGGA TGGGGCTCAA   42660
42661   TAATCTGCAG CTGTATTAGG AAATGCAAGT AGTTTTGATG TGGGTGGTTT CAAGACATAT   42720
42721   TTGGAAAATG TGAGGGAAAT GTGTATGTGC ATTTGCTGAG CGGGGGACTG GTGAAGGATC   42780
42781   ACCGATCCAT TTATTCCTAA TGCTCATCTC AGCTTTTTAT TGTGCCGAGT ACCTTGATAA   42840
42841   GGCTTGGGTT ATTTTATGAG CGTTTATATA TAAATTGATA GTGTCCATCA GATCATGTAT   42900
42901   ATTTAGAGGC ATGCTCCTAC TTTGAGTAAA TGGAAAGCTT TAGAGATATA CACTAAATAA   42960
42961   ACATCAGTTA CTAATTAAAA ATTCCCTCCT CACTTTACCA AAGGACCCAC CATGGGTTCC   43020
43021   ATTAAATGTC TATTTATGGT TTGTTTTGAC AAAGACTTTT CCAAGAACAC CTCTGTTCTG   43080
43081   TAAAGCAGAA GAGCTGTGTA GATGTTCCAG AGTCGCTTGG TGTAAATTTG GTTCTGATTT   43140
43141   GTGCCGTGAA GCCCAATAAC AAACTGGAGG CACACATTTC AAAGCCAGTG GTAAGAGTTT   43200
43201   GAGTAGTGAT CATCTATTCC TGAACATAAA GTCTGGAGCC TTCTGGAATC CATAAAAATG   43260
43261   GAATGATTTG TTCCTTTCCC CTCTAACCAA ATTTTATTCA TACCTGGCTA TAAATAGCTT   43320
43321   CTGTTTTGAG TTTTCACTGG TCAGACCCTG CTGTTTTAGT GCCATCCTGT TAGCTTCCTT   43380
43381   GAACAAGGTA ATGCCACCTA ACATGTTTTT TCAGACTTCC AGGACAATGA TCAGGGGAC   43440
43441   TTCTCTATGC CACACTGGGA GGTGTGAAGG TGTAGGCTTT AGGGCAACCC CTCTGAGAAG   43500
43501   GGGTGGCAGG TGGAGGAGCC CATTGATCCT TTCTATCAGG GATGGATTTG CTTTCTGTGG   43560
43561   GTGTCACCTT CAGGGGCCTG TGTTCCCACT CATCACAGGA GCTCATATTT ACTCAGTGGG   43620
```

Figure 1 – page 29

```
43621  GCCAGAGTGT TCTTCATACA TGGTGATTTT ACTCCTCACC ATAACCTCCG TGGTGCGTGC  43680
43681  TAACATGACC ACCATTTTGC AGATGAGAAC ATGGAGGCTT GCAGGGGAGG TAAGTTGCCC  43740
43741  CAGGTTCCAT GCTGAATCAG AGGTCAAGCT CAGCACACAG CACAGGACCA AGTCTGCTGG  43800
43801  TTCCCAAGCT CACATCCTTA CCTACAACTC TGAATCACCC CACAGCAGAG TCAACAAGCT  43860
43861  GGCCTGGCAT GTGAAGAAGC AAGCCTGGGT GTCTCCTGGC TGCCAGTGCC ATCCCTGCCC  43920
43921  CGGGACCCTA ATCCACAGTT TGATTCTGGT CCTTTTGCCC TCTGTCCCTC ACCAGAACCC  43980
43981  TGATATTTCC AGATGAAAAC ACGAGTATAG CTTATTTCCA CAACTCACCT GGGCCCAGCA  44040
44041  ATCAAGATCT ATAGCTATAG GGAAGTATTG AGTTGATTAT GAGTTATATA GGTCAAAATG  44100
44101  AGTAGCTTGC TTGATTGAAG CAGGTAATTC GTGCCATACT TTTCTCTTTG GAAGACCTG   44160
44161  TACCAACAAT AACCTCTGCT AAACACTTTC GCTTTTTTAA ATTTGCAGGT ACTTTTTGG   44220
44221  GGCTGTCTTT GGCTGCCTGT CTGTTGAGAG TTTGTTTTCT TTACAGTCCA TCTGATTTAC  44280
44281  AGTCCCTCCG GGTTGATTTG TCTCATTTGG GAATGAGAAA TTTTATTTTA ATGCATTAAG  44340
44341  TAATAGTGTT GAGTGGCCAA CAAATGTGAA GTTTGAAAAG CTCAAATGAA AAAAAAGTG   44400
44401  TGATAGAAAC ACAGAGTTGG GGGCCGGGTG CAGTGGCTCA CACCTGTATT TCCGGCACTG  44460
44461  TGGGAGGCCA AGACAGGAGG ATCCCTTGAG CTCAGGAGTT TGAGACCCCT GGGCAACATG  44520
44521  GCAAGACCCC AAGACCCCAT CTCTACAAAA AAAATGTAAA AATCAGCCAG GGGTAATCCC  44580
44581  AGCTACTTGG GAGGCTGAGG TGGAAGGATT GCTTGAGCCC GGGAGGTTGA GGCTGCAGTG  44640
44641  AGCTGTGATC GATCTACTGG ACTCCAGCCT GAGTGACAGA GCAAGACCCT ATCTAAAAAA  44700
44701  AAAAAAAAAA AAAAAAAAG AAGAAGAAGA ACACAGGTTG GAATTTGAGG GGGCCTGTTA   44760
44761  AATAGGATGC TCTTTCCTGC CTTAGTTTTG AATTAATTGA GAAGATAAAA TAATAAGGCA  44820
44821  TGGAGATTAG AGCATCCCCT TTCTTTTTTT CTTTTTCTTT TCTTTTTTCT TTTTTCTTT   44880
44881  TTTACTTTTT GCTCTTCTTG GCCAGGCTGG AGTGCAATGG CACAATCTTG GCTCACCACA  44940
44941  ACCTCCGCCT CGCGGGTTCA AGCAATTCTC TTGCCTCAGC TTCCCAGTA  GCTGGGGTTA   45000
45001  CAGCCACGTG CCATGATGCC CAGCTAATTT TGTATTTTCA GTAGAGACGG GGTTTCTCCA  45060
45061  TGTTGGTCAG GCTGGTCTCG AACTCCCCAC CTCAGGTAAT CCACCCGCCT CGGCCTCCCA  45120
45121  AAGTGCTGGG AATACAGGCA TGAGCCACCA GGCCCGGCAG CATCCCCTTT CTTATTGATA  45180
45181  AAGCAGATCT TGGAGAATGG GAGATCCTGA GCGGGGTTCC TAATGCTAGC CTTCAACATC  45240
```

Figure 1 – page 30

```
45241  AGGCTGAGGC TCACCTTGTC TTCAAGTAAT GGGCAGTGCT GGCCTGAAGG GGAGCCTCCT  45300

45301  CTGTCCAGGG CTCAGCTTAT CCTTGGAAGG CTTAGCACAT TGAGGAGCTG CTCCAGGCTA  45360

45361  AGAGGGAGGG ACTGGGGTAC TCTGTAGAGG TTGTTCTTCC AGTTTCTTCA ATCAGATGAG  45420

45421  CCACACTGTC ACTCTAGTGT TGAAAGGAGG GAAGGGACAG AGGTGGCCAG GAGTGTGACC  45480

[I5F(-148)]
45481  CTAAAAGAGG CAGAGGAGAC CTCAGAGAAA GAGAAGAAGC ATTCTCCTAA CCAGAGGGAG  45540

45541  AAGGAGAGAG GCCTCAGTTC TCCCTCTCTG GAATTAATT TGAGATTTAC ATTTAGTGTC  45600

GSTO2 Exon 6
                                                                       157
45601  TATAAACATG TCAGCAGATA TATAAACTTA TTTGCTTTTG CTTTGTTTCC ATTTTTAGAT  45660
                                                                       I 158 159 160 161 162 163   164 165 166 167 168 169 170 171 172 173   174 175 176 177
45661  TCTTGAGTAT CAGAACACCA CCTTCTTTGG TGGAACCTGT ATATCCATGA TTGATTACCT  45720
        L   E   Y   Q   N   T   T   F   F   G   T   C   I   S   M   I   D   Y   L 178 179 180 181 182 183   184 185 186 187 188 189 190 191 192
45721  CCTCTGGCCC TGGTTTGAGC GGCTGGATGT GTATGGGATA CTGGAGTAAG ACATTTGACA  45780
        L   W   P   W   F   E   R   L   D   V   Y   G   I   L   D (SEQ ID NO:6)

45781  TTGTGGTGTT AAATTCCCGG AGTCACACTG AGTAACAATG GTTAAGATGG TCTGCATGCC  45840

[I6R115]
45841  CCCTGTAGAC ATGTTCAGG ATGTCTGTGA AGTGAATCAG GTTTCTAAAC CGCAGTGTGT  45900

45901  GCTTCCTTGT TAAAAACATA TGTGCTTTTC CACTGCTAAC TTCAGACCCA CACTTTGCCC  45960

45961  GCATTTCTGC AGATCAGACC CCTAGCCCAG GAGCCTCCCG CAGACTTCAG AGCCTGCTGT  46020

46021  CCTCACCAGC GCCCCACAT GGCCGGTCTG AGAGCAAGTG GAGAGTCACA GTCACAGTCA  46080

46081  CAGTGCCCAA CGCCTCCACC TGGTCCTGAC GGGTCCCCAG GGACACCAT ATAACCTTAG  46140

46141  TCATGTCTCA TTGCCCGGAG GAATCTTCCC CCAGATAGGA ATAACCTTAT AAAAAGATT  46200

46201  TGTGTAGTAA TATATGCTTG ATATTGGAAC ATACAAACAA ATGGCAGTG ACACACTATG  46260

46261  GAAGTATGGA AGTGCAGGGA CATTAAAGGA GAAGAAATAG CTGTGTAGGC TCCTGGGCAG  46320

46321  AGCAGTGCTG TGTTACTTCA AGCTCAGTG AAGCTGGACG TGTGCGGACG TCCACCCTAA  46380

46381  TCCAAGCCAC CCTCATGGTG GGTGCTGGAC ATTTCTGGCA CTTGGAAATC CGGCCCTGCT  46440

46441  GAAGCAGAAC TGTGTCTGCA CCTTCATAAC CCGTGGGCTG GAGCCCAACC AGCCACTGTC  46500

46501  TCCTGCACTT CCGACTTCAG CTCTCTTTGT CAGGATATTT AAAACTCAAT ATCAAACATA  46560

46561  AAATTTACAA AAGGCTGTAT CCTCTGAAGA CAGAGCATGG AGTCACAGGT TAGGAAACCT  46620
```

Figure 1 – page 31

```
46621  CACTTCTAGT CCTGGATTCC CGACAACCCA TTCATATTAT CTTCAGCTTA TTGCTTTATA  46680

46681  AACCCCAGAA CTAAATATCC TGGTTGAGCT TTGAAAGAGC CCTGTCGGCT CCATGACTTC  46740

46741  AAGGTTTCAT CCTTGTTTTA TTCATTTAAA AAATGTTTTA GAAATTATTT GTCTTTATTT  46800

46801  TTTTATATCT CCTAAAGTAA AATCTGAGAA TGACCCAAGA ATATTTGTTT CAGAGGGTTG  46860

46861  TCTTTTTGTT GGCAAGCAGT GAAGCACATG TAAGTTTCTC AAGCTTTAGA ATATATATAT  46920

46921  ATTAAAAAAC AAAACAAAAA AAATGAAGCA CAGACATGTT ATTTTCCCAG AGCCATCAGT  46980

46981  CCAAAGTATT TCACTGTATT ATTAGAAGCA ACAACTTCTA AACATTCAAC TATTCCAAAA  47040

47041  ATAAGATTTT CCTCCAGTAA GTTATCATTC TCACTTGATA ATAAGATAAC TAAGATAACT  47100
                      I6F(-97)
47101  TCCCAAATAA ACTCATTCTT CATATCTTGC AAATCTAAAA AGCAACGTGC ATCCCTTTC   47160
                                                              GSTO2 Exon 7
                                  [I6F(-15)]              193 194 195 196
47161  CTGATGCCTA CCCCTGCACT GTGCTGACGC TTCTTTCCTG TCTTGCAGCT GTGTGAGCCA  47220
                                                              C   V   S   H 197 198 199 200 201 202  203 204 205 206 207 208 209  210 211 212 213 214 215 216
47221  CACGCCAGCC CTGCGGCTCT GGATATCAGC CATGAAGTGG GACCCACAG TCTGTGCTCT    47280
        T   P   A   L   R   L   W   I   S   A   M   K   W   D   P   T   V   C   A   L 217 218 219 220 221 222  223 224 225 226 227 228 229  230 231 232 233 234 235 236
47281  TCTCATGGAT AAGAGCATTT TCCAGGGCTT CTTGAATCTC TATTTTCAGA ACAACCCTAA  47340
        L   M   D   K   S   I   F   Q   G   F   L   N   L   Y   F   Q   N   N   P   N 237 238 239 240 241 242  243                      [3'UTR R775]
47341  TGCCTTTGAC TTTGGGCTGT GCTGAGTCTC ACTGTCCACC CCTTCGCTGT CCAGAATTCC  47400
        A   F   D   F   G   L   C  (SEQ ID NO:7)

47401  CCAGCTTGTT GGGAGTCTAC GTCACGGCTT GTCTTGGGAA CCAATCCGTC TCTCTTTCTT  47460

47461  TTCTTTGAAG TTCCCAATAA AATGAAAACA GGAAATGTAT TCTTCTGATA ATCATTTGTC  47520

47521  TGACTCCTCT AGCCTGTAGC TGCTGCTACT GCTGCTTTTT TTTCCTTTTT TTTTTGAGG   47580

47581  CAAGATCTTG CTTCGTTACT CAGGCTGGAG TGCAGTGGGA CAGTCGGCTC ACTGCAGCCT  47640

47641  TGAACTCCTG GGCTCAGTTG ATTCTCCCGC CTCAGCCTCC TGAGAAGCTA GGACTACAGG  47700

47701  TATGTGTCAC CACGCCCAGC TAATTTTTAA AAAAATGTTG TTGAGACAGG GTCTCACTAT  47760

47761  GTTGCTCAGG CTGGTCTCCA TCTCCTGGCC GCAAGCCATC CACCCAACTT GGTCTCCAAA  47820
                                                        [3'FR F(1218)]
47821  GTGTTGAGAT TACAGGCATG AGCCACCTGG CCTGCCTAGC CTGTAGCTTC TAACTATTTT  47880
```

Figure 1 – page 32

```
                                      [3'FR R1228]
47881   CTAGAAAGTG CCTGGTGCTA ATGTCAGAGC ACATTTGGG AGCCTGTGTG CCTCCTAACT   47940
47941   CCTTGGCCTT CAGCCTAGTT TGATCTCCAG ATTATTGGTG CAGATGCTGA TGCTGAGGTT   48000
48001   CAGGGTCAAC CTATGACTGA TGCTTGTCAC TACAGAATGG CACCCTCCAA AGACCTCCCT   48060
48061   GGTGAAAGCT TAAGAAGAGG GAGAAGGAAG AAGAAAACAC TCCAAACCTA AATACCTTCC   48120
48121   ATTTGGCAAA TGAATGTCGC TGTCCACGTG GCGAGTATG  AGTGTAATTC TCCAAACTTT   48180
48181   GGCCATGGGC CTGGAGACAC CGAGGGTCTT GTGACTGGAA AGAATTCCAA AGCAGGAAAT   48240
48241   GAAACACCGG TTTATCACCC AGGACTAACT ACGTCAGAAT TTCACTGGTG CTGTCAGGGC   48300
48301   TCAGGATGTC TCACAAAATG TTCTATAGCC GGCATCCTGC CTTAAAAAAA TACACACGCC   48360
48361   CCAAACCCAG CCACAAGCAA AGGTCATTCC GTTGGATTTG CGTCACACTC TCTTCCAATT   48420
                                                          [3'FR R1855]
48421   CATCTCAACA AATGCCTCTG GTTGCCTGTT GTGTACCAAG CCCAGGGGCA CACTGGGGAT   48480
48481   AAAGTTGAAA AAGACATTGG CTCTGTCCCT GGGAGCCCCC ATCTCTCCAC TTATCTTGGT   48540
48541   TGAGGTTTTA AACCTAGCGC TTTGGAGCTG CTTGTCTGTT GTAGGGATGC TTGTCTCTGA   48600
48601   TGTGGCCCCT CTGCCAGCTT CGCCAGGCAG TACCACCCCA CTGAAGACAG CAAAGAGCTG   48660
48661   AGGATGGCTG GTGCCAACAG GTCCCTTGGG CTGGGAGCAT CTACTGCCTG CACTATGGGA   48720
48721   GGGGGACCAA GTTTGTCCAA TGCTGTTTCA TCTCAGTGTC TGAGGATCAG CCTGTGATCA   48780
48781   TTTCAGCTTT GCTCATGCTG GATCCTTTCC CATCCTCCTA GCTGTGCTGA GACACCAGGC   48840
48841   AGCAACAGGA GCGATGTTTT GCCTTGTCTG TGCTCCCTAA GGAGCTGTCT GCCACCTCTG   48900
48901   CCTCTGAGAC AGCCCAAATC AGCCCTCCTC TCTCCCCACG TCTCAGTCTG GCCCTGCCAT   48960
48961   CTGCTGGCTC TGGGTATATT TTGACCCATG TAAATAGTTA CCAGGTGTTA CTCTGTGCCA   49020
49021   GCTGGACAGA AACAAGCCTG CTTGGTGAGG TGGCCAGAAC TTCCAGAAGA GGCAGCGCAT   49080
49081   GACAGGGGCA GTCTGCCGCA CCATCTGCTC CGGATGTGGA GCCCTGTTGC CATGGCACCC   49140
49141   TAGTTAATGC TGAGTGAGGT CTGTGAATCA CCGTTTTCCT GGGATCTTTG CTCCAAGAAG   49200
49201   AGGGAATCT  TCTCCTGTGG CCTCTCATAG GACTTAGGAG ATTGATCAGC CTTTTGCCGG   49260
49261   TACAAATCCT GCATGCTAGT GAGTGCTTGT CATAAGACCA AAGTTACCAC TGATGCAACA   49320
49321   GGAAATGGCA TGCCTCTGGC TCACCAAAAT GAAGGTGTTC TCTTTTGGGG CTCCGCACAC   49380
49381   TAATTTAGAA AGCTTGAAGA ACCAGGAATT ATAGAATGGA GAAAGCACT  CATGGGGGAG   49440
```

Figure 1 – page 33

```
49441  GTTTGCAGCC TGGTGGCCTA TAGCCCAGTT TGGGATTTGA GTGCCTCTTG GCCAGGCATG  49500
49501  CTCCCTGCTG TTTACCAGGG TCCTGGTCAC CT    49560
```

Figure 2

```
1     ATGTCTGGGG ATGCGACCAG GACCCTGGGG AAAGGAAGCC AGCCCCCAGG GCCAGTCCCG    60
      M  S  G   D  A  T  R   T  L  G   K  G  S    Q  P  P  G   P  V  P

61    GAGGGGCTGA TCCGCATCTA CAGCATGAGG TTCTGCCCCT ATTCTCACAG GACCCGCCTC   120
      E  G  L   I  R  I  Y   S  M  R   F  C  P    Y  S  H  R   T  R  L

121   GTCCTCAAGG CCAAAGACAT CAGACATGAA GTGGTCAACA TTAACCTGAG AAACAAGCCT   180
      V  L  K   A  K  D  I   R  H  E   V  V  N    I  N  L  R   N  K  P

181   GAATGGTACT ATACAAAGCA CCCTTTTGGC CACATTCCTG TCCTGGAGAC CAGCCAATGT   240
      E  W  Y   Y  T  K  H   P  F  G   H  I  P    V  L  E  T   S  Q  C

241   CAACTGATCT ATGAATCTGT TATTGCTTGT GAGTACCTGG ATGATGCTTA TCCAGGAAGG   300
      Q  L  I   Y  E  S  V   I  A  C   E  Y  L    D  D  A  Y   P  G  R

301   AAGCTGTTTC CATATGACCC TTATGAACGA GCTCGCCAAA AGATGTTATT GGAGCTATTT   360
      K  L  F   P  Y  D  P   Y  E  R   A  R  Q    K  M  L  L   E  L  F

361   TGTAAGGTCC CACATTTGAC CAAGGAGTGC CTGGTAGCGT TGAGATGTGG GAGAGAATGC   420
      C  K  V   P  H  L  T   K  E  C   L  V  A    L  R  C  G   R  E  C

421   ACTAATCTGA AGGCAGCCCT GCGTCAGGAA TTCAGCAACC TGGAAGAGAT TCTTGAGTAT   480
      T  N  L   K  A  A  L   R  Q  E   F  S  N    L  E  E  I   L  E  Y

481   CAGAACACCA CCTTCTTTGG TGGAACCTGT ATATCCATGA TTGATTACCT CCTCTGGCCC   540
      Q  N  T   T  F  F  G   G  T  C   I  S  M    I  D  Y  L   L  W  P

541   TGGTTTGAGC GGCTGGATGT GTATGGGATA CTGGACTGTG TGAGCCACAC GCCAGCCCTG   600
      W  F  E   R  L  D  V   Y  G  I   L  D  C    V  S  H  T   P  A  L

601   CGGCTCTGGA TATCAGCCAT GAAGTGGGAC CCACAGTCT GTGCTCTTCT CATGGATAAG    660
      R  L  W   I  S  A  M   K  W  D   P  T  V    C  A  L  L   M  D  K

661   AGCATTTTCC AGGGCTTCTT GAATCTCTAT TTTCAGAACA ACCCTAATGC CTTTGACTTT   720
      S  I  F   Q  G  F  L   N  L  Y   F  Q  N    N  P  N  A   F  D  F

721   GGGCTGTGCT GA     732 (SEQ ID NO:8)
      G  L  C  (SEQ ID NO:9)
```

GLUTATHIONE S-TRANSFERASE SEQUENCE VARIANTS

CROSS-REFERENCE TO RELATED APPLICATIONS

This application is a divisional of U.S. patent application Ser. No. 11/482,525, filed on Jul. 7, 2006, now U.S. Pat. No. 7,390,894, which claims benefit of priority from U.S. Provisional Patent Application Ser. No. 60/697,128, filed on Jul. 7, 2005, the entire contents of which are hereby incorporated by reference.

STATEMENT AS TO FEDERALLY SPONSORED RESEARCH

The invention was made with government support under grant nos. GM28157, GM35720, and GM61388, awarded by the National Institutes of Health. The government has certain rights in the invention.

TECHNICAL FIELD

This document relates to GSTO2 nucleic acid and amino acid sequence variants.

BACKGROUND

The Omega class of glutathione transferases (GSTs) have been identified in organisms including human, mouse, rat, pig, *Caenorhabditis elegans*, and *Drosophila melanogaster*. These GSTs, which include glutathione S-transferase omega 2 (GSTO2) have poor activity with common GST substrates, but exhibit novel glutathione-dependent thioltransferase, dehydroascorbate reductase, and monomethylarsonate reductase activities, and also modulate calcium release by ryanodine receptors. The GSTO2 gene contains seven exons, the first of which does not contain GSTO2 coding sequence. The GSTO2 gene is separated from the GSTO1 gene by 7.5 kb on chromosome 10q24.3. GSTO2 is expressed at high levels in the testes, and also is expressed in liver, kidney, skeletal muscle, heart, and lung, with low level expression in the cervix, ovary, and prostate. Substrates for GSTO2 include monomethylarsonic acid (MMV), which is reduced from the $^+$V form to the $^+$III form, as well as dehydroascorbate (DHA) and glutathione (GSH), which can be reacted to give ascorbate and glutathione disulfate.

SUMMARY

This document is based on the discovery of sequence variants that occur in both coding and non-coding regions of GSTO2 nucleic acids. Certain GSTO2 nucleotide sequence variants encode GSTO2 enzymes that are associated with individual differences in enzymatic activity. Other GSTO2 sequence variants in non-coding regions of the GSTO2 nucleic acid may alter regulation of transcription and/or splicing of the GSTO2 nucleic acid. Discovery of these sequence variants allows individual differences in the metabolism of drugs and other xenobiotics in humans to be assessed such that particular treatment regimens can be tailored to an individual based on the presence or absence of one or more sequence variants. For example, the presence of absence of a particular variant may indicate an individual's ability to metabolize arsenic, which is a contaminant in drinking water, and which can cause skin, bladder, kidney, liver, and lung cancer in individuals subjected to chronic arsenic exposure. The presence of absence of a particular variant also may indicate an individual's ability to metabolize arsenic trioxide, an agent that can be used to treat acute promyelocytic leukemia. Identification of GSTO2 sequence variants also may allow predisposition to cancer or conditions such as Alzheimer's or Parkinson's disease to be assessed in individuals.

In one aspect, this document features an isolated nucleic acid molecule consisting essentially of a variant GSTO2 nucleic acid sequence, wherein the variant GSTO2 nucleic acid sequence is selected from the group consisting of: a) at least ten contiguous nucleotides of SEQ ID NO:8, wherein said sequence includes nucleotide 121, 389, or 472 of SEQ ID NO:5, with the proviso that the nucleotide at position 121 is adenine, the nucleotide at position 389 is adenine, or the nucleotide at position 472 is adenine; b) at least ten contiguous nucleotides of SEQ ID NO:1, wherein said sequence includes nucleotide 15569, 15811, 15918, 15984, 16006, 16016, 16041, 16403, 16477, 16801, 16851, 16945, or 16948 of SEQ ID NO:1, with the proviso that a guanine is inserted after the nucleotide at position 15569, the nucleotide at position 15811 is cytosine, the nucleotide at position 15918 is thymine, the nucleotide at position 15984 is guanine, the nucleotide at position 16006 is cytosine, the nucleotide at position 16016 is adenine, the nucleotide at position 16041 is thymine, the nucleotide at position 16403 is thymine, the nucleotide at position 16477 is adenine, the nucleotide at position 16801 is cytosine, a thymine is inserted after the nucleotide at position 16851, the nucleotide at position 16945 is thymine, or the nucleotide at position 16948 is guanine; c) at least ten contiguous nucleotides of SEQ ID NO:1, wherein said sequence includes nucleotide 16957, 17056, 17119, 17132, 17158, 17172, or 17348 of SEQ ID NO:1, with the proviso that the nucleotide at position 16957 is guanine, the nucleotide at position 17056 is adenine, the nucleotide at position 17119 is adenine, the nucleotide at position 17132 is cytosine, the nucleotide at position 17158 is adenine, the nucleotide at position 17172 is guanine, or the nucleotide at position 17348 is thymine; d) at least ten contiguous nucleotides of SEQ ID NO:1, wherein said sequence includes nucleotide 17402, 17502, 17659 and 17662, 17683, 17752, 17785, 17827, 19044, 19496, 21635, 22747, or 22754 of SEQ ID NO:1, with the proviso that the nucleotide at position 17402 is guanine, the nucleotide at position 17502 is thymine, the nucleotides at positions 17660 and 17661 are deleted, the nucleotide at position 17683 is cytosine, the nucleotide at position 17752 is thymine, the nucleotide at position 17785 is adenine, a thymine is inserted after the nucleotide at position 17827, the nucleotide at position 19044 is guanine, the nucleotide at position 19496 is guanine, the nucleotide at position 21635 is thymine, the nucleotide at position 22747 is adenine, or the nucleotide at position 22754 is adenine; e) at least ten contiguous nucleotides of SEQ ID NO:1, wherein said sequence includes nucleotide 23291, 26236, 27722, 47154, or 47188 of SEQ ID NO:1, with the proviso that the nucleotide at position 23291 is thymine, the nucleotide at position 26236 is thymine, the nucleotide at position 27722 is cytosine, the nucleotide at position 47154 is guanine, or the nucleotide at position 47188 is thymine; f) at least ten contiguous nucleotides of SEQ ID NO:1, wherein said sequence includes nucleotide 47713, 47876, 48248, 48282, or 48357 of SEQ ID NO:1, with the proviso that the nucleotide at position 47713 is thymine, the nucleotide at position 47876 is guanine, the nucleotide at position 48248 is thymine, the nucleotide at position 48282 is cytosine, or the nucleotide at position 48357 is thymine; and g) the complement of a), b), c), d), e), or f). The isolated nucleic acid can be from 10 to 100 nucleotides in length or from 20 to 50 nucleotides in length.

This document also features a vector comprising the nucleic acid molecule described herein. The nucleic acid molecule can be from 20 to 50 nucleotides in length.

In another aspect, this document features an isolated nucleic acid encoding a GSTO2 polypeptide, wherein the polypeptide contains a GSTO2 amino acid sequence variant relative to the amino acid sequence of SEQ ID NO:9, and wherein the amino acid sequence variant is at a residue selected from the group consisting of 41, 130, and 158. The amino acid sequence variant can be an isoleucine at residue 41, a tyrosine at residue 130, or an isoleucine at residue 158.

In another aspect, this document features an isolated GSTO2 polypeptide, wherein the polypeptide contains a GSTO2 amino acid sequence variant relative to the amino acid sequence of SEQ ID NO:9, and wherein the amino acid sequence variant is at a residue selected from the group consisting of 41, 130, and 158. The amino acid sequence variant can be an isoleucine at residue 41, a tyrosine at residue 130, or an isoleucine at residue 158.

In still another aspect, this document features an article of manufacture comprising a substrate, wherein the substrate comprises a population of isolated variant GSTO2 nucleic acid molecules as disclosed herein. The article of manufacture can comprise a plurality of discrete regions, wherein each region comprises a different population of isolated variant GSTO2 nucleic acid molecules, and wherein each population of molecules comprises a different GSTO2 nucleotide sequence variant.

This document also features a method for determining a GSTO2 genotype. The method can comprise: a) providing a nucleic acid sample from a subject, and b) screening the nucleic acid sample for one or more genetic markers in linkage disequilibrium with a GSTO2 allele. The GSTO2 allele can be selected from the group consisting of a G121A allele, a G389A allele, an A424G allele, or a C472A allele.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1 shows the nucleotide sequence of the reference GSTO1 and GSTO2 genes (SEQ ID NO:1), and the amino acid sequence of the reference GSTO2 polypeptide (SEQ ID NOs:2, 3, 4, 5, 6, and 7). Exons are depicted in bold type and non-coding sequences are in regular type. Positions of single nucleotide polymorphisms (SNPs) are circled, as are the positions of amino acid changes that result from the SNPs. Primers are underlined, and start and stop codons are double-underlined. Exon 1 contains nucleotides 16954 to 17312 of SEQ ID NO:1. Intron 1 contains nucleotides 17313 to 22765 of SEQ ID NO:1. Exon 2 contains nucleotides 22766 to 23051 of SEQ ID NO:1. The translation initiation codon begins at nucleotide 22997 of SEQ ID NO:1, within exon 2. Intron 2 contains nucleotides 23052 to 23306 of SEQ ID NO:1. Exon 3 contains nucleotides 23307 to 23415 of SEQ ID NO:1. Intron 3 contains nucleotides 23416 to 25974 of SEQ ID NO:1. Exon 4 contains nucleotides 25975 to 26197 of SEQ ID NO:1. Intron 4 contains nucleotides 26198 to 27450 of SEQ ID NO:1. Exon 5 contains nucleotides 27451 to 27552 of SEQ ID NO:1. Intron 5 contains nucleotides 27553 to 45658 of SEQ ID NO:1. Exon 6 contains nucleotides 45659 to 45765 of SEQ ID NO:1. Intron 6 contains nucleotides 45766 to 47208 of SEQ ID NO:1. Exon 7 contains nucleotides 47209 to 47496 of SEQ ID NO:1.

FIG. 2 shows the open reading frame (SEQ ID NO:8) of the reference GSTO2, and also shows the reference amino acid sequence (SEQ ID NO:9) of the encoded GSTO2. Positions of cSNPs are circled, as are the positions of amino acid changes that result from the cSNPs. Start and stop codons are double-underlined.

DETAILED DESCRIPTION

Figure 3:
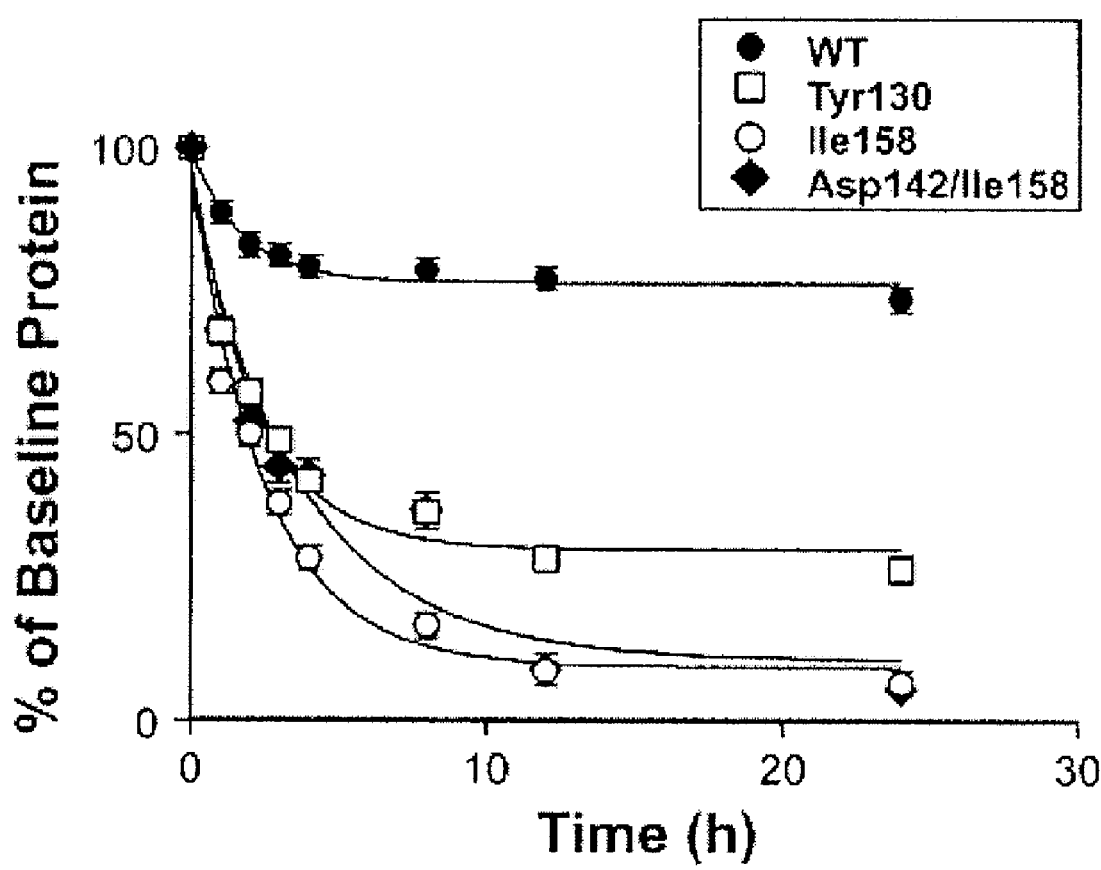
FIG. 3 is a graph plotting protein degradation data for the indicated GSTO2 allozymes.

This document features GSTO2 nucleotide and amino acid sequence variants. GSTO2 is thought to be a cytoplasmic enzyme that has glutathione transferase and glutathione dehydrogenase activity. For example, GSTO2 can catalyze the transfer of glutathione to an aliphatic, aromatic, or heterocyclic molecule, wherein the linkage is via a thiol group. GSTO2 also can catalyze the dehydrogenation of DHA, which can be reacted with GSH to give ascorbate and glutathione disulfate. Genetically-based variations in GSTO2 activity that lead to altered levels of GSTO2 or altered GSTO2 activity may be important in particular diseases or clinical conditions.

Nucleic Acid Molecules

Provided herein are isolated nucleic acids that include a GSTO2 nucleic acid sequence. The GSTO2 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-GSTO2 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids provided herein are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids can be in a sense or antisense orientation, can be complementary to the GSTO2 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in a GSTO2 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference GSTO2 nucleic acid sequence is provided in FIG. 1 (SEQ ID NO:1) and in GenBank (Accession No. NT_030059). The reference GSTO2 ORF is provided in FIG. 2 (SEQ ID NO:8), as is the corresponding reference GSTO2 amino acid sequence (SEQ ID NO:9). The mRNA and amino acid reference sequences also are found in GenBank (Accession No. NM_183239). The nucleic acid and amino acid reference sequences also are referred to herein as "wild type."

As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences can be designated as "−X" relative to the "A" in the translation initiation codon; positions of nucleotide sequence variants in the coding sequence and 3' untranslated sequence can be designated as "+X" or "X" relative to the "A" in the translation initiation codon. Nucleotide sequence variants that occur in introns can be designated as "+X" or "X" relative to the "G" in the splice donor site (GT) or as "−X" relative to the "G" in the splice acceptor site (AG).

In some embodiments, a GSTO2 nucleotide sequence variant encodes a GSTO2 polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-225 residues, or a full-length GSTO2 polypeptide). GSTO2 polypeptides may or may not have GSTO2 catalytic activity, or may have altered activity relative to the reference GSTO2 polypeptide. Polypeptides that do not have activity or have altered activity can be useful for diagnostic purposes (e.g., for producing antibodies having specific binding affinity for variant GSTO2 polypeptides).

Corresponding GSTO2 polypeptides, irrespective of length, that differ in amino acid sequence are herein referred to as allozymes. For example, a GSTO2 nucleic acid sequence that includes an adenine at position 121 relative to the adenine in the translation initiation codon (i.e., nucleotide 23393 of SEQ ID NO:1 or nucleotide 121 of SEQ ID NO:8) encodes a GSTO2 polypeptide having an isoleucine at amino acid residue 41. This polypeptide (Val41Ile) would be considered an allozyme with respect to the reference GSTO2 polypeptide that contains a valine at amino acid residue 41. Additional non-limiting examples of GSTO2 sequence variants that alter amino acid sequence include variants at nucleotides 389, 424, and 472 relative to the adenine in the translation initiation codon (i.e., positions 27473, 27508, and 45662, respectively, of SEQ ID NO:1, or positions 389, 424, and 472, respectively, of SEQ ID NO:8). For example, a GSTO2 nucleic acid molecule can include an adenine at nucleotide 389 and encode a GSTO2 polypeptide having a tyrosine at amino acid residue 130 in place of a cysteine residue (Cys130Tyr); a guanine at nucleotide 424 and encode a GSTO2 polypeptide having an aspartic acid at amino acid residue 142 in place of an asparagine residue (Asn142Asp), or an adenine at nucleotide 472 and encode a GSTO2 polypeptide having an isoleucine at amino acid 158 in place of a leucine residue (Leu158Ile).

GSTO2 allozymes as described above are encoded by a series of GSTO2 alleles. These alleles represent nucleic acid sequences containing sequence variants, typically multiple sequence variants, within coding and non-coding sequences. Representative examples of single nucleotide variants are described herein. Table 2 sets out a series of GSTO2 alleles that encode GSTO2. Some alleles are commonly observed, i.e., have allele frequencies >1%, such as the allele having a guanine at nucleotide 424 place of an adenine. The relatively large number of alleles and allozymes for GSTO2 indicates the potential complexity of GSTO2 pharmacogenetics. Such complexity emphasizes the need for determining single nucleotide variants, (i.e., single nucleotide polymorphisms, SNPs) as well as complete GSTO2 haplotypes (i.e., the set of alleles on one chromosome or a part of a chromosome) of patients.

Certain GSTO2 nucleotide sequence variants do not alter the amino acid sequence. Such variants, however, could alter regulation of transcription as well as mRNA stability. GSTO2 variants can occur in intron sequences, for example, within introns 1, 2, 4, 5, or 6. For example, nucleotide sequence variants in the first intron can include a guanine substitution at nucleotide 52 (i.e., nucleotide 17402 of SEQ ID NO:1), a thymine substitution at nucleotide 152 (i.e., nucleotide 17502 of SEQ ID NO:1), deletion of cytosine and guanine residues at nucleotides 310 and 311 (i.e., nucleotides 17660 and 17661 of SEQ ID NO:1), an adenine substitution at nucleotide 311 (i.e., nucleotide 17661 of SEQ ID NO:1), a cytosine substitution at nucleotide 333 (i.e., nucleotide 17683 of SEQ ID NO:1), a thymine substitution at nucleotide 402 (i.e., nucleotide 17752 of SEQ ID NO:1), a cytosine substitution at nucleotide 426 (i.e., nucleotide 17776 of SEQ ID NO:1), an adenine substitution at nucleotide 435 (i.e., nucleotide 17785 of SEQ ID NO:1), insertion of a thymine after nucleotide 477 (i.e., nucleotide 17827 of SEQ ID NO:1), a guanine substitution at nucleotide 1694 (i.e., nucleotide 19044 of SEQ ID NO:1), a guanine substitution at nucleotide 2003 (i.e., nucleotide 19353 of SEQ ID NO:1), a guanine substitution at nucleotide 2146 (i.e., nucleotide 19496 of SEQ ID NO:1), an adenine substitution at nucleotide 2168 (i.e., nucleotide 19518 of SEQ ID NO:1), a thymine substitution at nucleotide −1131 (i.e., nucleotide 21635 of SEQ ID NO:1), a guanine substitution at nucleotide −185 (i.e., nucleotide 22581 of SEQ ID NO:1), an adenine substitution at nucleotide −19 (i.e., nucleotide 22747 of SEQ ID NO:1), or an adenine substitution at nucleotide −12 (i.e., nucleotide 22754 of SEQ ID NO:1). Other examples of sequence variants within introns include a thymine substitution at nucleotide −16 of intron 2 (i.e., nucleotide 23291 of SEQ ID NO:1), a cytosine substitution at nucleotide 20 of intron 4 (i.e., nucleotide 26217 of SEQ ID NO:1), a thymine substitution at nucleotide 39 of intron 4 (i.e., nucleotide 26236 of SEQ ID NO:1), a cytosine substitution at nucleotide −38 of intron 4 (i.e., nucleotide 27413 of SEQ ID NO:1), a guanine substitution at nucleotide 74 of intron 5 (i.e., nucleotide 27626 of SEQ ID NO:1), a cytosine substitution at nucleotide 170 of intron 5 (i.e., nucleotide 27722 of SEQ ID NO:1), a guanine substitution at nucleotide −55 of intron 6 (i.e., nucleotide 47154 of SEQ ID NO:1), or a thymine substitution at nucleotide −21 of intron 6 (i.e., nucleotide 47188 of SEQ ID NO:1).

GSTO2 nucleotide sequence variants that do not change the amino acid sequence also can be within an exon or in 5' or 3' untranslated sequences. For example, a GSTO2 nucleotide sequence variant within exon 2 can be a guanine substitution at nucleotide −183 relative to the adenine in the translation initiation codon. Exon 7 sequence variants can include, for example, a thymine substitution at nucleotide 591 (i.e., nucleotide 47224 of SEQ ID NO:1 or nucleotide 591 of SEQ ID NO:8), or a thymine substitution at nucleotide 630 (i.e., nucleotide 47263 of SEQ ID NO:1 or nucleotide 630 of SEQ ID NO:8).

GSTO2 variants within the 5' FR (including the first exon) can be, for example, insertion of a guanine after nucleotide −2012 (i.e., nucleotide 15569 of SEQ ID NO:1) relative to the adenine in the translation initiation codon, a cytosine substitution at nucleotide −1785 (i.e., nucleotide 15797 of SEQ ID NO:1), a cytosine substitution at nucleotide −1771 (i.e., nucleotide 15811 of SEQ ID NO:1), a thymine substitution at nucleotide −1664 (i.e., nucleotide 15918 of SEQ ID NO:1), a guanine substitution at nucleotide −1598 (i.e., nucleotide 15984 of SEQ ID NO:1), a cytosine substitution at nucleotide −1576 (i.e., nucleotide 16006 of SEQ ID NO:1), an adenine substitution at nucleotide −1566 (i.e., nucleotide 16016 of SEQ ID NO:1), a thymine substitution at nucleotide −1541 (i.e., nucleotide 16041 of SEQ ID NO:1), an adenine substitution at nucleotide −1357 (i.e., nucleotide 16225 of SEQ ID NO:1), a cytosine substitution at nucleotide −1189 (i.e., nucleotide 16393 of SEQ ID NO:1), a thymine substitution at nucleotide −1179 (i.e., nucleotide 16403 of SEQ ID NO:1), an adenine substitution at nucleotide −1105 (i.e., nucleotide 16477 of SEQ ID NO:1), a guanine substitution at nucleotide −1102 (i.e., nucleotide 16480 of SEQ ID NO:1), a thymine substitution at nucleotide −1009 (i.e., nucleotide 16573 of SEQ ID NO:1), a cytosine substitution at nucleotide −781 (i.e., nucleotide 16801 of SEQ ID NO:1), insertion of a thymine after nucleotide −730 (i.e., nucleotide 16851 of SEQ ID NO:1), a thymine substitution at nucleotide −637 (i.e., nucleotide 16945 of SEQ ID NO:1), a guanine substitution at nucleotide −634 (i.e., nucleotide 16948 of SEQ ID NO:1), a guanine substitution at nucleotide −625 (i.e., nucleotide 16957 of SEQ ID NO:1), a guanine substitution at nucleotide −530 (i.e., nucleotide 17052 of SEQ ID NO:1), an adenine substitution at nucleotide −526 (i.e., nucleotide 17056 of SEQ ID NO:1), an adenine substitution at nucleotide −463 (i.e., nucleotide 17119 of SEQ ID NO:1), a cytosine substitution at nucleotide −450 (i.e., nucleotide 17132 of SEQ ID NO:1), an adenine substitution at nucleotide −424 (i.e., nucleotide 17158 of SEQ ID NO:1), a guanine substitution at nucleotide −410 (i.e., nucleotide 17172 of SEQ ID NO:1), a thymine substitution at nucleotide −293 (i.e., nucleotide 17289 of SEQ ID NO:1), or a thymine substitution at nucleotide −234 (i.e., nucleotide 17348 of SEQ ID NO:1).

GSTO2 variants within the 3' untranslated region can be, for example, a thymine substitution at nucleotide 1038 (i.e., nucleotide 47671 of SEQ ID NO:1) relative to the adenine in the translation initiation codon, a thymine substitution at nucleotide 1080 (i.e., nucleotide 47713 of SEQ ID NO:1), a guanine substitution at nucleotide 1243 (i.e., nucleotide 47876 of SEQ ID NO:1), a guanine substitution at nucleotide 1343 (i.e., nucleotide 47976 of SEQ ID NO:1), a thymine substitution at nucleotide 1615 (i.e., nucleotide 48248 of SEQ ID NO:1), a cytosine substitution at nucleotide 1649 (i.e., nucleotide 48282 of SEQ ID NO:1), or a thymine substitution at nucleotide 1724 (i.e., nucleotide 48357 of SEQ ID NO:1).

In some embodiments, a GSTO2 nucleic acid molecule can consist essentially of at least ten (e.g., at least 12, at least 15, at least 18, at least 20, or at least 25) contiguous nucleotides of an GSTO2 reference sequence (e.g., SEQ ID NO:1 or SEQ ID NO:8). Such nucleic acids can contain one or more variant positions, with the proviso that the nucleotides at those positions are variant nucleotides as disclosed herein in Table 2, for example. A GSTO2 nucleic acid "consisting essentially of" a particular sequence has the basic and novel characteristic that it can be used to distinguish, based upon hybridization, a nucleic acid having a sequence that contains a variant from a corresponding nucleic acid having a sequence that does not contain the variant (e.g., a wild type sequence). Such nucleic acid molecules can include additional sequences or labels (e.g., a tag or a fluorescent label as disclosed herein), provided that such additions do not affect the basic and novel characteristic of the nucleic acid molecules.

In some embodiments, a GSTO2 nucleic acid sequence can have at least 90% (e.g., 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity with a region of SEQ ID NO:1 or SEQ ID NO:8. The region of SEQ ID NO:1 or SEQ ID NO:8 is at least ten nucleotides in length (e.g., 10, 15, 20, 50, 60, 70, 75, 100, 150 or more nucleotides in length). For example, a nucleic acid can include a GSTO2 nucleic acid sequence with at least 90% identity to nucleotides 75 to 175, 350 to 450, 375 to 475, 425 to 525, 550 to 650, or 600 to 700 of SEQ ID NO:8. A variant GSTO2 nucleotide sequence can have an adenine at nucleotide 121, an adenine at nucleotide 389, an adenine at nucleotide 424, an adenine at nucleotide 472, a thymine at nucleotide 591, or a thymine at nucleotide 630, and combinations thereof, wherein the numbering of the positions is with respect to the numbering of SEQ ID NO:8.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S.

government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: –i is set to a file containing the first nucleic acid sequence to be compared (e.g., C:\seq1.txt); –j is set to a file containing the second nucleic acid sequence to be compared (e.g., C:\seq2.txt); –p is set to blastn; –o is set to any desired file name (e.g., C:\output.txt); –q is set to –1; –r is set to 2; and all other options are left at their default setting. The following command will generate an output file containing a comparison between two sequences: C:\Bl2seq –i c:\seq1.txt –j c:\seq2.txt –p blastn –o c:\output.txt –q –1 –r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 969 nucleotides from the target sequence aligned with a region of the sequence set forth in SEQ ID NO:1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing a GSTO2 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, the reference sequences depicted in FIG. 1 or 2 can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

GSTO2 Polypeptides

Isolated GSTO2 polypeptides provided herein include an amino acid sequence variant relative to the reference GSTO2 (SEQ ID NO:9, FIG. 2; GenBank Accession No. NM_183239). The term "isolated" with respect to a GSTO2 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

GSTO2 polypeptides can include variants at one or more of amino acid residues 41, 130, 142, and 158. In particular, an isoleucine residue can be substituted at position 41, a tyrosine residue at position 130, an aspartic acid residue at position 142, or an isoleucine residue at position 158. In some embodiments, activity of GSTO2 polypeptides is altered relative to the reference GSTO2. Certain GSTO2 allozymes can have reduced activity, while other allozymes can have activity that is comparable to the reference GSTO2. Other allozymes can have increased activity relative to the reference GSTO2. Activity of GSTO2 polypeptides can be assessed in vitro. For example, reduction of DHA catalyzed by bacterially expressed GSTO2 can be detected by monitoring an increase in absorbance at 265 nm. Alternatively, activity of GSTO2 polypeptides can be assessed in vivo (e.g., in COS cells).

Other biochemical properties of allozymes, such as apparent $K_m$ values, also can be altered relative to the reference GSTO2. Apparent $K_m$ values can be calculated using, for example, the method of Wilkinson with a computer program written by Cleland. Wilkinson (1961) *Biochem. J.* 80:324-332; and Cleland (1963) *Nature* 198:463-365.

Isolated polypeptides can be obtained, for example, by extraction from a natural source (e.g., testes, liver, kidney, or skeletal muscle), chemical synthesis, or by recombinant production in a host cell. To recombinantly produce GSTO2 polypeptides, a nucleic acid encoding a GSTO2 nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to a GSTO2 nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of *Escherichia coli* can be used to express GSTO2 variant polypeptides. For example, BL-21 cells can be transformed with a pGEX vector containing a GSTO2 nucleic acid sequence. The transformed bacteria can be grown exponentially and then stimulated with isopropylthiogalactopyranoside (IPTG) prior to harvesting. In general, the GSTO2-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed GSTO2 polypeptide can be released from the GST moiety.

In eukaryotic host cells, a number of viral-based expression systems can be utilized to express GSTO2 variant polypeptides. A nucleic acid encoding a polypeptide can be cloned into, for example, a baculoviral vector such as pBlue-Bac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides can be identified by standard methodology. Alternatively, a nucleic acid encoding a polypeptide can be introduced into a SV40, retroviral, or vaccinia based viral vector and used to infect suitable host cells.

Eukaryotic cell lines that stably express GSTO2 variant polypeptides can be produced using expression vectors with the appropriate control elements and a selectable marker. For example, the eukaryotic expression vector pCR3.1 (Invitrogen, San Diego, Calif.) and p91023(B) (see Wong et al. (1985) *Science* 228:810-815) or modified derivatives thereof are suitable for expression of GSTO2 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pCR3.1, pcDNA3.1 (Invitrogen), or pcDNA4/HisMax TOPO (Promega) and then transcribed and translated in vitro using wheat germ extract or rabbit reticulocyte lysate.

GSTO2 variant polypeptides can be purified by known chromatographic methods including ion exchange and gel filtration chromatography. See, for example, Caine et al. (1996) *Protein Expr. Purif* 8:159-166. GSTO2 polypeptides can be "engineered" to contain a tag sequence describe herein that allows the polypeptide to be purified (e.g., captured onto an affinity matrix). Immunoaffinity chromatography also can be used to purify GSTO2 polypeptides.

Non-Human Mammals

Also featured herein are non-human mammals that include GSTO2 nucleic acids as described herein, as well as progeny and cells of such non-human mammals. Non-human mammals include, for example, rodents such as rats, guinea pigs, and mice, and farm animals such as pigs, sheep, goats, horses, and cattle. Non-human mammals can express a GSTO2 variant nucleic acid in addition to an endogenous GSTO2 (e.g., a transgenic non-human that includes a GSTO2 nucleic acid randomly integrated into the genome of the non-human mammal). Alternatively, an endogenous GSTO2 nucleic acid can be replaced with a GSTO2 variant nucleic acid by homologous recombination. See, Shastry (1998) *Mol. Cell. Biochem.* 181:163-179, for a review of gene targeting technology.

In one embodiment, non-human mammals are produced that lack an endogenous GSTO2 nucleic acid (i.e., a knockout), and then a GSTO2 variant nucleic acid as provided herein is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous GSTO2 nucleic acid. That is, cultured ES cells can be transformed with a knockout construct and cells selected in which the GSTO2 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning A Laboratory Manual*, second edition, Cold Spring Harbor Press, Plainview; NY, 1989.

To generate a knockout animal, ES cells having at least one inactivated GSTO2 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated GSTO2 allele. If the original ES cell was heterozygous for the inactivated GSTO2 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the GSTO2 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals. For example, fetal fibroblasts can be genetically modified such that they contain an inactivated endogenous GSTO2 gene and express a GSTO2 nucleic acid, and then fused with enucleated oocytes. After activation of the oocytes, the eggs are cultured to the blastocyst stage, and implanted into a recipient. See, Cibelli et al. (1998) *Science* 280:1256-1258. Adult somatic cells, including, for example, cumulus cells and mammary cells, can be used to produce animals such as mice and sheep, respectively. See, for example, Wakayama et al. (1998) *Nature* 394:369-374; and Wilmut et al. (1997) *Nature* 385:810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al., supra.

Non-human mammals such as mice can be used, for example, to screen toxicity of compounds that are substrates for GSTO2, drugs that alter GSTO2 activity, or for carcinogenesis. For example, GSTO2 activity or toxicity can be assessed in a first group of such non-human mammals in the presence of a compound, and compared with GSTO2 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting GSTO2 Sequence Variants

GSTO2 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC, Underhill et al. (1997) *Genome Res.* 7:996-1005), infrared matrix-assisted laser desorption/ionization (IR-MALDI) mass spectrometry (WO 99/57318), and combinations of such methods.

Genomic DNA generally is used in the analysis of GSTO2 nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the GSTO2 gene can be amplified then directly sequenced. Dye primer sequencing can be used to increase the accuracy of detecting heterozygous samples.

Nucleic acid molecules provided herein can be used to detect variant GSTO2 sequences. For example, allele specific hybridization also can be used to detect sequence variants, including complete haplotypes of a subject (e.g., a mammal such as a human). See, Stoneking et al. (1991) *Am. J. Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For GSTO2 sequence variants that do not alter a common restriction site, mutagenic primers can be designed that introduce a restriction site when the variant allele is present or when the wild type allele is present. A portion of GSTO2 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of GSTO2 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) *Genome* 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, GSTO2 variants can be detected by antibodies that have specific binding affinity for variant GSTO2 polypeptides. Variant GSTO2 polypeptides can be produced in various ways, including recombinantly, as discussed above. Host animals such as rabbits, chickens, mice, guinea pigs, and rats can be immunized by injection of a GSTO2 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a GSTO2 variant polypeptide and standard hybridoma technology. In particular, monoclonal antibodies can be obtained by any technique that provides for the production of antibody molecules by continuous cell lines in culture such as described by Kohler et al. (1975) Nature 256:495, the human B-cell hybridoma technique (Kosbor et al. (1983) *Immunology Today* 4:72; Cote et al. (1983) *Proc. Natl. Acad. Sci. USA* 80:2026), and the EBV-hybridoma technique (Cole et al., *Monoclonal Antibodies and Cancer Therapy*, Alan R. Liss, Inc., pp. 77-96 (1983). Such antibodies can be of any immunoglobulin class including IgG, IgM, IgE, IgA, IgD and any subclass thereof. A hybridoma producing monoclonal antibodies can be cultivated in vitro or in vivo.

Antibody fragments that have specific binding affinity for a GSTO2 variant polypeptide can be generated using known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246:1275 (1989). Once produced, antibodies or fragments thereof are tested for recognition of GSTO2 variant polypeptides by standard immunoassay methods including ELISA techniques, radioimmunoassays and Western blotting. See, *Short Protocols in Molecular Biology*, Chapter 11, Green Publishing Associates and John Wiley & Sons, edited by Ausubel et al., 1992.

Methods

As a result of the present disclosure, it is possible to determine GSH transferase status of a subject (e.g., a mammal such as a human). "GSH transferase status" refers to the ability of a subject to transfer a glutathione group to a substrate. GSH transferase status of a subject can be determined by, for example, measuring the level of GSTO2 activity in the subject using, for example, the methods described herein. Alternatively, GSH transferase status can be evaluated by determining whether a GSH transferase nucleic acid sequence (e.g., a GSTO2 nucleic acid sequence) of a subject contains one or more variants (e.g., one or more variants that are correlated with increased or decreased GSH transferase activity). A variant that results in decreased or increased GSTO2 activity, for example, can be said to result in "reduced" or "enhanced" GSH transferase status, respectively. In some embodiments, the variant profile of a subject can be used to determine the GSH transferase status of the subject.

"Variant profile" refers to the presence or absence of a plurality (e.g., two or more) of GSTO2 nucleotide sequence variants or GSTO2 amino acid sequence variants. For example, a variant profile can include the complete GSTO2 haplotype of the mammal (e.g., see Tables 5-9) or can include the presence or absence of a set of particular non-synonymous SNPs (e.g., single nucleotide substitutions that alter the amino acid sequence of a GSTO2 polypeptide). In one embodiment, the variant profile includes detecting the presence or absence of two or more non-synonymous SNPs (e.g., 2, 3, or 4 non-synonymous SNPs) described herein. There may be ethnic-specific pharmacogenetic variation, as certain of the nucleotide and amino acid sequence variants described herein were detected solely in African-American, Caucasian-American, Han Chinese-American, or Mexican-American subjects. In addition, the variant profile can include detecting the presence or absence of any type of GSTO2 SNP together with any other GSTO2 SNP (e.g., a polymorphism pair or a group of polymorphism pairs). Such polymorphism pairs include, without limitation, the pairs described in Table 4. Further, a variant profile can include detecting the presence or absence of any GSTO2 SNP together with any SNP from other GSH transferases.

GSH transferase activity of an enzyme such as GSTO2 can be measured using, for example, in vitro methods such as those described herein. As used herein, the term "reduced GSH transferase status" refers to a decrease (e.g., a 5%, 10%, 15%, 20%, 25%, 30%, 40%, 50%, 60%, 70%, 75%, 80%, 90%, 95%, or 100% decrease) in GSH transferase activity (e.g., GSTO2 activity) of a subject, as compared to a control level of GSH transferase activity. Similarly, the term "enhanced GSH transferase status" refers to an increase (e.g., a 5%, 10%, 15%, 20%, 25%, 30%, 40%, 50%, 60%, 70%, 75%, 80%, 90%, 95%, 100%, or more than 100% increase) in GSH transferase activity of a subject, as compared to a control level of GSH transferase activity. A control level of GSH transferase activity can be, for example, an average level of GSH transferase activity in a population of individuals. In one embodiment, the population includes individuals that do not contain particular GSTO2 nucleotide sequence variants or particular GSTO2 amino acid sequence variants (e.g., particular variants that affect GSH transferase status). Alternatively, a control level of GSH transferase activity can refer to the level of GSH transferase activity in a control subject (e.g., a subject that does not contain a GSTO2 nucleic acid containing a variant).

In some embodiments, evaluation of GSH transferase status can be used in diagnostic assays to determine whether a particular therapy may be useful in an individual, or to tailor particular treatment regimens to an individual. For example, the presence of absence of one or more variants may indicate an individual's ability to metabolize arsenic, a drinking water contaminant, or arsenic trioxide, an agent that can be used to treat acute promyelocytic leukemia. In further embodiments, GSH transferase status can be linked to predisposition to a particular disease or condition. For example, identification of GSTO2 sequence variants also may allow predisposition to conditions such as cancer, Alzheimer's, or Parkinson's disease to be assessed in individuals. Additional risk factors including, for example, family history and other genetic factors can be considered when determining risk. Predisposition to such diseases can be determined based on the presence or absence of a single GSTO2 sequence variant or based on a variant profile.

Determination of GSH transferase status and predisposition to conditions such as cancer, Alzheimer's, or Parkinson's disease can include identification of genetic markers (e.g., polymorphisms) in linkage disequilibrium with particular GSTO2 alleles. Although such markers may not be relevant from a functional perspective (i.e., may not directly affect function of GSTO2), their presence can be predictive of functional/clinically relevant polymorphisms. Thus, this document also provides methods for detecting a genotype by screening for genetic markers in linkage disequilibrium with particular GSTO2 alleles. The methods can include providing a nucleic acid sample from a subject (e.g., a human subject), and screening the sample for one or more markers in linkage disequilibrium with a particular GSTO2 allele. For example, a method can include screening for markers in linkage disequilibrium with a SNP at nucleotide 121, 389, 424, or 472 relative to the adenine in the translation initiation codon (nucleotide 23393, 27473, 27508, or 45662, respectively, of SEQ ID NO:1). Methods also can include screening for genetic markers in linkage disequilibrium with any of the other SNPs shown in Table 2.

Articles of Manufacture

Articles of manufacture also are provided herein, and can include populations of isolated GSTO2 nucleic acid molecules or GSTO2 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different GSTO2 nucleic acid or GSTO2 polypeptide sequence variant. Such articles of manufacture can include two or more sequence variants of GSTO2, or can include all of the sequence variants known for GSTO2. For example, the article of manufacture can include two or more of the sequence variants identified herein and one or more other GSTO2 sequence variants, such as nucleic acid variants that occur in the promoter region of the GSTO2 gene. Furthermore, nucleic acid molecules containing sequence variants for other GSH transferases can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al. (1996) *Nature Genet.* 14:441-447; and U.S. Pat. Nos. 5,770, 722 and 5,733,729.

The invention will be further described in the following examples, which do not limit the scope of the invention described in the claims.

EXAMPLES

Example 1

Methods and Materials

PCR Amplification and DNA Sequencing: DNA samples from 60 Caucasian-American, 60 African-American, 60 Han Chinese-American, and 60 Mexican-American subjects were obtained from the Coriell Institute Cell Repository (Camden, N.J.). These samples had been anonymized, and written informed consent had been obtained from all donors for the use of their DNA for this purpose. All experiments were reviewed and approved by the Mayo Clinic Institutional Review Board. Fourteen PCR reactions were performed with each DNA sample to amplify all GSTO2 exons and splice junctions, as well as a portion of the 5' flanking region. Primers were designed to hybridize within introns, the 5'-FR, or the 3'-UTR. This approach was used to ensure that a GSTO2 processed pseudogene that maps to chromosome 3 (Whitbread et al. (2003) *Pharmacogenet.* 13:131-144) would not be amplified. Amplicons were sequenced using dye-primer sequencing chemistry to facilitate the identification of heterozygous bases (Chadwick et al. (1996) *Biotechniques* 20:676-683). To make that possible, universal M13 sequencing tags were added to the 5'-ends of each forward and reverse primer. Forward primers contained the M13 forward sequence (5'-TGTAAAACGACGGCCAGT-3'; SEQ ID NO:10), and reverse primers contained the M13 reverse sequence (5'-CAGGAAACAGCTATGACC-3'; SEQ ID NO:11). In addition, resequencing of the GSTO2 5'-FR and the intergenic area utilized dye terminator chemistry. The sequences and locations of each primer within the gene are listed in Table 1. "F" represents forward; "R," reverse; "U," upstream; "D," downstream; "I," intron; "FR," flanking region; and "UTR," untranslated region. The locations of primers within the gene were chosen to avoid repetitive sequence.

Amplifications were performed with AmpliTaq Gold DNA polymerase (Perkin Elmer, Foster City, Calif.) using a "hot start" to help ensure amplification specificity. Each 50 µl reaction mixture contained 1 U of DNA polymerase, 5 µl of a 10-fold diluted DNA sample (160-190 ng DNA), 10 µmol of each primer, 0.05 mM dNTP (Boehringer Mannheim, Indianapolis, Ind.), and 5 µl of 10×PCR buffer that contained 15 mM $MgCl_2$ (Perkin Elmer). Amplifications were performed with a Perkin Elmer model 9700 thermal cycler. PCR cycling parameters involved a 12 minutes hot start at 94° C., 30 cycles at 94° C. for 30 seconds, 30 seconds at the annealing temperature, and a final 10 minute extension at 72° C.

Amplicons were sequenced in the Mayo Molecular Biology Core Facility with an ABI 377 DNA sequencer using BigDye™ (Perkin Elmer) dye-primer sequencing chemistry. Both DNA strands were sequenced in all cases. To exclude PCR-induced artifacts, independent amplification followed by DNA sequencing was performed for all samples in which a SNP was only observed once among the samples resequenced, or for samples with ambiguous chromatograms. DNA sequence chromatograms were analyzed using the PolyPhred 3.0 (Nickerson et al. (1997) *Nucl. Acids Res.* 25:2745-2751) and Consed 8.0 (Gordon et al. (1998) *Genome Res.* 8:195-202) programs developed by the University of Washington (Seattle, Wash.). The University of Wisconsin GCG software package, Version 10, was also used to analyze nucleotide sequence. GenBank accession numbers for the GSTO2 reference sequences were NT_030059 and NM_183239.

Recombinant GSTO2 Expression Constructs and Allozyme Expression: A WT GSTO2 cDNA open reading frame (ORF) sequence was amplified from a pooled human liver cDNA library (Clontech, Mountain View, Calif.). Expression constructs for the nonsynonymous cSNPs observed during the resequencing studies were generated by site-directed mutagenesis using "circular PCR." Sequences of the site-directed mutagenesis primers are listed in Table 1. Site-directed mutagenesis amplification reactions contained 1 U of Pfu Turbo DNA polymerase (Stratagene, La Jolla, Calif.) in a final volume of 25 µl, 10 µmol of primers, 0.24 mM dNTPs, and 2.5 µl of 10×PCR buffer. The sequences of expression constructs were confirmed by sequencing in both directions after cloning into the eukaryotic expression vector pCR3.1 (Invitrogen, Carlsbad, Calif.).

WT and variant GSTO2 expression constructs were transfected into COS-1 cells, together with pSV-β-galactosidase DNA (Promega) to make it possible to use β-galactosidase activity to correct for transfection efficiency. Transfections were performed with Lipofectamine 2000 (Invitrogen), and the cells were cultured for 48 hours in Dulbecco's modified Eagles medium (DMEM; Bio Whittaker, Walkersville, Md.) with 10% fetal bovine serum (Clontech). Cells were homogenized with a Polytron homogenizer (Brinkmann Instruments, Westbury, N.Y.). The homogenates were centrifuged at 100,000×g for 1 hour; and supernatant preparations were stored at −80° C.

Western Blot Analysis: Rabbit polyclonal antibodies were generated to GSTO2 (Cocalico Biologicals, Reamstown, Pa.) using a polypeptide that corresponded to amino acids 10 to 30, with an additional cysteine residue at the amino terminus. This synthetic polypeptide was conjugated to keyhole limpet hemocyanin prior to immunization of rabbits. For quantitative Western blot analysis, cytosol preparations of COS-1 cells transfected with the expression constructs were loaded on a 12% polyacrylamide gel on the basis of β-galactosidase activity to correct for possible variation in transfection efficiency. After SDS-PAGE, the proteins were transferred to a nitrocellulose membrane that was probed with rabbit antiserum to GSTO2, diluted 1:2000 with "blocking buffer." Goat anti-rabbit horseradish peroxidase, diluted 1:20,000, was used as the secondary antibody. Bound antibody was detected with the ECL Western blotting system (Amersham Pharmacia Biotech, Piscataway, N.J.). The level of immunoreactive protein was quantitated using IP Gel Lab (Biosystemetica, Plymouth, UK).

In vitro Translation and Degradation: Selected GSTO2 expression constructs were transcribed and translated in vitro in the presence of $^{35}$S-methionine (1000 Ci/mmol, 2.5 mCi total activity) (Amersham Pharmacia Biotech) using the TNT coupled rabbit reticulocyte lysate (RRL) system (Promega, Madison, Wis.). Reaction mixtures used to generate radioactively labeled protein were incubated at 30° C. for 90 minutes, and 5 μl aliquots were used to perform SDS-PAGE with 10% gels. Protein degradation studies were performed as described (Wang et al. (2003) *Pharmacogenet.* 13:555-564). Briefly, 50 μl of an adenosine 5'-triphosphate (ATP) generating system, 50 μl of "untreated" RRL, and 10 μl of $^{35}$S-methionine radioactively labeled GSTO2 allozyme were mixed. This mixture was incubated at 37° C., and 10 μl aliquots were removed at various time intervals, followed by SDS-PAGE. After electrophoresis, the gels were dried, exposed to X-ray film and the bands of radioactively labeled protein were quantified.

Data analysis: Statistical comparison of the data was performed by ANOVA using the StatView program, version 4.5 (Abacus Concepts, Inc., Berkeley, Calif.). Values for π, θ, and Tajima's D were calculated as described by Tajima (Tajima (1989) *Genet.* 123:585-595), followed by correction for length. Linkage analysis was performed after all DNA samples had been genotyped at each of the polymorphic sites observed, using the EH program developed by Terwilliger and Ott, *Handbook of Human Genetic Linkage*, The Johns Hopkins University Press, Baltimore, pp. 188-193 (1994). D' values, a quantitative method for reporting linkage data that is independent of allele frequency (Hartl and Clark *Principles of Population Genetics*, 3$^{rd}$ edition, Sinauer Associates, Inc., (Sunderland, Mass.), pp. 96-106 (1997); and Hedrick *Genetics of Populations*, 2$^{nd}$ edition, Jones and Bartlett (Sudbury, Mass.), pp. 396-405 (2000)), were calculated. The genotype data also were used to assign inferred haplotypes using a program based on the E-M algorithm (Long et al. (1995) *Am. J. Hum. Genet.* 56:799-810; Excoffier and Slatkin (1995) *Mol. Biol. Evol.* 12:921-927; and Schaid et al. (2002) *Am. J. Hum. Genet.* 70:425-434). Unambiguous haplotype assignment was possible on the basis of genotype for samples that contained no more than one heterozygous polymorphism. Group mean values were compared using student's t-test. Degradation data were plotted using GraphPad Prism (GraphPad Software, San Diego, Calif.).

GSTO2 Enzyme Activity: GSTO2 activity is measured using a bacterially expressed GSTO2 polypeptide. DHA is combined with DHA and GSH, and GSTO2 activity is measured as increased absorbance at 265 nm, which results from reduction of the DHA. This method also can be used to estimate apparent $K_m$ values. Alternatively, GSTO2 enzyme activity is measured in vivo (e.g., in CHO cells).

Quantitative RT-PCR: mRNA is isolated from COS-1 cells cotransfected with a control β-Galactosidase reporter and a GSTO2 WT expression construct or GSTO2 variant expression construct using an RNeasy Mini Kit (Qiagen, Valencia, Calif.), according to the manufacturer's instructions. RT-PCR is performed with primers for both GSTO2 and β-Galactosidase as an internal control.

Confocal microscopy: Fluorescein isothiocyanate (FITC)-conjugated goat anti-mouse immunoglobulin and tetramethylrhodamine isothiocyanate (TRITC)-conjugated goat anti-rabbit immunoglobulin are commercially available (e.g., from Southern Biotech (Birmingham, Ala.)). COS-1 cells are subcultured to 50-70% confluence on coverslips, transfected with expression constructs, and cultured for 48 hours. The cells are washed with phosphate buffered saline (PBS), fixed with 3% paraformaldehyde for 12 minutes at room temperature, washed, and incubated at room temperature for 5 minutes with buffer containing 0.5% Triton X-100. The coverslips are then incubated with primary antibodies—rabbit polyclonal antihuman antibody against calnexin (an endoplasmic reticulum marker) and mouse monoclonal anti-His antibody, followed by FITC-conjugated goat anti-mouse or TRITC-conjugated goat anti-rabbit IgG antibody. The COS-1 cells are viewed using a Zeiss LSM 510 confocal microscope with 488 or 570 nm filters for excitation of the green or red fluorochrome, respectively.

GSTO2 reporter gene constructs and luciferase assay: Luciferase reporter gene constructs are created for the most common human GSTO2 5'-FR haplotypes (e.g., haplotypes having a frequency ≦3% in any of the populations). Specifically, a segment containing about 1000 bp of the GSTO2 5'-FR is amplified from human genomic DNA samples that contained the desired haplotypes. The forward and reverse primers include ACC65I and XhoI restriction sites, respectively, to enable subcloning of the amplicons into pGL-3 Basic (Promega), upstream of the firefly luciferase gene open reading frame (ORF). The insert is sequenced in both directions to ensure that the correct sequence is present.

The luciferase reporter gene constructs are used to transiently transfect primary cells or cell lines (e.g., liver, kidney, skeletal muscle, heart, lung, cervix, ovary, or prostate cells). Cells are transfected with 5 μg purified plasmid DNA with 50 ng pRL-TK (Promega) DNA. The *Renilla luciferase* activity expressed by pRL-TK is used as a control for transfection efficiency. Cells also are transfected with pGL-3 Basic without insert as a control. Transfection is performed using the TransFast reagent (Promega). After 48 hours, cells are lysed and reporter gene activity is measured using a Promega dual-luciferase assay system. Results are reported as the ratio of firefly luciferase light units to *Renilla luciferase* light units, and all values are expressed as a percentage of the activity of the pGL3 WT 5'-FR construct. All assays in three cell lines are performed at least in duplicate (e.g., in triplicate).

TABLE 1

PCR primers used for resequencing and site directed mutagenesis of GSTO2

| Primer Name | Region Amplified | Primer Sequence (5' to 3' direction) | SEQ ID NO |
|---|---|---|---|
| Resequencing primers | | | |
| GSTO1 3'UTR F(730) | 5' FR | TGTAAAACGACGGCCAGTGGGCAGGAGTCAGCAATAAA* | 12 |
| UR(-1348) | 5' FR | CAGGAAACAGCTATGACCGGTCTTCAGGGCCAACAATA | 13 |
| UF(-1462) | 5' FR | TGTAAAACGACGGCCAGTTGCTCTCTTGTTGCTTGTCTTC | 14 |
| UR(-791) | 5' FR | CAGGAAACAGCTATGACCAGCCTGCTGAATCGGAAAT | 15 |
| UF(-888) | 5' FR | TGTAAAACGACGGCCAGTTTCGCCATTGAGAGAAACCT | 16 |
| I1R(48) | Exon 1 (5' UTR) | CAGGAAACAGCTATGACCCTCAAACCCCTCTTCCCTTC | 17 |
| UF(-368) | Exon 1/Intron 1 | TGTAAAACGACGGCCAGTTAGTTGGCGGGTAGGATCAC | 18 |
| I1R(539) | Exon 1/Intron 1 | CAGGAAACAGCTATGACCGTGGTTTGCGAAGGTTTCAT | 19 |
| I1F(1608) | Intron 1 | TGTAAAACGACGGCCAGTTCTTTGGTGGCATTATTTTCCTA | 20 |
| I1R(2265) | Intron 1 | CAGGAAACAGCTATGACCAACCTTTTTGGATTTCACTTTCC | 21 |
| I1F(-1423) | Intron 1 | TGTAAAACGACGGCCAGTAGCCGGGAACCAATATGTCT | 22 |
| I1R(-1042) | Intron 1 | CAGGAAACAGCTATGACCCGTAATGGCTGCTCAACAAA | 23 |
| I1F(-242) | Exon 2 | TGTAAAACGACGGCCAGTGCTGTACTTACTTACCAAAGAGT | 24 |
| I2R(21) | Exon 2 | CAGGAAACAGCTATGACCGACCCCATGGAGAGCACTCACCT | 25 |
| E2F(-34) | Exons 2 and 3 | TGTAAAACGACGGCCAGTGAGCTCCGGGAGCTGCGCAAACCA | 26 |
| I3R(54) | Exons 2 and 3 | CAGGAAACAGCTATGACCGGGCTCCTGTGAGGCGCTGGGTTTGCT | 27 |
| I3F(-85) | Exon 4 | TGTAAAACGACGGCCAGTCTGATTGCTTCTGCTTTCAAGAAGA | 28 |
| I4R(140) | Exon 4 | CAGGAAACAGCTATGACCCATGCTAGCTAATCTCCTGAGGAT | 29 |
| I4F(-94) | Exon 5 | TGTAAAACGACGGCCAGTGCTGGAGTTATAAAGCTTCGCTGCCT | 30 |
| I5R(227) | Exon 5 | TGTAAAACGACGGCCAGTGAAAGGAAGCAATTCATGGCATGT | 31 |
| I5F(-148) | Exon 6 | CAGGAAACAGCTATGACCGAGAAGAAGCATTCTCCTAACCAGA | 32 |
| I6R(115) | Exon 6 | TGTAAAACGACGGCCAGTCTGATTCACTTCACAGACATCCTGA | 33 |
| I6F(-97) | Exon 7 | CAGGAAACAGCTATGACCCTCATTCTTCATATCTTGCAAATCTA | 34 |
| 3'UTR R(775) | Exon 7 | CAGGAAACAGCTATGACCCAAGCTGGGGAATTCTGGACAGCGA | 35 |
| I6F(-15) | Exon 7/3' FR | TGTAAAACGACGGCCAGTTTTCCTGTCTTGCAGCTGTG | 36 |
| 3'FR R(1288) | Exon 7/3' FR | CAGGAAACAGCTATGACCTCCCAAAATGTGCTCTGACA | 37 |
| 3'FR R(1218) | 3' FR | TGTAAAACGACGGCCAGTCCTGCCTAGCCTGTAGCTTCT | 38 |
| 3'FR R(1855) | 3' FR | CAGGAAACAGCTATGACCTCAACTTTATCCCCAGTGTGC | 39 |
| Mutagenesis primers | | | |
| O2_V41I_F | | AGGACCCGCCTCATCCTCAAG** | 40 |
| O2_V41I_R | | CTTGAGGATGAGGCGGGTCCT | 41 |
| O2_C130Y_F | | ACCAAGGAGTACCTGGTAGCGTTG | 42 |
| O2_C130Y_R | | CAACGCTACCAGGTACTCCTTGGT | 43 |
| O2_N142D_F | | GAATGCACTAATCTGAAGGCA | 44 |

TABLE 1-continued

PCR primers used for resequencing and site directed mutagenesis of GSTO2

| Primer Name | Region Amplified | Primer Sequence (5' to 3' direction) | SEQ ID NO |
|---|---|---|---|
| O2_N142D_R | | TGCCTTCAGATTAGTGCATTC | 45 |
| O2_L158I_F | | GAAGAGATTATTGAGTATCAG | 46 |
| O2_L158I_R | | CTGATACTCAATAATCTCTTC | 47 |

*Underlined nucleotides in resequencing primers indicate M13 tag
**Underlined nucleotides in mutagenesis primers indicate variant

Example 2

GSTO2 Polymorphisms

Fourteen separate PCR amplifications were performed for each of the DNA samples studied. All PCR amplicons were sequenced on both strands, making it possible to verify the presence of polymorphisms using data from the complimentary strand. Approximately $3 \times 10^6$ pg of DNA was sequenced and analyzed, including the "intergenic" area located between the GSTO1 and GSTO2 genes (i.e., between the final exon of GSTO1 and the first exon of GSTO2). A total of 66 polymorphisms were observed (Table 2). Polymorphisms in exons and flanking regions (FR) are numbered relative to the adenine in the GSTO2 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1).

Variant allele frequencies ranged from 0.8% to 78.3%, with differences between the African-American (AA), Caucasian-American (CA), Han Chinese-American (HCA), and Mexican-American (MA) subjects. Fifty-four SNPs were observed in AA subjects, 19 in CA subjects, 17 in HCA subjects, and 36 in MA subjects. Nineteen of these polymorphisms were specific to AA, 5 to CA, and 2 each were specific to HCA and MA subjects.

Six SNPs were observed within the coding-region (cSNPs), and four of those cSNPs—located in exons 2, 4, and 5—were nonsynonymous, resulting in the amino acid alterations Val41Ile, Cys130Tyr, Asn142Asp, and Leu158Ile. The Val41Ile polymorphism had a frequency of 0.9% in African-Americans but was not observed in DNA from Caucasian-American, Han Chinese-American, or Mexican-American subjects. The Cys130Tyr polymorphism had frequencies of 0.8% in African Americans and 1.7% in Han Chinese-Americans, but was not observed in Caucasian-Americans or Mexican-Americans. The Asn142Asp polymorphism had frequencies of 23.3% in African-Americans, 69.2% in Caucasian-Americans, 78.3% in Han Chinese-Americans, and 74.2% in Mexican-Americans. The Leu158Ile polymorphism had a frequency of 0.8% in Caucasian-Americans, but was not observed in African-Americans, Han Chinese-Americans, or Mexican-Americans. To exclude artifacts introduced by PCR-dependent misincorporation, independent amplifications were performed and the amplicons were sequenced in all cases in which a polymorphism was observed only once among the DNA samples studied. All polymorphisms were in Hardy-Weinberg equilibrium ($P > 0.05$).

Nucleotide diversity, a measure of genetic variation that is adjusted for the number of alleles studied, was calculated for the GSTO2 gene and for the intergenic region. Two standard measures of nucleotide diversity are $\pi$, average heterozygosity per site, and $\theta$, a population mutation measure that is theoretically equal to the neutral mutation parameter (Fullerton et al. (2000) *Am. J. Hum. Genet.* 67:881-900). Values for Tajima's D, a test for the neutral mutation hypothesis (Fullerton et al., supra), also were calculated (Table 3). Under conditions of neutrality, Tajima's D should equal 0. For GSTO2, none of the values for Tajima's D were statistically significant. For the intergenic region, Tajima's D value for AA subjects was statistically significant, raising the possibility that this area may be undergoing selection.

TABLE 2

Human GSTO2 polymorphisms and frequencies

| Polymorphism Position | Location in Gene | Position in SEQ ID 1 | Amino Acid Change | WT Nucleotide | Variant Sequence Nucleotide | AA | CA | HCA | MA |
|---|---|---|---|---|---|---|---|---|---|
| −2012-2013 | 5'FR | 15569/15570 | | | Insertion of G | 0.292 | 0.000 | 0.000 | 0.008 |
| −1785 | 5'FR | 15797 | | T | C | 0.050 | 0.000 | 0.000 | 0.000 |
| −1771 | 5'FR | 15811 | | G | C | 0.008 | 0.000 | 0.000 | 0.000 |
| −1664 | 5'FR | 15918 | | C | T | 0.300 | 0.000 | 0.000 | 0.008 |
| −1598 | 5'FR | 15984 | | C | G | 0.300 | 0.000 | 0.000 | 0.008 |
| −1576 | 5'FR | 16006 | | G | C | 0.300 | 0.000 | 0.000 | 0.008 |
| −1566 | 5'FR | 16016 | | G | A | 0.300 | 0.000 | 0.000 | 0.008 |
| −1541 | 5'FR | 16041 | | C | T | 0.008 | 0.000 | 0.000 | 0.000 |
| −1357 | 5'FR | 16225 | | C | A | 0.300 | 0.000 | 0.000 | 0.008 |
| −1189 | 5'FR | 16393 | | T | C | 0.300 | 0.000 | 0.000 | 0.008 |
| −1179 | 5'FR | 16403 | | G | T | 0.008 | 0.000 | 0.000 | 0.000 |
| −1105 | 5'FR | 16477 | | G | A | 0.117 | 0.258 | 0.167 | 0.242 |
| −1102 | 5'FR | 16480 | | T | G | 0.217 | 0.683 | 0.767 | 0.692 |
| −1009 | 5'FR | 16573 | | C | T | 0.300 | 0.000 | 0.000 | 0.008 |

TABLE 2-continued

Human GSTO2 polymorphisms and frequencies

| Polymorphism Position | Location in Gene | Position in SEQ ID 1 | Amino Acid Change | WT Nucleotide | Variant Sequence Nucleotide | AA | CA | HCA | MA |
|---|---|---|---|---|---|---|---|---|---|
| −781 | 5′FR | 16801 | | A | C | 0.283 | 0.000 | 0.000 | 0.008 |
| −730-731 | 5′FR | 16851/16852 | | | Insertion of T | 0.283 | 0.000 | 0.000 | 0.008 |
| −637 | 5′FR | 16945 | | C | T | 0.275 | 0.000 | 0.000 | 0.008 |
| −634 | 5′FR | 16948 | | C | G | 0.275 | 0.000 | 0.000 | 0.008 |
| −625 | Exon 1 | 16957 | | A | G | 0.000 | 0.000 | 0.017 | 0.000 |
| −530 | Exon 1 | 17052 | | C | G | 0.271 | 0.000 | 0.000 | 0.008 |
| −526 | Exon 1 | 17056 | | C | A | 0.000 | 0.008 | 0.000 | 0.000 |
| −463 | Exon 1 | 17119 | | G | A | 0.271 | 0.000 | 0.000 | 0.008 |
| −450 | Exon 1 | 17132 | | A | C | 0.271 | 0.000 | 0.000 | 0.008 |
| −424 | Exon 1 | 17158 | | G | A | 0.017 | 0.000 | 0.000 | 0.000 |
| −410 | Exon 1 | 17172 | | T | G | 0.008 | 0.000 | 0.000 | 0.000 |
| −293 | Exon 1 | 17289 | | A | T | 0.050 | 0.000 | 0.000 | 0.000 |
| −234 | Exon 1 | 17348 | | C | T | 0.008 | 0.000 | 0.000 | 0.000 |
| 52 | Intron 1 | 17402 | | A | G | 0.008 | 0.000 | 0.000 | 0.000 |
| 152 | Intron 1 | 17502 | | G | T | 0.033 | 0.000 | 0.000 | 0.000 |
| 310-311 | Intron 1 | 17660/17661 | | | Deletion of CG | 0.008 | 0.000 | 0.000 | 0.000 |
| 311 | Intron 1 | 17661 | | G | A | 0.300 | 0.000 | 0.000 | 0.008 |
| 333 | Intron 1 | 17683 | | T | C | 0.008 | 0.000 | 0.000 | 0.000 |
| 402 | Intron 1 | 17752 | | C | T | 0.042 | 0.025 | 0.017 | 0.025 |
| 426 | Intron 1 | 17776 | | T | C | 0.050 | 0.000 | 0.000 | 0.000 |
| 435 | Intron 1 | 17785 | | T | A | 0.017 | 0.000 | 0.000 | 0.000 |
| 477-478 | Intron 1 | 17827/17828 | | | Insertion of T | 0.008 | 0.033 | 0.033 | 0.000 |
| 1694 | Intron 1 | 19044 | | A | G | 0.050 | 0.000 | 0.000 | 0.008 |
| 2003 | Intron 1 | 19353 | | A | G | 0.300 | 0.000 | 0.000 | 0.008 |
| 2146 | Intron 1 | 19496 | | A | G | 0.000 | 0.017 | 0.000 | 0.008 |
| 2168 | Intron 1 | 19518 | | G | A | 0.200 | 0.000 | 0.017 | 0.017 |
| −1131 | Intron 1 | 21635 | | C | T | 0.417 | 0.025 | 0.017 | 0.025 |
| −185 | Intron 1 | 22581 | | A | G | 0.060 | 0.000 | 0.000 | 0.000 |
| −19 | Intron 1 | 22747 | | T | A | 0.000 | 0.000 | 0.000 | 0.008 |
| −12 | Intron 1 | 22754 | | G | A | 0.008 | 0.000 | 0.000 | 0.008 |
| −183 | Exon 2 | 22814 | | A | G | 0.108 | 0.242 | 0.175 | 0.183 |
| −16 | Intron 2 | 23291 | | C | T | 0.008 | 0.000 | 0.000 | 0.000 |
| 121 | Exon 3 | 23393 | Val41Ile | G | A | 0.009 | 0.000 | 0.000 | 0.000 |
| 20 | Intron 4 | 26217 | | T | C | 0.200 | 0.560 | 0.642 | 0.667 |
| 39 | Intron 4 | 26236 | | C | T | 0.000 | 0.000 | 0.000 | 0.008 |
| −38 | Intron 4 | 27413 | | A | C | 0.000 | 0.017 | 0.000 | 0.017 |
| 389 | Exon 5 | 27473 | Cys130Tyr | G | A | 0.008 | 0.000 | 0.017 | 0.000 |
| 424 | Exon 5 | 27508 | Asn142Asp | A | G | 0.233 | 0.692 | 0.783 | 0.742 |
| 74 | Intron 5 | 27626 | | A | G | 0.233 | 0.692 | 0.783 | 0.742 |
| 170 | Intron 5 | 27722 | | T | C | 0.000 | 0.008 | 0.000 | 0.000 |
| 472 | Exon 6 | 45662 | Leu158Ile | C | A | 0.000 | 0.008 | 0.000 | 0.000 |
| −55 | Intron 6 | 47154 | | C | G | 0.058 | 0.000 | 0.008 | 0.000 |
| −21 | Intron 6 | 47188 | | C | T | 0.108 | 0.000 | 0.008 | 0.000 |
| 591 | Exon 7 | 47224 | | G | T | 0.167 | 0.033 | 0.133 | 0.017 |
| 630 | Exon 7 | 47263 | | C | T | 0.117 | 0.000 | 0.000 | 0.008 |
| 1038 | 3′FR | 47671 | | C | T | 0.175 | 0.033 | 0.133 | 0.017 |
| 1080 | 3′FR | 47713 | | C | T | 0.000 | 0.008 | 0.000 | 0.008 |
| 1243 | 3′FR | 47876 | | A | G | 0.000 | 0.017 | 0.000 | 0.000 |
| 1343 | 3′FR | 47976 | | T | G | 0.125 | 0.000 | 0.000 | 0.000 |
| 1615 | 3′FR | 48248 | | C | T | 0.000 | 0.008 | 0.000 | 0.000 |
| 1649 | 3′FR | 48282 | | T | C | 0.000 | 0.000 | 0.000 | 0.008 |
| 1724 | 3′FR | 48357 | | C | T | 0.008 | 0.000 | 0.000 | 0.000 |

TABLE 3

| | Nucleotide diversity | | | |
|---|---|---|---|---|
| | $\pi \times 10^{-3}$* | $\theta \times 10^{-3}$ | Tajima's D | P value** |
| GSTO2 | | | | |
| AA | 1.30 ± 0.70 | 1.40 ± 0.40 | −0.37 | 0.72 |
| CA | 0.50 ± 0.30 | 0.40 ± 0.20 | 0.62 | 0.55 |
| HCA | 0.50 ± 0.30 | 0.60 ± 0.20 | −0.67 | 0.52 |
| MA | 0.50 ± 0.30 | 0.80 ± 0.30 | −1.30 | 0.20 |
| Intergenic region | | | | |
| AA | 3.80 ± 2.03 | 2.20 ± 0.73 | 1.94 | 0.05 |
| CA | 0.55 ± 0.44 | 0.25 ± 0.18 | 1.79 | 0.07 |
| HCA | 0.43 ± 0.37 | 0.25 ± 0.18 | 1.10 | 0.30 |
| MA | 0.66 ± 0.50 | 1.70 ± 0.60 | −1.65 | 0.10 |

*Values are parameter estimates mean ± SE.
**P values refer to Tajima's D.

Example 3

Linkage Disequilibrium Analysis and Haplotype Analysis

Linkage disequilibrium analysis was performed after all of the DNA samples had been genotyped at each of the polymorphic sites. Pairwise combinations of these polymorphisms were tested for linkage disequilibrium using the EH program developed by Terwilliger and Ott, supra. The output of this program was used to calculate d' values, a method for reporting linkage data that is independent of sample size. Pairwise combinations with a statistically significant linkage disequilibrium (P value<0.001) are shown in Table 4. D' values greater than 0 indicate a positive association, while d' values less than 0 indicate a negative association.

The genotype data also were used for haplotype analysis. Haplotypes typically are defined as combinations of alleles on a single chromosome, although they are sometimes referred to in a more restricted definition as all polymorphisms present on a single allele (Altshuler et al. *Nature* 437:1299-1320 (2005)). Haplotypes can be determined unequivocally if not more than one polymorphism per allele is heterozygous, but haplotypes also can be inferred computationally (Schaid, supra). GSTO2 haplotypes, both observed and inferred, with frequencies $\geq 0.08\%$, are listed in Tables 5-8. As shown in the tables, the identified haplotypes accounted for 88.9% of all DNA samples from Caucasian-American subjects, 80.8% of all DNA samples from African-American subjects, 95.0% of all DNA samples from Han Chinese-American subjects, and 90.9% of all DNA samples from Mexican-American subjects. A summary of haplotypes having frequencies $\geq 1\%$ is presented in Table 9. Haplotypes including one or more cSNPs are included even if their frequency is less than 1%.

TABLE 4

Linkage disequilibrium statistics for GSTO2

| Location 1 | Location 2 | D' value | P value |
|---|---|---|---|
| African American Population | | | |
| 5'FR(−2012) | 5'FR(−1664) | 1 | 0 |
| 5'FR(−2012) | 5'FR(−1598) | 1 | 0 |
| 5'FR(−2012) | 5'FR(−1576) | 1 | 0 |
| 5'FR(−2012) | 5'FR(−1566) | 1 | 0 |
| 5'FR(−2012) | 5'FR(−1357) | 0.96 | 0 |
| 5'FR(−2012) | 5'FR(−1189) | 1 | 0 |
| 5'FR(−2012) | 5'FR(−1102) | 1 | 0 |
| 5'FR(−2012) | 5'FR(−1009) | 1 | 0 |
| 5'FR(−2012) | 5'FR(−781) | 0.96 | 0 |
| 5'FR(−2012) | 5'FR(−730) | 0.96 | 0 |
| 5'FR(−2012) | 5'FR(−637) | 0.96 | 0 |
| 5'FR(−2012) | 5'FR(−634) | 0.96 | 0 |
| 5'FR(−2012) | 5'FR(−530) | 0.96 | 0 |
| 5'FR(−2012) | 5'FR(−463) | 0.96 | 0 |
| 5'FR(−2012) | 5'FR(−450) | 0.96 | 0 |
| 5'FR(−2012) | Intron 1(311) | 1 | 0 |
| 5'FR(−2012) | Intron 6(−55) | 1 | 0 |
| 5'FR(−2012) | Intron 6(−21) | 1 | 0 |
| 5'FR(−2012) | 3'FR(1343) | 0.77 | 0.0001 |
| 5'FR(−1785) | Exon 1(−293) | 1 | 0 |
| 5'FR(−1785) | Intron 1(426) | 1 | 0 |
| 5'FR(−1785) | Intron 1(−185) | 1 | 0 |
| 5'FR(−1785) | Exon 7(630) | 1 | 0 |
| 5'FR(−1664) | 5'FR(−1598) | 1 | 0 |
| 5'FR(−1664) | 5'FR(−1576) | 1 | 0 |
| 5'FR(−1664) | 5'FR(−1566) | 1 | 0 |
| 5'FR(−1664) | 5'FR(−1357) | 1 | 0 |
| 5'FR(−1664) | 5'FR(−1189) | 1 | 0 |

TABLE 4-continued

Linkage disequilibrium statistics for GSTO2

| Location 1 | Location 2 | D' value | P value |
|---|---|---|---|
| 5'FR(−1664) | 5'FR(−1109) | 1 | 0 |
| 5'FR(−1664) | 5'FR(−781) | 1 | 0 |
| 5'FR(−1664) | 5'FR(−730) | 1 | 0 |
| 5'FR(−1664) | 5'FR(−637) | 1 | 0 |
| 5'FR(−1664) | 5'FR(−634) | 1 | 0 |
| 5'FR(−1664) | 5'FR(−530) | 1 | 0 |
| 5'FR(−1664) | 5'FR(−463) | 1 | 0 |
| 5'FR(−1664) | 5'FR(−450) | 1 | 0 |
| 5'FR(−1664) | Intron 1(311) | 1 | 0 |
| 5'FR(−1664) | Intron 1(2003) | 1 | 0 |
| 5'FR(−1664) | Intron 6(−55) | 1 | 0.0001 |
| 5'FR(−1664) | Intron 6(−21) | 1 | 0 |
| 5'FR(−1664) | 3'FR(1343) | 0.76 | 0.0001 |
| 5'FR(−1598) | 5'FR(−1576) | 1 | 0 |
| 5'FR(−1598) | 5'FR(−1566) | 1 | 0 |
| 5'FR(−1598) | 5'FR(−1357) | 1 | 0 |
| 5'FR(−1598) | 5'FR(−1189) | 1 | 0 |
| 5'FR(−1598) | 5'FR(−1009) | 1 | 0 |
| 5'FR(−1598) | 5'FR(−781) | 1 | 0 |
| 5'FR(−1598) | 5'FR(−730) | 1 | 0 |
| 5'FR(−1598) | 5'FR(−637) | 1 | 0 |
| 5'FR(−1598) | 5'FR(−634) | 1 | 0 |
| 5'FR(−1598) | 5'FR(−530) | 1 | 0 |
| 5'FR(−1598) | 5'FR(−463) | 1 | 0 |
| 5'FR(−1598) | 5'FR(−450) | 1 | 0 |
| 5'FR(−1598) | Intron 1(311) | 1 | 0 |
| 5'FR(−1598) | Intron 1(2003) | 1 | 0 |
| 5'FR(−1598) | Exon 5(424) | 1 | 0 |
| 5'FR(−1598) | Intron 5(74) | 1 | 0 |
| 5'FR(−1598) | Intron 6(−21) | 1 | 0 |
| 5'FR(−1598) | 3'FR(1343) | 0.76 | 0.0001 |
| 5'FR(−1576) | 5'FR(1566) | 1 | 0 |
| 5'FR(−1576) | 5'FR(1357) | 1 | 0 |
| 5'FR(−1576) | 5'FR(1189) | 1 | 0 |
| 5'FR(−1576) | 5'FR(1009) | 1 | 0 |
| 5'FR(−1576) | 5'FR(−781) | 1 | 0 |
| 5'FR(−1576) | 5'FR(−730) | 1 | 0 |
| 5'FR(−1576) | 5'FR(−637) | 1 | 0 |
| 5'FR(−1576) | 5'FR(−634) | 1 | 0 |
| 5'FR(−1576) | 5'FR(−530) | 1 | 0 |
| 5'FR(−1576) | 5'FR(−463) | 1 | 0 |
| 5'FR(−1576) | 5'FR(−450) | 1 | 0 |
| 5'FR(−1576) | Intron 1(311) | 1 | 0 |
| 5'FR(−1576) | Intron 1(2003) | 1 | 0 |
| 5'FR(−1576) | Intron 6(−55) | 1 | 0.0001 |
| 5'FR(−1576) | Intron 6(−21) | 1 | 0 |
| 5'FR(−1576) | 3'FR(1343) | 0.76 | 0.0001 |
| 5'FR(−1566) | 5'FR(−1357) | 1 | 0 |
| 5'FR(−1566) | 5'FR(−1189) | 1 | 0 |
| 5'FR(−1566) | 5'FR(−1009) | 1 | 0 |
| 5'FR(−1566) | 5'FR(−781) | 0.96 | 0 |
| 5'FR(−1566) | 5'FR(−730) | 0.96 | 0 |
| 5'FR(−1566) | 5'FR(−637) | 0.96 | 0 |
| 5'FR(−1566) | 5'FR(−634) | 0.96 | 0 |
| 5'FR(−1566) | Exon 1(−530) | 0.96 | 0 |
| 5'FR(−1566) | Exon 1(−463) | 0.96 | 0 |
| 5'FR(−1566) | Exon 1(−450) | 0.96 | 0 |
| 5'FR(−1566) | Intron 1(311) | 1 | 0 |
| 5'FR(−1566) | Intron 1(2003) | 1 | 0 |
| 5'FR(−1566) | Intron 6(−21) | 0.87 | 0 |
| 5'FR(−1566) | 3'FR(1343) | 0.65 | 0.0004 |
| 5'FR(−1541) | Exon 1(−410) | 1 | 0 |
| 5'FR(−1357) | 5'FR(−1189) | 1 | 0 |
| 5'FR(−1357) | 5'FR(−1009) | 1 | 0 |
| 5'FR(−1357) | 5'FR(−781) | 1 | 0 |
| 5'FR(−1357) | 5'FR(−730) | 1 | 0 |
| 5'FR(−1357) | 5'FR(−637) | 1 | 0 |
| 5'FR(−1357) | 5'FR(−634) | 1 | 0 |
| 5'FR(−1357) | Exon 1(−530) | 1 | 0 |
| 5'FR(−1357) | Exon 1(−463) | 1 | 0 |
| 5'FR(−1357) | Intron 1(311) | 1 | 0 |
| 5'FR(−1357) | Intron 1(2003) | 1 | 0 |
| 5'FR(−1357) | Intron 6(−55) | 1 | 0.0001 |
| 5'FR(−1357) | Intron 6(−21) | 1 | 0 |

TABLE 4-continued

Linkage disequilibrium statistics for GSTO2

| Location 1 | Location 2 | D' value | P value |
|---|---|---|---|
| 5'FR(−1357) | 3'FR(1343) | 0.76 | 0.0001 |
| 5'FR(−1189) | 5'FR(−1009) | 1 | 0 |
| 5'FR(−1189) | 5'FR(−781) | 1 | 0 |
| 5'FR(−1189) | 5'FR(−730) | 1 | 0 |
| 5'FR(−1189) | 5'FR(−637) | 1 | 0 |
| 5'FR(−1189) | 5'FR(−634) | 1 | 0 |
| 5'FR(−1189) | Exon 1(−530) | 1 | 0 |
| 5'FR(−1189) | Exon 1(−463) | 1 | 0 |
| 5'FR(−1189) | Exon 1(−450) | 1 | 0 |
| 5'FR(−1189) | Intron 1(311) | 1 | 0 |
| 5'FR(−1189) | Intron 1(2003) | 1 | 0 |
| 5'FR(−1189) | Intron 6(−55) | 1 | 0.0001 |
| 5'FR(−1189) | Intron 6(−21) | 1 | 0 |
| 5'FR(−1189) | 3'FR(1343) | 0.76 | 0.0001 |
| 5'FR(−1105) | Exon 2(−183) | 1 | 0 |
| 5'FR(−1102) | Intron 4(20) | 1 | 0 |
| 5'FR(−1102) | Exon 5(424) | 1 | 0 |
| 5'FR(−1102) | Intron 5(74) | 1 | 0 |
| 5'FR(−1009) | 5'FR(−781) | 1 | 0 |
| 5'FR(−1009) | 5'FR(−730) | 1 | 0 |
| 5'FR(−1009) | 5'FR(−637) | 1 | 0 |
| 5'FR(−1009) | 5'FR(−634) | 1 | 0 |
| 5'FR(−1009) | Exon 1(530) | 1 | 0 |
| 5'FR(−1009) | Exon 1(463) | 1 | 0 |
| 5'FR(−1009) | Exon 1(450) | 1 | 0 |
| 5'FR(−1009) | Intron 1(311) | 1 | 0 |
| 5'FR(−1009) | Intron 1(2003) | 1 | 0 |
| 5'FR(−1009) | Intron 6(−55) | 1 | 0.0001 |
| 5'FR(−1009) | Intron 6(−21) | 1 | 0 |
| 5'FR(−1009) | 3'FR(1343) | 0.76 | 0.0001 |
| 5'FR(−781) | 5'FR(−730) | 1 | 0 |
| 5'FR(−781) | 5'FR(−637) | 1 | 0 |
| 5'FR(−781) | 5'FR(−634) | 1 | 0 |
| 5'FR(−781) | Exon 1(−530) | 1 | 0 |
| 5'FR(−781) | Exon 1(−463) | 1 | 0 |
| 5'FR(−781) | Exon 1(−450) | 1 | 0 |
| 5'FR(−781) | Intron 1(311) | 1 | 0 |
| 5'FR(−781) | Intron 1(2003) | 1 | 0 |
| 5'FR(−781) | Intron 6(−21) | 0.87 | 0 |
| 5'FR(−730) | 5'FR(−637) | 1 | 0 |
| 5'FR(−730) | 5'FR(−634) | 1 | 0 |
| 5'FR(−730) | Exon 1(−530) | 1 | 0 |
| 5'FR(−730) | Exon 1(−463) | 1 | 0 |
| 5'FR(−730) | Exon 1(−450) | 1 | 0 |
| 5'FR(−730) | Intron 1(311) | 1 | 0 |
| 5'FR(−730) | Intron 1(2003) | 1 | 0 |
| 5'FR(−730) | Intron 6(−21) | 0.87 | 0 |
| 5'FR(637) | 5'FR(634) | 1 | 0 |
| 5'FR(637) | Exon 1(−530) | 1 | 0 |
| 5'FR(637) | Exon 1(−463) | 1 | 0 |
| 5'FR(637) | Exon 1(−450) | 1 | 0 |
| 5'FR(637) | Intron 1(311) | 1 | 0 |
| 5'FR(637) | Intron 1(2003) | 1 | 0 |
| 5'FR(637) | Intron 6(−21) | 0.87 | 0 |
| 5'FR(634) | Exon 1(−530) | 1 | 0 |
| 5'FR(634) | Exon 1(−463) | 1 | 0 |
| 5'FR(634) | Exon 1(−450) | 1 | 0 |
| 5'FR(634) | Intron 1(311) | 1 | 0 |
| 5'FR(634) | Intron 1(2003) | 1 | 0 |
| 5'FR(634) | Intron 6(−21) | 0.87 | 0 |
| 5'FR(530) | Exon 1(−463) | 1 | 0 |
| 5'FR(530) | Exon 1(−450) | 1 | 0 |
| 5'FR(530) | Intron 1(2003) | 1 | 0 |
| 5'FR(530) | Intron 6(−21) | 0.87 | 0 |
| Exon 1(−463) | Exon 1(−450) | 1 | 0 |
| Exon 1(−463) | Intron 1(311) | 1 | 0 |
| Exon 1(−463) | Intron 1(2003) | 1 | 0 |
| Exon 1(−463) | Intron 6(−21) | 0.87 | 0 |
| Exon 1(−450) | Intron 1(311) | 1 | 0 |
| Exon 1(−450) | Intron 1(2003) | 1 | 0 |
| Exon 1(−450) | Intron 6(−21) | 0.87 | 0 |
| Exon 1(−293) | Intron 1(426) | 1 | 0 |
| Exon 1(−293) | Intron 1(−185) | 1 | 0 |
| Exon 1(−293) | Exon 7(630) | 1 | 0 |
| Intron 1(52) | Intron 1(310) | 1 | 0 |
| Intron 1(52) | Intron 1(−12) | 1 | 0 |
| Intron 1(152) | Intron 6(−55) | 1 | 0 |
| Intron 1(310) | Intron 1(−12) | 1 | 0 |
| Intron 1(311) | Intron 1(2003) | 1 | 0 |
| Intron 1(311) | Intron 6(−21) | 1 | 0 |
| Intron 1(402) | Intron 1(−1131) | 1 | 0 |
| Intron 1(426) | Intron 1(−185) | 1 | 0 |
| Intron 1(426) | Exon 7(630) | 1 | 0 |
| Intron 1(1694) | Exon 7(630) | 1 | 0 |
| Intron 1(2003) | Intron 6(−55) | 1 | 0.0001 |
| Intron 1(2003) | Intron 6(−21) | 1 | 0 |
| Intron 1(2003) | 3'FR(1343) | 0.76 | 0.0001 |
| Intron 1(2168) | Exon 7(591) | 0.59 | 0 |
| Intron 1(2168) | 3'FR(1038) | 0.61 | 0 |
| Intron 1(−185) | Exon 7(630) | 0.82 | 0 |
| Intron 4(20) | Exon 5(424) | 1 | 0 |
| Intron 4(20) | Intron 5(74) | 1 | 0 |
| Exon 5(424) | Intron 5(74) | 1 | 0 |
| Intron 6(−55) | Intron 6(−21) | 1 | 0 |
| Intron 6(−55) | 3'FR(1343) | 1 | 0 |
| Intron 6(−21) | 3'FR(1343) | 1 | 0 |
| Exon 7(591) | 3'FR(1038) | 1 | 0 |
| Caucasian American Population | | | |
| 5'FR(−2012) | Intron 1(2146) | 0.49 | 0.0002 |
| 5'FR(−1105) | 5'FR(−1102) | 1 | 0 |
| 5'FR(−1105) | Exon 2(−183) | 0.9 | 0 |
| 5'FR(−1105) | Intron 4(20) | 0.79 | 0 |
| 5'FR(−1105) | Exon 5(424) | 0.8 | 0 |
| 5'FR(−1105) | Intron 5(74) | 0.8 | 0 |
| 5'FR(−1102) | Intron 1(402) | 0.85 | 0.0001 |
| 5'FR(−1102) | Intron 1(−1131) | 0.85 | 0.0001 |
| 5'FR(−1102) | Exon 2(−183) | 0.89 | 0 |
| 5'FR(−1102) | Intron 4(20) | 0.77 | 0.0002 |
| 5'FR(−1102) | Intron 4(−38) | 0.78 | 0 |
| 5'FR(−1102) | Exon 5(424) | 0.82 | 0 |
| 5'FR(−1102) | Intron 5(74) | 0.82 | 0 |
| Exon 1(−526) | Exon 7(591) | 1 | 0.0002 |
| Intron 1(402) | Intron 1(−1131) | 1 | 0 |
| Intron 1(402) | Intron 4(−38) | 1 | 0 |
| Intron 1(477) | Exon 7(591) | 0.74 | 0 |
| Intron 1(477) | 3'FR(1038) | 1 | 0 |
| Intron 1(477) | 3'FR(1243) | 1 | 0 |
| Intron 1(−1131) | Intron 4(−38) | 1 | 0 |
| Exon 2(−183) | Intron 4(20) | 1 | 0 |
| Exon 2(−183) | Exon 5(424) | 1 | 0 |
| Exon 2(−183) | Intron 5(74) | 1 | 0 |
| Intron 4(20) | Exon 5(424) | 1 | 0 |
| Intron 4(20) | Intron 5(74) | 1 | 0 |
| Exon 5(424) | Intron 5(74) | 1 | 0 |
| Exon 7(591) | 3'FR(1038) | 0.74 | 0 |
| Mexican American Population | | | |
| 5'FR(−2012) | 5'FR(−1664) | 1 | 0 |
| 5'FR(−2012) | 5'FR(−1598) | 1 | 0 |
| 5'FR(−2012) | 5'FR(−1576) | 1 | 0 |
| 5'FR(−2012) | 5'FR(−1566) | 1 | 0 |
| 5'FR(−2012) | 5'FR(−1357) | 1 | 0 |
| 5'FR(−2012) | 5'FR(−1189) | 1 | 0 |
| 5'FR(−2012) | 5'FR(−1009) | 1 | 0 |
| 5'FR(−2012) | 5'FR(−781) | 1 | 0 |
| 5'FR(−2012) | 5'FR(−730) | 1 | 0 |
| 5'FR(−2012) | 5'FR(−637) | 1 | 0 |
| 5'FR(−2012) | 5'FR(−634) | 1 | 0 |
| 5'FR(−2012) | Exon 1(−530) | 1 | 0 |
| 5'FR(−2012) | Exon 1(−463) | 1 | 0 |
| 5'FR(−2012) | Exon 1(−450) | 1 | 0 |
| 5'FR(−2012) | Intron 1(311) | 1 | 0 |
| 5'FR(−2012) | Intron 1(2003) | 1 | 0 |
| 5'FR(−2012) | 3'FR(1649) | 1 | 0 |
| 5'FR(−1664) | 5'FR(1598) | 1 | 0 |
| 5'FR(−1664) | 5'FR(1576) | 1 | 0 |
| 5'FR(−1664) | 5'FR(1566) | 1 | 0 |

TABLE 4-continued

Linkage disequilibrium statistics for GSTO2

| Location 1 | Location 2 | D' value | P value |
|---|---|---|---|
| 5'FR(−1664) | 5'FR(1357) | 1 | 0 |
| 5'FR(−1664) | 5'FR(1189) | 1 | 0 |
| 5'FR(−1664) | 5'FR(1009) | 1 | 0 |
| 5'FR(−1664) | 5'FR(781) | 1 | 0 |
| 5'FR(−1664) | 5'FR(730) | 1 | 0 |
| 5'FR(−1664) | 5'FR(637) | 1 | 0 |
| 5'FR(−1664) | 5'FR(634) | 1 | 0 |
| 5'FR(−1664) | Exon 1(−530) | 1 | 0 |
| 5'FR(−1664) | Exon 1(−463) | 1 | 0 |
| 5'FR(−1664) | Exon 1(−450) | 1 | 0 |
| 5'FR(−1664) | Intron 1(311) | 1 | 0 |
| 5'FR(−1664) | Intron 1(2003) | 1 | 0 |
| 5'FR(−1664) | 3'FR(1649) | 1 | 0 |
| 5'FR(−1598) | 5'FR(−1576) | 1 | 0 |
| 5'FR(−1598) | 5'FR(−1566) | 1 | 0 |
| 5'FR(−1598) | 5'FR(−1357) | 1 | 0 |
| 5'FR(−1598) | 5'FR(−1189) | 1 | 0 |
| 5'FR(−1598) | 5'FR(−1009) | 1 | 0 |
| 5'FR(−1598) | 5'FR(−781) | 1 | 0 |
| 5'FR(−1598) | 5'FR(−730) | 1 | 0 |
| 5'FR(−1598) | 5'FR(−637) | 1 | 0 |
| 5'FR(−1598) | 5'FR(−634) | 1 | 0 |
| 5'FR(−1598) | Exon 1(−530) | 1 | 0 |
| 5'FR(−1598) | Exon 1(−463) | 1 | 0 |
| 5'FR(−1598) | Exon 1(−450) | 1 | 0 |
| 5'FR(−1598) | Intron 1(311) | 1 | 0 |
| 5'FR(−1598) | Intron 1(2003) | 1 | 0 |
| 5'FR(−1598) | 3'FR(1649) | 1 | 0 |
| 5'FR(−1576) | 5'FR(−1566) | 1 | 0 |
| 5'FR(−1576) | 5'FR(−1357) | 1 | 0 |
| 5'FR(−1576) | 5'FR(−1189) | 1 | 0 |
| 5'FR(−1576) | 5'FR(−1009) | 1 | 0 |
| 5'FR(−1576) | 5'FR(−781) | 1 | 0 |
| 5'FR(−1576) | 5'FR(−730) | 1 | 0 |
| 5'FR(−1576) | 5'FR(−637) | 1 | 0 |
| 5'FR(−1576) | 5'FR(−634) | 1 | 0 |
| 5'FR(−1576) | Exon 1(−530) | 1 | 0 |
| 5'FR(−1576) | Exon 1(−463) | 1 | 0 |
| 5'FR(−1576) | Exon 1(−450) | 1 | 0 |
| 5'FR(−1576) | Intron 1(311) | 1 | 0 |
| 5'FR(−1576) | Intron 1(2003) | 1 | 0 |
| 5'FR(−1576) | 3'FR(1649) | 1 | 0 |
| 5'FR(−1566) | 5'FR(−1357) | 1 | 0 |
| 5'FR(−1566) | 5'FR(−1189) | 1 | 0 |
| 5'FR(−1566) | 5'FR(−1009) | 1 | 0 |
| 5'FR(−1566) | 5'FR(−781) | 1 | 0 |
| 5'FR(−1566) | 5'FR(−730) | 1 | 0 |
| 5'FR(−1566) | 5'FR(−637) | 1 | 0 |
| 5'FR(−1566) | 5'FR(−634) | 1 | 0 |
| 5'FR(−1566) | Exon 1(−530) | 1 | 0 |
| 5'FR(−1566) | Exon 1(−463) | 1 | 0 |
| 5'FR(−1566) | Exon 1(−450) | 1 | 0 |
| 5'FR(−1566) | Intron 1(311) | 1 | 0 |
| 5'FR(−1566) | Intron 1(2003) | 1 | 0 |
| 5'FR(−1566) | 3'FR(1649) | 1 | 0 |
| 5'FR(−1357) | 5'FR(−1189) | 1 | 0 |
| 5'FR(−1357) | 5'FR(−1109) | 1 | 0 |
| 5'FR(−1357) | 5'FR(−781) | 1 | 0 |
| 5'FR(−1357) | 5'FR(−730) | 1 | 0 |
| 5'FR(−1357) | 5'FR(−637) | 1 | 0 |
| 5'FR(−1357) | 5'FR(−634) | 1 | 0 |
| 5'FR(−1357) | Exon 1(−530) | 1 | 0 |
| 5'FR(−1357) | Exon 1(−463) | 1 | 0 |
| 5'FR(−1357) | Exon 1(−450) | 1 | 0 |
| 5'FR(−1357) | Intron 1(311) | 1 | 0 |
| 5'FR(−1357) | Intron 1(2003) | 1 | 0 |
| 5'FR(−1357) | 3'FR(1649) | 1 | 0 |
| 5'FR(−1189) | 5'FR(−1009) | 1 | 0 |
| 5'FR(−1189) | 5'FR(−781) | 1 | 0 |
| 5'FR(−1189) | 5'FR(−730) | 1 | 0 |
| 5'FR(−1189) | 5'FR(−637) | 1 | 0 |
| 5'FR(−1189) | 5'FR(−634) | 1 | 0 |
| 5'FR(−1189) | Exon 1(−530) | 1 | 0 |
| 5'FR(−1189) | Exon 1(−463) | 1 | 0 |
| 5'FR(−1189) | Exon 1(−450) | 1 | 0 |
| 5'FR(−1189) | Intron 1(311) | 1 | 0 |
| 5'FR(−1189) | Intron 1(2003) | 1 | 0 |
| 5'FR(−1189) | 3'FR(1649) | 1 | 0 |
| 5'FR(−1105) | 5'FR(−1102) | 1 | 0 |
| 5'FR(−1105) | Exon 2(−183) | 1 | 0 |
| 5'FR(−1105) | Intron 4(20) | 0.76 | 0 |
| 5'FR(−1105) | Exon 5(424) | 0.75 | 0 |
| 5'FR(−1105) | Intron 5(74) | 0.75 | 0 |
| 5'FR(−1102) | Exon 2(−183) | 1 | 0 |
| 5'FR(−1102) | Intron 4(20) | 0.78 | 0 |
| 5'FR(−1102) | Exon 5(424) | 1 | 0 |
| 5'FR(−1102) | Intron 5(74) | 1 | 0 |
| 5'FR(−1009) | 5'FR(−781) | 1 | 0 |
| 5'FR(−1009) | 5'FR(−730) | 1 | 0 |
| 5'FR(−1009) | 5'FR(−637) | 1 | 0 |
| 5'FR(−1009) | 5'FR(−634) | 1 | 0 |
| 5'FR(−1009) | Exon 1(−530) | 1 | 0 |
| 5'FR(−1009) | Exon 1(−463) | 1 | 0 |
| 5'FR(−1009) | Exon 1(−450) | 1 | 0 |
| 5'FR(−1009) | Intron 1(311) | 1 | 0 |
| 5'FR(−1009) | Intron 1(2003) | 1 | 0 |
| 5'FR(−1009) | 3'FR(1649) | 1 | 0 |
| 5'FR(−781) | 5'FR(−730) | 1 | 0 |
| 5'FR(−781) | 5'FR(−637) | 1 | 0 |
| 5'FR(−781) | 5'FR(−634) | 1 | 0 |
| 5'FR(−781) | Exon 1(−530) | 1 | 0 |
| 5'FR(−781) | Exon 1(−463) | 1 | 0 |
| 5'FR(−781) | Exon 1(−450) | 1 | 0 |
| 5'FR(−781) | Intron 1(311) | 1 | 0 |
| 5'FR(−781) | Intron 1(2003) | 1 | 0 |
| 5'FR(−781) | 3'FR(1649) | 1 | 0 |
| 5'FR(−730) | 5'FR(−637) | 1 | 0 |
| 5'FR(−730) | 5'FR(−634) | 1 | 0 |
| 5'FR(−730) | Exon 1(−530) | 1 | 0 |
| 5'FR(−730) | Exon 1(−463) | 1 | 0 |
| 5'FR(−730) | Exon 1(−450) | 1 | 0 |
| 5'FR(−730) | Intron 1(311) | 1 | 0 |
| 5'FR(−730) | Intron 1(2003) | 1 | 0 |
| 5'FR(−730) | 3'FR(1649) | 1 | 0 |
| 5'FR(−637) | 5'FR(−634) | 1 | 0 |
| 5'FR(−637) | Exon 1(−530) | 1 | 0 |
| 5'FR(−637) | Exon 1(−463) | 1 | 0 |
| 5'FR(−637) | Exon 1(−450) | 1 | 0 |
| 5'FR(−637) | Intron 1(311) | 1 | 0 |
| 5'FR(−637) | Intron 1(2003) | 1 | 0 |
| 5'FR(−637) | 3'FR(1649) | 1 | 0 |
| 5'FR(−634) | Exon 1(−530) | 1 | 0 |
| 5'FR(−634) | Exon 1(−463) | 1 | 0 |
| 5'FR(−634) | Exon 1(−450) | 1 | 0 |
| 5'FR(−634) | Intron 1(311) | 1 | 0 |
| 5'FR(−634) | Intron 1(2003) | 1 | 0 |
| 5'FR(−634) | 3'FR(1649) | 1 | 0 |
| Exon 1(−530) | Exon 1(−463) | 1 | 0 |
| Exon 1(−530) | Exon 1(−450) | 1 | 0 |
| Exon 1(−530) | Intron 1(311) | 1 | 0 |
| Exon 1(−530) | Intron 1(2003) | 1 | 0 |
| Exon 1(−530) | 3'FR(1649) | 1 | 0 |
| Exon 1(−463) | Exon 1(−450) | 1 | 0 |
| Exon 1(−463) | Intron 1(311) | 1 | 0 |
| Exon 1(−463) | Intron 1(2003) | 1 | 0 |
| Exon 1(−463) | 3'FR(1649) | 1 | 0 |
| Exon 1(−450) | Intron 1(311) | 1 | 0 |
| Exon 1(−450) | Intron 1(2003) | 1 | 0 |
| Exon 1(−450) | 3'FR(1649) | 1 | 0 |
| Intron 1(311) | Intron 1(2003) | 1 | 0 |
| Intron 1(311) | 3'FR(1649) | 1 | 0 |
| Intron 1(402) | Intron 1(−1131) | 1 | 0 |
| Intron 1(402) | Intron 1(−38) | 1 | 0 |
| Intron 1(1694) | Exon 7(630) | 1 | 0 |
| Intron 1(2003) | 3'FR(1649) | 1 | 0 |
| Intron 1(2168) | Exon 7(591) | 0.49 | 0.0002 |
| Intron 1(2168) | 3'FR(1038) | 0.49 | 0.0002 |
| Intron 1(1131) | Intron 4(−38) | 1 | 0 |

TABLE 4-continued

Linkage disequilibrium statistics for GSTO2

| Location 1 | Location 2 | D' value | P value |
|---|---|---|---|
| Exon 2(−183) | Intron(20) | 1 | 0 |
| Exon 2(−183) | Exon 5(424) | 1 | 0 |
| Exon 2(−183) | Intron 5(74) | 1 | 0 |
| Intron 4(20) | Exon 5(424) | 1 | 0 |
| Intron 4(20) | Intron 5(74) | 1 | 0 |
| Exon 5(424) | Intron 5(74) | 1 | 0 |
| Exon 7(591) | 3'FR(1038) | 1 | 0 |
| Han Chinese American Population | | | |
| 5'FR(−1105) | 5'FR(−1102) | 1 | 0 |
| 5'FR(−1105) | Exon 2(−183) | 1 | 0 |
| 5'FR(−1105) | Exon 2(424) | 0.86 | 0 |
| 5'FR(−1105) | Intron 5(74) | 0.86 | 0 |
| 5'FR(−1102) | Exon 2(−183) | 1 | 0 |
| 5'FR(−1102) | Intron 5(20) | 0.8 | 0 |
| 5'FR(−1102) | Exon 5(424) | 0.95 | 0 |
| 5'FR(−1102) | Intron 5(74) | 0.95 | 0 |
| Exon 1(−625) | Intron 1(477) | 0.95 | 0 |
| Intron 1(402) | Intron 1(−1131) | 1 | 0 |
| Intron 1(477) | 3'FR(1038) | 1 | 1E−04 |
| Exon 2(−183) | Exon 5(424) | 1 | 0 |
| Exon 2(−183) | Intron 5(74) | 1 | 0 |
| Intron 4(20) | Exon 5(424) | 1 | 0 |
| Intron 4(20) | Intron 5(74) | 1 | 0 |
| Exon 5(424) | Intron 5(74) | 1 | 0 |
| Intron 6(−55) | Intron 6(−21) | 1 | 0 |
| Exon 7(591) | 3'FR(1038) | 0.93 | 0 |

TABLE 5

GSTO2 Haplotypes for Caucasian-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 50.06% | o | D | T | G | C | C | G | G | C | C | T | G | G | G |
| 21.60% | o | D | T | G | C | C | G | G | C | C | T | G | A | T |
| 9.92% | o | D | T | G | C | C | G | G | C | C | T | G | G | G |
| 3.14% | i | D | T | G | C | C | G | G | C | C | T | G | A | T |
| 1.67% | i | D | T | G | C | C | G | G | C | C | T | G | G | G |
| 1.67% | i | D | T | G | C | C | G | G | C | C | T | G | G | T |
| 0.83% | i | D | T | G | C | C | G | G | C | C | T | G | G | T |

| Freq. | 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) |
|---|---|---|---|---|---|---|---|---|---|---|---|---|---|---|
| 50.06% | C | A | D | C | C | A | C | C | G | A | G | T | A | C |
| 21.60% | C | A | D | C | C | A | C | C | G | A | G | T | A | C |
| 9.92% | C | A | D | C | C | A | C | C | G | A | G | T | A | C |
| 3.14% | C | A | D | C | C | A | C | C | G | A | G | T | A | C |
| 1.67% | C | A | D | C | C | A | C | C | G | A | G | T | A | C |
| 1.67% | C | A | D | C | C | A | C | C | G | A | G | T | A | C |
| 0.83% | C | A | D | C | C | A | C | C | G | A | G | T | A | C |

| Freq. | Intron1 (+52) | Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) |
|---|---|---|---|---|---|---|---|---|---|---|---|---|---|---|
| 50.06% | A | G | I | G | T | C | T | T | D | A | A | A | G | C |
| 21.60% | A | G | I | G | T | C | T | T | D | A | A | A | G | C |
| 9.92% | A | G | I | G | T | C | T | T | D | A | A | A | G | C |
| 3.14% | A | G | I | G | T | C | T | T | D | A | A | A | G | C |
| 1.67% | A | G | I | G | T | C | T | T | D | A | A | A | G | C |
| 1.67% | A | G | I | G | T | C | T | T | I | A | A | A | G | C |
| 0.83% | A | G | I | G | T | T | T | T | D | A | A | A | G | T |

| Freq. | Intron1 (−185) | Intron1 (−19) | Intron1 (−12) | Exon2 (−183) | Exon2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) |
|---|---|---|---|---|---|---|---|---|---|---|---|---|---|---|
| 50.06% | A | T | G | A | C | G | T | C | A | G | A | A | T | C |
| 21.60% | A | T | G | G | C | G | C | C | A | G | G | G | T | C |
| 9.92% | A | T | G | A | C | G | C | C | A | G | A | A | T | C |
| 3.14% | A | T | G | A | C | G | T | C | A | G | A | A | T | C |
| 1.67% | A | T | G | A | C | G | C | C | A | G | G | G | T | C |
| 1.67% | A | T | G | A | C | G | C | C | A | G | G | G | T | C |
| 0.83% | A | T | G | A | C | G | C | C | A | G | G | G | T | C |

| Freq. | Intron6 (−55) | Intron6 (−21) | Exon7 (+591) | Exon7 (+630) | 3' FR (+1038) | 3'FR (+1080) | 3' FR (+1243) | 3'FR (+1343) | 3' FR (+1615) | 3'FR (+1649) | 3'FR (+1724) |
|---|---|---|---|---|---|---|---|---|---|---|---|
| 50.06% | C | C | G | C | C | C | A | T | C | T | C |
| 21.60% | C | C | G | C | C | C | A | T | C | T | C |
| 9.92% | C | C | G | C | C | C | A | T | C | T | C |
| 3.14% | C | C | G | C | C | C | A | T | C | T | C |
| 1.67% | C | C | G | C | C | C | A | T | C | T | C |

TABLE 5-continued

GSTO2 Haplotypes for Caucasian-American Population

| | | | | | | | | | | | | |
|---|---|---|---|---|---|---|---|---|---|---|---|---|
| 1.67% | C | C | T | C | T | C | G | T | C | T | C |
| 0.83% | C | C | G | C | C | C | A | T | C | T | C |

*o = observed; i = inferred

TABLE 6

GSTO2 Haplotypes for African-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 16.70% | i | I | T | G | T | G | C | A | C | A | C | G | G | T |
| 14.30% | i | D | T | G | C | C | G | G | C | C | T | G | G | T |
| 14.20% | o | D | T | G | C | C | G | G | C | C | T | G | G | G |
| 6.53% | i | D | T | G | C | C | G | G | C | C | T | G | A | T |
| 5.00% | i | D | T | G | C | C | G | G | C | C | T | G | G | T |
| 4.17% | i | D | T | G | C | C | G | G | C | C | T | G | G | T |
| 3.33% | i | D | C | G | C | C | G | G | C | C | T | G | G | T |
| 3.33% | i | D | T | G | C | C | G | G | C | C | T | G | G | G |
| 3.33% | i | D | T | G | C | C | G | G | C | C | T | G | G | T |
| 2.50% | o | D | T | G | C | C | G | G | C | C | T | G | G | G |
| 2.50% | i | I | T | G | T | G | C | A | C | A | C | G | G | T |
| 1.67% | i | D | C | G | C | C | G | G | C | C | T | G | G | T |
| 1.67% | i | D | T | G | C | C | G | G | C | C | T | G | G | T |
| 1.53% | i | D | T | G | C | C | G | G | C | C | T | G | G | T |

| Freq. | 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) |
|---|---|---|---|---|---|---|---|---|---|---|---|---|---|---|
| 16.70% | T | C | I | T | G | A | G | C | A | C | G | T | A | C |
| 14.30% | C | A | D | C | C | A | C | C | G | A | G | T | A | C |
| 14.20% | C | A | D | C | C | A | C | C | G | A | G | T | A | C |
| 6.53% | C | A | D | C | C | A | C | C | G | A | G | T | A | C |
| 5.00% | C | A | D | C | C | A | C | C | G | A | G | T | A | C |
| 4.17% | C | A | D | C | C | A | C | C | G | A | G | T | A | C |
| 3.33% | C | A | D | C | C | A | C | C | G | A | G | T | T | C |
| 3.33% | C | A | D | C | C | A | C | C | G | A | G | T | A | C |
| 3.33% | C | A | D | C | C | A | C | C | G | A | G | T | A | C |
| 2.50% | C | A | D | C | C | A | C | C | G | A | G | T | A | C |
| 2.50% | T | C | I | T | G | A | G | C | A | C | G | T | A | C |
| 1.67% | C | A | D | C | C | A | C | C | G | A | G | T | T | C |
| 1.67% | C | A | D | C | C | A | C | C | G | A | G | T | A | C |
| 1.53% | C | A | D | C | C | A | C | C | G | A | G | T | A | C |

| Freq. | Intron1 (+52) | Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) |
|---|---|---|---|---|---|---|---|---|---|---|---|---|---|---|
| 16.70% | A | G | I | A | T | C | T | T | D | A | G | A | G | C |
| 14.30% | A | G | I | G | T | C | T | T | D | A | A | A | A | C |
| 14.20% | A | G | I | G | T | C | T | T | D | A | A | A | G | C |
| 6.53% | A | G | I | G | T | C | T | T | D | A | A | A | G | C |
| 5.00% | A | G | I | G | T | C | T | T | D | A | A | A | G | C |
| 4.17% | A | G | I | G | T | C | T | T | D | G | A | A | G | C |
| 3.33% | A | G | I | G | T | C | C | T | D | A | A | A | G | C |
| 3.33% | A | G | I | G | T | C | T | T | D | A | A | A | G | C |
| 3.33% | A | G | I | G | T | T | T | T | D | A | A | A | G | T |
| 2.50% | A | G | I | G | T | C | T | T | D | A | A | A | G | C |
| 2.50% | A | G | I | A | T | C | T | T | D | A | G | A | G | C |
| 1.67% | A | G | I | G | T | C | C | T | D | A | A | A | G | C |
| 1.67% | A | G | I | G | T | C | T | A | D | A | A | A | A | C |
| 1.53% | A | G | I | G | T | C | T | T | D | A | A | A | A | C |

| Freq. | Intron1 (−185) | Intron1 (−19) | Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) |
|---|---|---|---|---|---|---|---|---|---|---|---|---|---|---|
| 16.70% | A | T | G | A | C | G | C | C | A | G | G | G | T | C |
| 14.30% | A | T | G | A | C | G | C | C | A | G | G | G | T | C |
| 14.20% | A | T | G | A | C | G | T | C | A | G | A | A | T | C |
| 6.53% | A | T | G | G | C | G | C | C | A | G | G | G | T | C |
| 5.00% | A | T | G | A | C | G | C | C | A | G | G | G | T | C |
| 4.17% | A | T | G | A | C | G | C | C | A | G | G | G | T | C |
| 3.33% | G | T | G | A | C | G | C | C | A | G | G | G | T | C |
| 3.33% | A | T | G | A | C | G | T | C | A | G | A | A | T | C |
| 3.33% | A | T | G | A | C | G | C | C | A | G | G | G | T | C |

TABLE 6-continued

GSTO2 Haplotypes for African-American Population

| | | | | | | | | | | | | | |
|---|---|---|---|---|---|---|---|---|---|---|---|---|---|
| 2.50% | A | T | G | A | C | G | C | C | A | G | A | A | T | C |
| 2.50% | A | T | G | A | C | G | C | C | A | G | G | G | T | C |
| 1.67% | G | T | G | A | C | G | C | C | A | G | G | G | T | C |
| 1.67% | A | T | G | A | C | G | C | C | A | G | G | G | T | C |
| 1.53% | A | T | G | A | C | G | C | C | A | G | G | G | T | C |

| Freq. | Intron6 (−55) | Intron6 (−21) | Exon7 (+591) | Exon7 (+630) | 3' FR (+1038) | 3'FR (+1080) | 3' FR (+1243) | 3'FR (+1343) | 3' FR (+1615) | 3' FR (+1649) | 3'FR (+1724) |
|---|---|---|---|---|---|---|---|---|---|---|---|
| 16.70% | C | C | G | C | C | C | A | T | C | T | C |
| 14.30% | C | C | G | C | C | C | A | T | C | T | C |
| 14.20% | C | C | G | C | C | C | A | T | C | T | C |
| 6.53% | C | C | G | C | C | C | A | T | C | T | C |
| 5.00% | C | C | G | C | C | C | A | T | C | T | C |
| 4.17% | C | C | G | T | C | C | A | T | C | T | C |
| 3.33% | C | C | G | T | C | C | A | T | C | T | C |
| 3.33% | C | C | T | C | T | C | A | T | C | T | C |
| 3.33% | C | C | G | C | C | C | A | T | C | T | C |
| 2.50% | C | C | G | C | C | C | A | T | C | T | C |
| 2.50% | C | T | G | C | C | C | A | G | C | T | C |
| 1.67% | C | C | T | T | T | C | A | T | C | T | C |
| 1.67% | C | C | T | C | T | C | A | T | C | T | C |
| 1.53% | C | C | T | C | T | C | A | G | C | T | C |

*o = observed; i = inferred

TABLE 7

GSTO2 Haplotypes for Han Chinese-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 55.20% | o | D | T | G | C | C | G | G | C | C | T | G | G | G |
| 13.30% | o | D | T | G | C | C | G | G | C | C | T | G | A | T |
| 12.30% | o | D | T | G | C | C | G | G | C | C | T | G | G | G |
| 6.43% | o | D | T | G | C | C | G | G | C | C | T | G | G | G |
| 1.67% | i | D | T | G | C | C | G | G | C | C | T | G | A | T |
| 1.67% | o | D | T | G | C | C | G | G | C | C | T | G | A | T |
| 1.67% | i | D | T | G | C | C | G | G | C | C | T | G | G | T |
| 1.67% | i | D | T | G | C | C | G | G | C | C | T | G | G | T |
| 1.07% | i | D | T | G | C | C | G | G | C | C | T | G | G | G |

| Freq. | 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) |
|---|---|---|---|---|---|---|---|---|---|---|---|---|---|---|
| 55.20% | C | A | D | C | C | A | C | C | G | A | G | T | A | C |
| 13.30% | C | A | D | C | C | A | C | C | G | A | G | T | A | C |
| 12.30% | C | A | D | C | C | A | C | C | G | A | G | T | A | C |
| 6.43% | C | A | D | C | C | A | C | C | G | A | G | T | A | C |
| 1.67% | C | A | D | C | C | A | C | C | G | A | G | T | A | C |
| 1.67% | C | A | D | C | C | A | C | C | G | A | G | T | A | C |
| 1.67% | C | A | D | C | C | A | C | C | G | A | G | T | A | C |
| 1.67% | C | A | D | C | C | A | C | C | G | A | G | T | A | C |
| 1.07% | C | A | D | C | C | A | C | C | G | A | G | T | A | C |

| Freq. | Intron1 (+52) | Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) |
|---|---|---|---|---|---|---|---|---|---|---|---|---|---|---|
| 55.20% | A | G | I | G | T | C | T | T | D | A | A | A | G | C |
| 13.30% | A | G | I | G | T | C | T | T | D | A | A | A | G | C |
| 12.30% | A | G | I | G | T | C | T | T | D | A | A | A | G | C |
| 6.43% | A | G | I | G | T | C | T | T | D | A | A | A | G | C |
| 1.67% | A | G | I | G | T | C | T | T | D | A | A | A | G | C |
| 1.67% | A | G | I | G | T | C | T | T | D | A | A | A | G | C |
| 1.67% | A | G | I | G | T | C | T | T | D | A | A | A | A | C |
| 1.67% | A | G | I | G | T | C | T | T | I | A | A | A | G | C |
| 1.07% | A | G | I | G | T | C | T | T | D | A | A | A | G | C |

| Freq. | Intron1 (−185) | Intron1 (−19) | Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) |
|---|---|---|---|---|---|---|---|---|---|---|---|---|---|---|
| 55.20% | A | T | G | A | C | G | T | C | A | G | A | A | T | C |
| 13.30% | A | T | G | G | C | G | C | C | A | G | G | G | T | C |
| 12.30% | A | T | G | A | C | G | C | C | A | G | A | A | T | C |
| 6.43% | A | T | G | A | C | G | T | C | A | G | A | A | T | C |

TABLE 7-continued

GSTO2 Haplotypes for Han Chinese-American Population

| 1.67% | A | T | G | G | C | G | C | C | A | A | G | G | T | C |
| 1.67% | A | T | G | G | C | G | T | C | A | G | A | A | T | C |
| 1.67% | A | T | G | A | C | G | C | C | A | G | G | G | T | C |
| 1.67% | A | T | G | A | C | G | C | C | A | G | G | G | T | C |
| 1.07% | A | T | G | A | C | G | C | C | A | G | A | A | T | C |

| Freq. | Intron6 (−55) | Intron6 (−21) | Exon7 (+591) | Exon7 (+630) | 3' FR (+1038) | 3'FR (+1080) | 3' FR (+1243) | 3'FR (+1343) | 3' FR (+1615) | 3'FR (+1649) | 3'FR (+1724) |
|---|---|---|---|---|---|---|---|---|---|---|---|
| 55.20% | C | C | G | C | C | C | A | T | C | T | C |
| 13.30% | C | C | G | C | C | C | A | T | C | T | C |
| 12.30% | C | C | G | C | C | C | A | T | C | T | C |
| 6.43% | C | C | T | C | T | C | A | T | C | T | C |
| 1.67% | C | C | G | C | C | C | A | T | C | T | C |
| 1.67% | C | C | G | C | C | C | A | T | C | T | C |
| 1.67% | C | C | T | C | T | C | A | T | C | T | C |
| 1.67% | C | C | T | C | T | C | A | T | C | T | C |
| 1.07% | C | C | T | C | T | C | A | T | C | T | C |

*o = observed; i = inferred

TABLE 8

GSTO2 Haplotypes for Mexican-American Population

| Freq. | o/i* | 5'FR (−2012) | 5'FR (−1785) | 5'FR (−1771) | 5'FR (−1664) | 5'FR (−1598) | 5'FR (−1576) | 5'FR (−1566) | 5'FR (−1541) | 5'FR (−1357) | 5'FR (−1189) | 5'FR (−1179) | 5'FR (−1105) | 5'FR (−1102) |
|---|---|---|---|---|---|---|---|---|---|---|---|---|---|---|
| 60.70% | o | D | T | G | C | C | G | G | C | C | T | G | G | G |
| 16.70% | o | D | T | G | C | C | G | G | C | C | T | G | A | T |
| 6.84% | o | D | T | G | C | C | G | G | C | C | T | G | G | G |
| 3.51% | i | D | T | G | C | C | G | G | C | C | T | G | A | T |
| 1.67% | i | D | T | G | C | C | G | G | C | C | T | G | G | T |
| 1.49% | i | D | T | G | C | C | G | G | C | C | T | G | A | T |

| Freq. | 5'FR (−1009) | 5'FR (−781) | 5'FR (−730) | 5'FR (−637) | 5'FR (−634) | Exon1 (−625) | Exon1 (−530) | Exon1 (−526) | Exon1 (−463) | Exon1 (−450) | Exon1 (−424) | Exon1 (−410) | Exon1 (−293) | Exon1 (−234) |
|---|---|---|---|---|---|---|---|---|---|---|---|---|---|---|
| 60.70% | C | A | D | C | C | A | C | C | G | A | G | T | A | C |
| 16.70% | C | A | D | C | C | A | C | C | G | A | G | T | A | C |
| 6.84% | C | A | D | C | C | A | C | C | G | A | G | T | A | C |
| 3.51% | C | A | D | C | C | A | C | C | G | A | G | T | A | C |
| 1.67% | C | A | D | C | C | A | C | C | G | A | G | T | A | C |
| 1.49% | C | A | D | C | C | A | C | C | G | A | G | T | A | C |

| Freq. | Intron1 (+52) | Intron1 (+152) | Intron1 (+310) | Intron1 (+311) | Intron1 (+333) | Intron1 (+402) | Intron1 (+426) | Intron1 (+435) | Intron1 (+477) | Intron1 (+1694) | Intron1 (+2003) | Intron1 (+2146) | Intron1 (+2168) | Intron1 (−1131) |
|---|---|---|---|---|---|---|---|---|---|---|---|---|---|---|
| 60.70% | A | G | I | G | T | C | T | T | D | A | A | A | G | C |
| 16.70% | A | G | I | G | T | C | T | T | D | A | A | A | G | C |
| 6.84% | A | G | I | G | T | C | T | T | D | A | A | A | G | C |
| 3.51% | A | G | I | G | T | C | T | T | D | A | A | A | G | C |
| 1.67% | A | G | I | G | T | T | T | T | D | A | A | A | G | T |
| 1.49% | A | G | I | G | T | C | T | T | D | A | A | A | G | C |

| Freq. | Intron1 (−185) | Intron1 (−19) | Intron1 (−12) | Exon2 (−183) | Intron2 (−16) | Exon3 (+121) | Intron4 (+20) | Intron4 (+39) | Intron4 (−38) | Exon5 (+389) | Exon5 (+424) | Intron5 (+74) | Intron5 (+170) | Exon6 (+472) |
|---|---|---|---|---|---|---|---|---|---|---|---|---|---|---|
| 60.70% | A | T | G | A | C | G | T | C | A | G | A | A | T | C |
| 16.70% | A | T | G | G | C | G | C | C | A | G | G | G | T | C |
| 6.84% | A | T | G | A | C | G | C | C | A | G | A | A | T | C |
| 3.51% | A | T | G | A | C | G | T | C | A | G | A | A | T | C |
| 1.67% | A | T | G | A | C | G | C | C | A | G | G | G | T | C |
| 1.49% | A | T | G | A | C | G | C | C | A | G | A | A | T | C |

| Freq. | Intron6 (−55) | Intron6 (−21) | Exon7 (+591) | Exon7 (+630) | 3' FR (+1038) | 3'FR (+1080) | 3' FR (+1243) | 3'FR (+1343) | 3' FR (+1615) | 3'FR (+1649) | 3'FR (+1724) |
|---|---|---|---|---|---|---|---|---|---|---|---|
| 60.70% | C | C | G | C | C | C | A | T | C | T | C |
| 16.70% | C | C | G | C | C | C | A | T | C | T | C |
| 6.84% | C | C | G | C | C | C | A | T | C | T | C |
| 3.51% | C | C | G | C | C | C | A | T | C | T | C |
| 1.67% | C | C | G | C | C | C | A | T | C | T | C |
| 1.49% | C | C | G | C | C | C | A | T | C | T | C |

*o = observed; i = inferred

TABLE 9

Summary of GSTO2 haplotypes

| | AA | CA | HCA | MA | 5'FR (−2012) | 5'FR (−1785) | 5'FR (−1771) | 5'FR (−1664) | 5'FR (−1598) | 5'FR (−1576) | 5'FR (−1566) | 5'FR (−1357) | 5'FR (−1189) | 5'FR (−1105) | 5'FR (−1102) | 5'FR (−1009) | 5'FR (−781) | 5'FR (−730) | 5'FR (−637) | 5'FR (−634) | Exon1 (−530) | Exon1 (−463) | Exon1 (−450) | Exon1 (−293) | Intron1 (+311) | Intron1 (+402) | Intron1 (+426) | Intron1 (+435) | Intron1 (+1694) | Intron1 (+2003) | Intron1 (+2168) | Intron1 (−1131) | Intron1 (−185) | Exon2 (−183) | Exon3 (+121) | Intron4 (+20) | Exon5 (+389) | Exon5 (+424) | Intron5 (+74) | Exon6 (+472) | Intron6 (−21) | Exon7 (+591) | Exon7 (+630) | 3' FR (+1038) | 3'FR (+1343) |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1 | 0.17 | — | — | — | I | T | G | T | G | C | A | A | C | G | T | T | C | I | T | G | G | A | C | A | A | C | T | T | A | G | G | C | A | A | G | C | G | G | G | C | C | G | C | C | T |
| 2 | 0.14 | — | — | 0.01 | D | T | G | C | C | G | G | C | T | G | T | C | A | D | C | C | C | G | A | A | G | C | T | T | A | A | A | C | A | A | G | C | G | G | G | C | C | G | C | C | T |
| 3 | 0.07 | 0.22 | 0.13 | 0.16 | D | T | G | C | C | G | G | C | T | A | T | C | A | D | C | C | C | G | A | A | G | C | T | T | A | A | G | C | A | G | G | C | G | G | G | C | C | G | C | C | T |
| 4 | 0.05 | — | — | — | D | T | G | C | C | G | G | C | T | G | T | C | A | D | C | C | C | G | A | A | G | C | T | T | A | A | G | C | A | A | G | C | G | G | G | C | C | G | C | C | T |
| 5 | 0.04 | — | — | 0.01 | D | T | G | C | C | G | G | C | T | G | T | C | A | D | C | C | C | G | A | A | G | C | T | T | G | A | G | C | A | A | G | C | G | G | G | C | C | G | T | C | T |
| 6 | 0.03 | — | — | — | D | C | G | C | C | G | G | C | T | G | T | C | A | D | C | C | C | G | A | T | G | C | C | T | A | A | G | C | G | A | G | C | G | G | G | C | C | G | T | C | T |
| 7 | 0.03 | 0.01 | 0.01 | 0.01 | D | T | G | C | C | G | G | C | T | G | T | C | A | D | C | C | C | G | A | A | G | T | T | T | A | A | G | T | A | A | G | C | G | G | G | C | C | G | C | C | T |
| 8 | 0.03 | 0.01 | 0.01 | 0.01 | D | T | G | C | C | G | G | C | T | G | T | C | A | D | C | C | C | G | A | A | G | T | T | T | A | A | G | T | A | A | G | C | G | G | G | C | C | G | C | C | T |
| 9 | — | 0.03 | — | 0.01 | D | T | G | C | C | G | G | C | T | A | T | C | A | D | C | C | C | G | A | A | G | C | T | T | A | A | G | C | A | A | T | G | A | A | C | C | G | C | C | T |
| 10 | 0.03 | — | — | — | I | T | G | T | G | C | A | A | C | G | T | T | C | I | T | G | G | A | C | A | A | C | T | T | A | G | G | C | A | A | G | C | G | G | G | C | T | G | C | C | G |
| 11 | 0.02 | — | — | — | D | C | G | C | C | G | G | C | T | G | T | C | A | D | C | C | C | G | A | T | G | C | C | T | A | A | G | C | G | A | G | C | G | G | G | C | C | T | T | T | T |
| 12 | 0.02 | — | — | — | D | T | G | C | C | G | G | C | T | G | T | C | A | D | C | C | C | G | A | A | G | C | T | A | A | A | G | C | A | A | G | C | G | G | G | C | C | T | C | T | T |
| 13 | — | — | 0.02 | 0.01 | D | T | G | C | C | G | G | C | T | G | T | C | A | D | C | C | C | G | A | A | G | C | T | T | A | A | A | C | A | A | G | C | G | G | G | C | C | T | C | T | T |
| 14 | 0.02 | — | — | — | D | T | G | C | C | G | G | C | T | G | T | C | A | D | C | C | C | G | A | A | G | C | T | T | A | A | A | C | A | A | G | C | G | G | G | C | C | T | C | T | G |
| 15 | 0.01 | — | — | — | D | T | C | C | C | G | G | C | T | A | T | C | A | D | C | C | C | G | A | A | G | C | T | T | A | A | G | C | A | G | A | C | G | G | G | C | C | T | C | T | T |
| 16 | — | — | 0.02 | — | D | T | G | C | C | G | G | C | T | A | T | C | A | D | C | C | C | G | A | A | G | C | T | T | A | A | G | C | A | G | G | C | A | G | G | C | C | G | C | C | T |
| 17 | 0.14 | 0.5 | 0.55 | 0.61 | D | T | G | C | C | G | G | C | T | G | G | C | A | D | C | C | C | G | A | A | G | C | T | T | A | A | G | C | A | A | G | C | G | G | G | C | C | G | C | C | T |
| 18 | 0.03 | — | 0.06 | — | D | T | G | C | C | G | G | C | T | G | G | C | A | D | C | C | C | G | A | A | G | C | T | T | A | A | G | C | A | A | G | T | G | A | A | C | C | T | C | T | T |
| 19 | 0.03 | 0.1 | 0.12 | 0.07 | D | T | G | C | C | G | G | C | T | G | G | C | A | D | C | C | C | G | A | A | G | C | T | T | A | A | G | C | A | A | G | T | G | A | A | C | C | G | C | C | T |
| 20 | — | 0.01 | — | — | D | T | G | C | C | G | G | C | T | G | G | C | A | D | C | C | C | G | A | A | G | C | T | T | A | A | G | C | A | A | G | C | G | A | A | A | C | G | C | C | T |

Example 4

Immunoreactivity of GSTO2 Allozymes

As an initial step in the study of the possible functional implications of nonsynonymous cSNPs in the GSTO2 gene, expression constructs were created for all variant allozymes, and those constructs were used to transfect COS-1 cells. This mammalian cell line was transfected to ensure the presence of mammalian post-translational modification and the mammalian machinery for protein degradation. The GSTO2 expression constructs were cotransfected with β-galactosidase to make it possible to correct for variations in transfection efficiency. The antibodies for GSTO2 were directed against peptides that did not include any of the genetically variant amino acids. When GSTO2 constructs were transiently expressed in COS-1 cells, levels of the Cys130Tyr13 and Leu158Ile allozymes, as well as the double variant Asn142Asp/Leu 158Ile allozyme, were strikingly reduced. The Val41Ile and Asn142Asp allozymes were expressed at approximately 80% of the level of the WT allozyme (Table 10). The GSTO2 antibody cross-reacted with a protein in the COS-1 cells with a molecular mass slightly higher than that for recombinant GSTO2.

Attempts were made to complement expression studies with parallel assays of level of enzyme activity, but the assays currently available for GSTO2 activity-assays that have been used to study purified, bacterially expressed protein (Schmuck et al. (2005) *Pharmacogenet Genomics* 15:493-501)—lacked the sensitivity necessary for application to the cultured mammalian cell cytosol preparations.

TABLE 10

GSTO2 immunoreactive protein levels

| | |
|---|---|
| WT | 100 ± 2.3 |
| Val41Ile | 82.8 ± 1.6 |
| Cys130Tyr | 49.4 ± 2.8 |
| Asn142Asp | 76.1 ± 3.0 |
| Leu158Ile | 17.3 ± 1.7 |
| Asn142Asp/Leu158Ile | 15.2 ± 2.5 |

Example 5

GSTO2 Degradation Studies

To investigate the mechanisms responsible for the striking decrease in expression of the GSTO2 Cys130Tyr and Leu158Ile allozymes, protein degradation studies were performed using RRL. Radioactive WT and variant GSTO2 allozymes were synthesized using "treated" RRL, and the recombinant proteins were incubated for various periods of time with "untreated" RRL and an ATP generating system to follow the time course of protein degradation. The CYS130Tyr, Leu158Ile, and Asn142Asp/Leu158Ile allozymes were degraded much more rapidly than WT GSTO2, with Leu158Ile and Asn142Asp/Leu158Ile being degraded more rapidly than Cys130Tyr (FIG. 3). After 24 hours, 26% of Cys130Tyr, 6.6% of Leu158Ile, 5.6% of Asn142Asp/Leu158Ile, and 73% of the WT protein remained. Therefore, accelerated degradation appeared to be responsible, at least in part, for differences in levels of the GSTO2 variant allozymes after expression in COS-1 cells.

Example 6

Activity and Substrate Kinetics of GSTO2 Allozymes

Cell homogenate preparations containing recombinant GSTO2 allozymes, prepared as described in Example 1, are used to assess catalytic activity. The resulting activities are adjusted to a percentage of the WT GSTO2 enzyme activity. To determine whether alterations in activity of the GSTO2 variants might be related to quantity of immunoreactive enzyme protein, quantitative Western blot analyses are conducted.

Alterations in amino acid sequence can alter enzyme substrate affinity and/or catalytic efficiency. Substrate kinetic studies are conducted to determine whether the allozymes differ from the WT GSTO2 protein in these aspects. A series of DHA concentrations are used to estimate apparent $K_m$ values for recombinant wild type GSTO2 and for the variant allozymes.

Example 7 mRNA Levels of GSTO2 Allozymes

RT-PCR was used to determine whether differences in protein levels were due to differences in mRNA levels. To evaluate the mRNA level after transient expression of GSTO2 WT and one or more GSTO allozymes, RT-PCR is performed using mRNA isolated from transfected COS-1 cells. β-Galactosidase is used to correct for transfection efficiency and also as an internal control for RT-PCR.

Example 8

Reporter Assays

Luciferase reporter assays are conducted to determine whether polymorphisms in the 5'-FR affect transcription of GSTO2 allozymes. Reporter gene constructs including commonly occurring haplotypes (e.g., haplotypes with an allele frequency greater than 3%) are created within the first 1 kb upstream of the translation initiation codon. These constructs are transfected into primary cells or cell lines such as liver, kidney, skeletal muscle, heart, lung, cervix, ovary, or prostate cells. After incubation for 48 hours, cells are harvested and lysed, and luciferase activity is measured using a dual-luciferase assay system.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated glutathione S-transferase omega 2 (GSTO2) polypeptide, wherein said polypeptide comprises an amino acid sequence which differs from SEQ ID NO:9 solely by a modification selected from the group consisting of (a) an amino acid substitution at position 41 of SEQ ID NO:9, (b) an amino acid substitution at position 130 of SEQ ID NO:9, (c) an amino acid substitution at position 158 of SEQ ID NO:9, and (d) any combination of (a)-(c).

2. The isolated polypeptide of claim 1, wherein (a) the amino acid at position 41 of SEQ ID NO:9 has been replaced with isoleucine, (b) the amino acid at position 130 of SEQ ID NO:9 has been replaced with tyrosine, (c) the amino acid at position 158 of SEQ ID NO:9 has been replaced with isoleucine, or (d) any combination of (a)-(c).

* * * * *

SEQUENCE LISTING

<160> NUMBER OF SEQ ID NOS: 47

<210> SEQ ID NO 1
<211> LENGTH: 30639
<212> TYPE: DNA
<213> ORGANISM: Homo sapien

<400> SEQUENCE: 1

| | | | | | |
|---|---|---|---|---|---|
| cacaaaggcc | tcctgccgca | aaccttcagc | ggccaccaaa | gccccggctg | ccggcggcgg | 60 |
| accacctctg | ctgccgcgcg | cctaccggag | ccgcttggcc | ctagtgcttt | ccagcggatt | 120 |
| tcccctcagg | tgcggagccg | ggtgccgggg | tcccacagcc | aaccactacc | ggttcctctt | 180 |
| tcgtcagcca | ccggcgccgg | caggacccgc | gaatcccgat | ctccaggagc | ctgtaaggag | 240 |
| gccgcccatt | ggctcagccg | cactgctggg | caggtacttc | caaagctttg | aggattggct | 300 |
| gatgctctgg | gcgccgggc | tagttggcgg | gtaggatcac | gtgcgagggg | caggccccgt | 360 |
| ctaggccccg | cctccttgct | gctgctgccg | ccgccaatcc | tggtccggtt | gcccgagttc | 420 |
| ccggaggtct | ctcgcgggac | ctctctcacc | gccaccggtg | ggtccgttcg | gctgcgttg | 480 |
| tattggaagg | gaagagggt | ttgaggtcaa | ttctgtttcc | tggggttttc | acgaatttcg | 540 |
| gggcccacag | taggcttgcc | aactttaact | tttgcctaac | actttacgag | aaatcctatt | 600 |
| tagccttggc | cactgttgca | tcaaagaatt | tcacatccaa | caaagtgcag | cctaagaata | 660 |
| aagaacaggt | cttaaaccg | cataccttta | attaaggtgt | tcttattttt | tctgatttgg | 720 |
| ctggaaacag | gcagagacca | ccccagataa | ccagttctca | gccttgcgtg | ggacaccacg | 780 |
| agtcccacgt | gtttacgtgt | ttaaggcact | ggcaagcagg | ggaatttggt | ttctgggaat | 840 |
| gtgctgtctt | tgtgaaaact | gtgaaaagtc | ttccctgcta | cattgaaata | atcataaaat | 900 |
| aataatagct | aatgttgaac | acttactatg | tatcagacac | atgctaagca | ttcaatattt | 960 |
| ctcatccagt | ttctgaatga | aaccttcgca | aaccacataa | tgtactggta | ctattagcta | 1020 |
| cgaattacat | ataagaacac | ccgaaagttg | ttgtcatttg | cccaaggtca | cccagctaat | 1080 |
| aaatattgaa | gagattcgaa | tctagcctga | actcttacag | taagaccgtt | cgtgagatga | 1140 |
| atttatatgt | gctattttc | cagtctcttt | atccaacagc | tctgacagag | gatagtatct | 1200 |
| accttttttt | ttttttttg | agacggagtc | tcgctgttct | gcccaggccg | gactgcagtg | 1260 |
| gcgcgatctc | ggctcactgc | aagctccgcc | tcccgggttc | acgccattct | cctgcctcag | 1320 |
| cctcccaagt | agctgggact | acaggcgccc | gccaccgcgc | ccggctaatt | ttttgtattt | 1380 |
| ttagtagaga | cggggtttca | ccgtgttagc | caggatggtc | tcgatctctt | gacctcgtga | 1440 |
| tccgcccgcc | tcagcctccc | aaatcgctgg | gattacaggc | gtgagccacc | gcgcccggcc | 1500 |
| tgtatctgcc | tttttgacca | caccattatt | cgtgggattt | aacaggagtt | aatgagttaa | 1560 |
| taatgttcct | tttccaaact | cagtggtttt | gattttacaa | attatttgac | ttttcctgat | 1620 |
| ttcaggatct | tgacaatttg | cctttactta | ttcaaatgtt | attataccaa | atatttattt | 1680 |
| aaaaagtttt | ttttttcttt | gattcctcaa | gttgtagaga | gaaatagga | tagggaagca | 1740 |
| gaatcaagta | gttaaaaaga | tagcctcatt | tgaccctgat | ttcccaattg | ggaatatgaa | 1800 |
| atttttcctg | aatataagca | catttgagaa | tagaaccttt | tacctaacgt | atctcacttt | 1860 |
| ttgaactcat | tggacaataa | gggaacaccc | agtaatataa | tctttcatat | aaattaggct | 1920 |
| tctaacttat | taagaggaat | gtactccagt | ccagttctg | ctactatcaa | gagatggcgt | 1980 |
| gacaaaaaat | tttgaaaagt | tgccgaatgc | aaaccacagt | tcctcttctc | aaaacaaatg | 2040 |

```
catgtaaata gagtgtaagc tatttctttg gtggcattat tttcctagaa ggcttaagtc   2100
gttaatcacc catgaccgaa gatccaaaca ttttcaaagc agatccgatc atatttcagg   2160
tggctgaaaa tggatttgga gtaggtttaa tatggtctac ttacaatttg tttcatgatt   2220
gagtgggtca gtataataaa ggtataaaca tgaaataaca tagaaggaaa gtttgcaaag   2280
aggatttcaa agaagtacct gttgggtatt caaaagaaag tagggataag cttaaggtta   2340
aaatctttct agggaaagta tagtgttcag aggtaagatt aaaaaccaca ttactgaaat   2400
ggagtctgca gcattcagcc cattcaattg gcattaaact ggtaactggt gaaataagta   2460
ttgtgagttg aactttaatt ctaatatgct tggcaaagcc gaatcacagt gtgcttcatc   2520
tttgtggata caaaattgga atgcactctg ctatttaaaa tgtgttctta ctcactagcg   2580
tttgtcatta actttgacgt atactgagct cttactatac tgacgatgcc ctggactatt   2640
tgattcgata ctcacaattc ataaagtagg tattattggt gttctcattt tgcaggtgag   2700
gaaagtgaaa tccaaaaagg ttagatagct tgcctaagtg ccaaagctgg gtctcaaaaa   2760
gtcagcccat tgggctccag ggcctgttct gagaaccttg acactagatt gtttcccttt   2820
agaggagaac agcttccatc cctgtcttct aactctacca aattaacttg gcatttcaga   2880
acttgatttc ccacatacag atacactttt catgaacatt tcccaactct cagagttagt   2940
ttcttttaaa aggtgggaat gaaaaaacaa aacttggaaa atcatcctct tctggcaaag   3000
tagaaaggtg gatccaggaa cctttttaatt tacaaatgga attcccagtt tggccattat   3060
ccagagacca tggatgggca aattaaggcc attgggctaa atccaaccaa ttgttggttt   3120
ttttatagct caatatctaa gaatgatttt ttacattttt aaagggttga aaaagaaaaa   3180
ccagtcacaa cgtgatatgt gaaaattata tgaaattcac caagagtgag ccctaatata   3240
ttaactatgg atgttgggtg ataatatgtc aatgtgggtt cattgattgt aataaatgta   3300
cctctctgat tggaatattg atagtggaag agactgtgca tgtgcggggg cacagggtat   3360
atgggaaatg tgtattttct gctcaatttt gctgtgaatc taaaactttt ttttaaaaaa   3420
aggctattaa aatacatata tgcagttcaa attcagtgtg tccataaata cagccacacc   3480
catttgttta tttatcatcg atggctgttt ttacactaca agtgtagaac taaatagtgg   3540
agaccagatg gcctgaaaag cctgaaatat ttaatatatg taaaaacatt tgccaatcat   3600
tcagttcatg gcatctgata aagactaaga tactggttga gattgttgcc gctggagtca   3660
aacttccagg gttcctagtc ctccctcttt cacttactag ttgagaagtg cttaactatg   3720
ctagtctcag tttactcatc ttttaaagtg aatcaaaata gaacagttat gggacttttt   3780
tttttttttt tttttttttt tttttttttt tttttttttg agacgagtc tcgctctgtc   3840
gcccaggctg gagtgcagtg gcgcagtctc ggctcacagc aagctccgcc tcccgggttc   3900
acgccgttct cctgcctcag cctcctgagt agctgggact acaggcgcct gccaccgcgc   3960
ccggctaatt tttgtgtttt tagtagagac ggggtttcac cacgttagcc aggatggcct   4020
caatctcctg acctcgtgat ccgcccgcct cggcctccca aagtgctggg attacaggca   4080
tgagccaccg cacccggccc agttattgga ctattttaag aattaactgg gtcaatacac   4140
atgaagcacc aaatatatat tagtaataat ttattttgat tttgagattt tgcaaccctc   4200
ttatggcctt ttttaggcta tggatatatt tttctcaact atcttgaaat ctgctttttt   4260
tatatgaggg atgcatgtgt atgcccagaa gtcatcttac ctaccaggag ctctaagatg   4320
acatggttgt gtttcttgct tctatttttac catccaattt gtccttcttg atcagaatta   4380
```

```
gctccaaagt agtagaagtt actctgttac tttctctgtc ttcttaaatg aaaagttgtc    4440
agcgtagcaa gccgggaacc aatatgtctt ctccaacacc agatttcttg ctgacatata    4500
tgcattttat tttcagagaa catttattca aacattttg ccattccctg attcttataa     4560
aatgttaata ctttccatat tattatctaa gcttatttca catgaaatca ttgaatgaca    4620
gcaaaaaatg tagttgagtc actattctga agatttgcaa agattcttat tcactagcaa    4680
aaaatgttaa cactattatt aaccaagaag ttctggatag actggaattc caaaggccaa    4740
acagtaccca gttataagct acataattag gctctgtcat tttaataaaa gatatttaga    4800
ttcaagtatt atttgttgag cagccattac gtgctatatc ttttcctgga cttaaaatcc    4860
tttcctccta acactattac cagttttaaa ggtcaagaca acgagtcaag ctttggactt    4920
ttaaagttct tcaaccctac tagctggtca ctttgggcaa ataatttcat ttttctgaag    4980
ctgttttctg ttttgaaaag tagaaataat atgagttgcc tgactgagca attgtaggaa    5040
tcaaggtaat ctatggaaat aatttagtca gtatgagtga gacacagaaa atatttttct    5100
ttccttcatg atctgttaat cctacaaaat gcatttacaa gcaattccca catcagctca    5160
attctggaaa atttaaggaa ttattttttt acctgctgaa attcaggatc tcagcttatc    5220
agcatcagag ccaaagccac gtctattatc tcacgtaaac agaaaagctg tgcaagtcgc    5280
ccctatatgg ctgggctgtt ggcaatgtat ccttggcaac tagtaagagt gttctcaaaa    5340
atttatgctg gggaacgggg gaagctcaca aattgttctt tgcctccagg tatcttaatt    5400
ttattcattg ccagttttc agagcttggg taaaatctca caagtagggc caggactggg     5460
atgaggcaac tgaggtgtct agggtgcaaa atgtgagttg tctagacacc aaagttgtct    5520
aggtgtctag gaggcactca ctctctgggg tatgtgagat ttcaacacca atgacttttt    5580 cttttcctagt tgctgtatca tgagaatgtt tggccttatt attttttaaa gctgtactta    5640
cttaccaaag agtggccagt ttagtgatgc aagagattca gaatgggaaa aaaaaagtca    5700 gctttacccct agtcagtttt gattaaactc ctttgaaatc catgttggag tttaaatgcc    5760
cattcttgag ggattcttga tgtagaggag ccccctccaa agctttaagc acatgtccag    5820
agcaaggggg agcttttctg gtgttatttt gtcttgtttt gttttttgcc agctcctact    5880
ctcgggcttc caaatctggg gcgatgtctc cccaggttaa attaccctag ctcctgctcc    5940
agatcgcttc cccgtgcccc gccagagccc agtagttcaa aaattaaatt tggggcaagg    6000
ggtgcgcgcc agagcgcagc tgtttctgga gcctgcggca gcggtggcga gccacagggc    6060
ggcgaccgtg agctccggga gctgcgcaaa ccacctggag accatgtctg gggatgcgac    6120
caggaccctg gggaaaggtg agtgctctcc atggggtccg cgagctgggg gcgccgcgtg    6180
acagaaaatg ttggcttcgg cggagctgcc tggccttggc ctgcagaccg gcggggcagg    6240
aagggacttg gagggctctc ctgaagaaaa gccacatgca gcactgccct ctctgggact    6300
tgggagttgg agctccccaca gccatcttgg gatctgggca agtgagcgag ctccttcctc    6360
accgggctga ctagcctctc ctttccctgt cccctccat cgctgctctg caggaagcca    6420
gcccccaggg ccagtcccgg agggggctgat ccgcatctac agcatgaggt tctgcccccta    6480 ttctcacagg acccgcctcg tcctcaaggc caaagacatc aggtgagaag cgggaaccca    6540 gagccccga gcaaacccag cgcctcacag gagcccggga atgtttaaca tctgggcgc      6600 cctgctcagc ttttacaagg ggctccctgt ccctttttc ggaggcaaag tcaacaaata    6660
gcaaggggcg agcttttttt tagcgggccc tactgaaatg cggagccctt ttccgagtca    6720
cgcctatgca tgaaacttct agcccagcgc agagtaatgt gaatgatggg gctggtgaac    6780
```

```
tggttccctc ccagaatgtt taagggcaca gccaacacta ctgaggcctt acctgactgc   6840
tccacagagg tagttccccc accacacccc aggcatctta ggtcactgtt tcctttcttt   6900
attgaactta ctgcatccag cattttctta tttgttcatc catctcccct ccccagtccc   6960
cttcacccat gtgcgttctc gagggtagga actctgtctc ttttattcat gagctaggag   7020
agagcctgtc acatagtgga tgctcaaaaa acatctgtta aatgaatgaa caaatctttc   7080
caaacaatga aatagaagga attgctatca agaggtgtct ggaagttttc aagacacctt   7140
gaaaacttga gaaatgggta cagatgcttc caaaaggaag tttgcaaaac cagctcctgc   7200
aggtctggat ttggagggca gagcagcttt gctgggatgt ggactgcata atgcagctgg   7260
cctccaagct agagtgttga gaatatgtca ctccaggctc ccgactcttg tctcggagag   7320
tccatcacaa gggggtgact tcagagtttc agactcatgt cagagagata caaagactaa   7380
tacagagatg ttttaaataa aattatgtaa atctgccttg ttgagtatat agggcctgta   7440
tttccacatt cttccctttt gctcaaatta agctgacctt aaggttacct gttttttgag   7500
gaaaataaca acaactggat gttttgccca tttggtgata aattatcagc ttaggagctg   7560
atgtatttcc ttaggtcagc gtttctcaaa cttggcactg ttgacagttt aggccagata   7620
attctttgtt ggagaggtgg gatagaagct gtcctgtcca tcactggatg tttagcagta   7680
tccttggtct ctacccattc aatgacagta gagtccccct tccctatgca ctaccttcag   7740
ttgtgacaac aaaaccatgt ctccagacat agtgatatgt cccttgggaa ggaggccaaa   7800
aatcacttct agtcgagacc cattgcttta ggttgagacc cactgcttta ggtcttgcta   7860
tgtggcctat gctggtctcg aaatcttggg ctcaagcaat cctcccaccc tggcctctca   7920
aagtgctgag attacaggtg tgagccacct catccagcct ctgctgtagg tttaagacaa   7980
tctcctagac taagcaatga acgttcccat ttgtttcctt tcatgttttt aaacatacgt   8040
tcatgcttct ggtaactata tagttatcta aataataatt gtattatgtg aacattaaat   8100
aataatagta ttatttgaac atctaataat tagaagaaga attaaaaaag ttattgcatg   8160
cttatgtgcc aggcactgtc ctaaacactt tatacatatc cccaccacag taccaagaga   8220
tgggtgtaat tattagcccc attttataat taaggacact gagcacagag aggttaggaa   8280
ttcggttaag gtcccaagct agaccgttta ttctgatgcc aaaactcata ctcttaattg   8340
ttaacattta ccatattctg ttgtgacctg ttaataccag atttgtattt tcaagctgta   8400
gaatgtacta aactctctaa tgccatggtt aagtgtgtga gctctgagtc tgtctgcctg   8460
gctgtgatct tggctctact actttttttt tttttttagat ggagtttctt gcccaggctg   8520
gagtacagtg gtgtaatctc agctcactgc aacctccacc tcccgggttc aagcaattct   8580
cctgcctcag tctcccaagt agctggggtt acaggcgccc gccaccatgc ctggctactt   8640
ttttgtattt tttagtagag atgggggtttt gccatgttgg ccaggcaggt cttgaattcc   8700
tgacctcaga tgatctgccc gccccagcct cccaaagtgc tgggattaca ggtgtgaggc   8760
accgcgcccg gccagctcta ctacttctta gtgggtggta ttgggtgtga gattcaaccc   8820
ccttgagtct tctttcctat gaggtgagcc tacttcaggg ggaattatga ggaacaactg   8880
agataaggca tggaaaacat ccgacacatc ttactgcagg aaggaagatg atgatgttat   8940
gtattttata caaaacttaa accttaaaac actaattgca aattttaact tttaaactga   9000
ttgcttctgc tttcaagaag agtgcctgcc tgcagatgcc tctcattttt gttctgtctt   9060
gttttccttt tgctttttaa gacatgaagt ggtcaacatt aacctgagaa acaagcctga   9120
```

```
atggtactat acaaagcacc cttttggcca cattcctgtc ctggagacca gccaatgtca    9180
actgatctat gaatctgtta ttgcttgtga gtacctggat gatgcttatc caggaaggaa    9240
gctgttttcca tatgaccctt atgaacgagc tcgccaaaag atgttattgg agctattttg    9300
taaggtatat tcaatttaaa aagtcactca cactgtattt tactttgcat gtctttccca    9360
aacctcaacc cattttaaag ccaaatcatt ggtgaaactg ttttgttttg ataccatgtg    9420
atcctcagga gattagctag catggaatta gggtagagca tggccactga tattaaaggc    9480
ttaactgcta ggcgcttctc catttcaact ggcaggctca ggaggtatgg ttatgacatg    9540
gcaatgaccg tgtaacttga agcaggaata ctgaaagaac tgaaaactgg tgatccttaa    9600
agggagtatt tctccagctt caggtaaaaa gtaatggagt gcgaagatta tgcatagaag    9660
gtgatgcttt tttattattt tttttttgag acggagtctc gctctgtcac ccaggctgga    9720
gtgcagtggc accatctcgg ctcactgcaa cctctgccac ctgggtttaa gcaattttcc    9780
tgcctcagcc tcctgagtag ctgggattac aggcgcatgc caccacaccc cctaattgtt    9840
gtattttttag tagagatggg gtttcaccat attggccagg ctggtcttga actcctgacc    9900
tcaagtgatc tgcctgcctc ggcctcccaa agtgctagga ttacagacgt gagccactgt    9960
gcctggccag tgatgctctt tagaagcata agagtgcctg ctgtccagga aatgtgaaga   10020
atagataaat ggtggcagct ttgataatga aagaaaaaag aatggagaaa ttttaagatg   10080
gtgtctttga aaaggaattt ttaaaaacct caatgatatt aacagctgac atatatcgaa   10140
cacttatgat gtgccaggca ctgtcctagt tactttgtag gagctaactc atttaatcca   10200
actgcccttt gaagtgggta ctgctatcgt atccattttt cagatgagaa cactgaggct   10260
tagagaggtt gagtgtccca cctaagaatg tatagcatgg aagcagctga tcaagtaagg   10320
agcactggag aaaccctcct aaagcaccct gctttcccag ggtactataa gaagtagatt   10380
cctactgaga accggaacca cagagaaaac ctagtgcctc tcacagggag ctgggggtc    10440
tgatgtgggt gttgccctgt taggctggag ttataaagct tcgctgcctt ttcaggcaga   10500
acaggaactg gaagtttcca cagacttctc cactgagaac ctgtgtcctc tgattaggtc   10560
ccacatttga ccaaggagtg cctggtagcg ttgagatgtg ggagagaatg cactaatctg   10620
aaggcagccc tgcgtcagga attcagcaac ctggaagagg tacaaaaagg ggtccctctc   10680
ctggtcagct acagtggagg aagctaggca gggtcgctaa cctggtcact ctaacaccag   10740
ctttcacagg cttattcttt ctgcctttga taagtcagac ttctgatcat ctgattgcat   10800
gtttgccctc ctctaacctg gtctagaatt attctggaaa atctgatgag gagttgggga   10860
ggacatgcca tgaattgctt ccttttccag agtcacccca tctccctgag tagctctgca   10920
tggcttctgt agcttctgcc aatgaggtca aggtctgtaa aggttagggg ttgtgtttgg   10980
ctgctgaagt ctaactactg taaattcatg ttgtaagggt ttactctctc acataacatt   11040
ctttctcacg tattataagg gttattctc acacatacgg tggctcacac ctgtgatccc    11100
agcacttggg gaggctgaag caggaggatc acttgagcct agaagtttaa gaccagccta   11160
ggcaacatag caagacccct cctctacaaa aataattttta aaaattagcc aggcataacg   11220
atgtataacct gtagtcccag ctacttagga ggctgaggca ggaggattgc ttgagtctgg   11280
gaggtcaaag ctgcagtgag ccatgattgc accactgcac tctagcctgg gtgacagagt   11340
aagtaggact gacaaaaaaa aaaaaaaaa aaaaaaaag ccagaggtag gcagttcagg    11400
cctatcttga tggcttcttc atgacattat caggaactga agctttttct ctttatgggc   11460
tctgtcatcc ttagcacaac ttagtacaag ggtatcatcc tcaaaataac aagatagctg   11520
```

```
ctgtcactgc agccatcaca tccaagttcc aggctctgaa aaggagaata taaagaaaaa  11580
aatggcaaat ggtcataccc ctttaaaggg ctttaaatcc taccagaaat tctactcaat  11640
ggctatttac atttcgttgg ccagaactta gttgtgggt cataactatc ttagagaaag   11700
ctgggaaata cagtctttta gctgggatac cctgaataaa atcagaggtc tgtaattaag  11760
gaagaagggg gaaatgggtg cggtggcagg aatactcttt gccagtagat gcttcattaa  11820
cctggcagta atggagctac ttatcctgta cttctagaat aatcaggaag gcagttcttt  11880
tacttccttt attttttgctc cagaaactga caaattcacc ttatgggtgg gtggttcctc 11940
tattggcagc cagagaatac aatttttttc cccttaaggg aagactggtt attaatactc  12000
ttccatttga cctttatcaa gtggaaacag attaaatgta ttgatatttc cagttgccta  12060
tctcaaattt gtacgattaa gtatttatgg atgacgaatg gtcatgtgta ggaaatgtca  12120
accttttgtc ctgaggtcac caactgtggc cttgactcca aggaggccat atgatgtggt  12180
ggaaagaatc ttggatctta ggcttggctt tactgaattc cagaaccttg gcaatgttc   12240
tgtacctctc tgggccttgg ttttcccatg tgtaaaatga gggattattt tgaaatgtgt  12300
gttcctcaga gcctctgggt tctgcagggg actgcccagt gagtggaggc ctggtagatt  12360
gttctagaca ctgctttact taggtcagca ctgccttcaa ccaccatgtt caacctgaca  12420
tctaagaaga tggcatttgg ggagagagga gagctgctgc tttaaaaaag aagttcgaaa  12480
atcttgtgaa tagagaattt atagtctatt ttaaagatca gctgaatgga ccccatcatg  12540
cctggttacc ttctcacaga taaacaaata ctggaccagg gaaaggagct gggaaaaaa   12600
aaactctttg aattcaacga tacagtaatt gaaacatttt catcagtttc ccttctacct  12660
ccatttggat gatggatgaa cttttttaaat tacagattgc tagatgaaag tatagggtta  12720
tgatggagat acagttcttc ttcagtcggg ggtcttttcc agggcaaatg aaccagtatt  12780
ttgtgccatg aatcgtgctg cagatacttg catacatcat ctcattcaat ctttccaaca  12840
accttctcag gtacaaatgg tactagtcct gttttgcaaa ttggagtggc ctctctgtaa  12900
aggctcagaa ctaggtacta ggaataaaaa gaaattaaag accctcgagg ggctcaaagc  12960
ctggacaggg agataggctg ttaagcccat ttaaaacctg ggtgtgttga gtgctaggct  13020
ggagacatgc atacaagaag gctggtctgt gggggtagat aatgcctctg ttgactctta  13080
ggatgaatta gaggcacaag ggtgagagcc tggtgtgttc ggcaaacaat aatcagtgag  13140
gggttgacag cgagggagtg attggtaaga ggtgaatgtg gagggtggac cagagtcaga  13200
tgctaaaagg ccttttccac tgtgcccagg gatttgcact ttatttcaga gttgatggtg  13260
agtaattgaa gcctgtcaag caggagagtg gtgtactcct tcatgctttt aaaagtattc  13320
agtccatcac ttgaacccag gaggggagg ttgctgtgag ccaagactgc gccactgcac  13380
tccagcctgg gcaacagagt gagactctgt tcaaaaaaa aaaaaaaaaa agaaaagaaa   13440
agaaaaagta ttcagcccag ctgagcacag tggctcatgt ctgtaatccc agcactttga  13500
gaagccaaga cggtaggatc gcttgagccc agaagtttga gaacaccctg gtcaacatgg  13560
caaacctcca tctctttaaa aaatacaaaa tgttagcttg gcatggtggc ttatgcctgt  13620
agtcctaggt acttgggagg ctgagatgag aggatcactg gagcctagga ggttgaagct  13680
gcagtgagct ataattgcac cactgcactc cagcctggac aacacagtga aaccctatct  13740
caaaaaaaaa aaaaagaag aagaagaagt tcagcccagc aagaatgtag aggatggatt  13800
agagtgtcca agaggaggga ctgggaaggg acaaagagga ccccactaac gagggttgga  13860
```

```
gagggaggtt taattagaga gattttgagg aactaagatg agatgaaatc tgaggaagga    13920
gtaggagtta tggaggatgg tttccaagtt tgtggccggt aaatgtgatg cttttcacta    13980
agagtttgag ggaagacaca ttttgtcaaa tttgtggtgt tgatgggata ttcatatgcg    14040
ggcagagctt agaagaacaa tgtatggtct ctactggacc tttggaatgg ttttatgggc    14100
taggagcttt caccagagag tttaggaatg tcattagtgg ggtggtgata aatgtttaag    14160
aatcaatttt ctcttaaaag agaagaaaa agaaaaagca cggatttata gcatttgctg     14220
atttgggtgg tgtaaacact tccgtcaagg ttaattttga gctaccaatg tgctatttct    14280
aaaactcaaga gctggcaaaa gatgtgggca gctccagcat gtcactgaat aagaaatttc    14340
actttatctt caataactga gccccaggaa cactgttgtt aaccagcctc tatataggta    14400
gctttcacta accagcctcg gtgtaggtag ctttcactga tgctatttaa ggaccactga    14460
gtactccaca ttgtcctaac aggtttgaat gtggttttgt cccatagaat gttagcaaga    14520
attgtagcta tggctgggcg tggtggctca cacttgtaat ccaggcactt tgggaggcca    14580
aggagggagg atcacctgag gccaggagtt caagaccagc ctgggcaaca cagtgagact    14640
atgtttctac taaaaattaa aacatgaact ggtcatggca gtgcgggtct gtagtcccac    14700
cttctctgga ggctgaggcg ggagcatctt ttgaacccag gagtttgagc ttgcaatgag    14760
ctatgatcgt gccactgtac tccagcctgg gtgacacagc aagactctgt ctcaaaaaca    14820
aataaacaaa gaattataac tacaatgtag gaaatattga aatctgaaaa catgaccaat    14880
gtacttgaat tatgcgatct gttcctttaa atgccaaaat atttattcca ggagattcta    14940
gtgaaattga aatttatcag aataattcta atggagagga tcccctgatt tatgtaactc    15000
tttcacatgg ttttgcacaa tcaggatttt ttgtgagcta aaaatatatt aaatactcat    15060
tgtctttctg agtgataagc aagccaagat tcatgcata atcttctgct atgttatcct    15120
gaaacagaag gctcagttaa cctttttgtgg ccttaaactc tgacactttc ttcttttgaa    15180
ataactgcct tgtctaactt tttaagttttt ttttttttttt tggcttgttt ttttgtttgc    15240
ttgttagttt tttaaatcta gtttcaggtg ggttcagtgg ctcatgcctg caatcccagc    15300
actttgggag gccgaggcgg gcagatcatt ttaatccagg agtccgagac aagactgtac    15360
aacatggcaa aaccttatct ctacaaaaaa tacaaaaatt agttggatgt ggtgatgcat    15420
acccgtggtc cctgctactt gggaggctga ggtgggagga tcacttgagt ccaggaggtc    15480
aaggctgcag tgagctatga tcatgccact gtactccagc ctgggtgaca gagtgagact    15540
ttgtctccaa gaaaaaaaa attaagttcc atcaaaatca aagatttatt gtgcttgtta    15600
tataaccaca ttttctctca atatctttta caattctttg agatatatta ctgccacttt    15660
tattatcaaa ctagcagcct gctcactggc tttcctgttc tgaacattgg catgagtttt    15720
aaaactatga cacttgtctt gtcttgctgc actttatgtc ttcaagcaga ttttctagcc    15780
cttactgaat cattactcta agcagcacac atttttttagt tttattcttt tcaggtatt     15840
gactttccca tttcagaatg ggacttgagc caggcttcat tgatctttg tggatttgaa     15900
tgtggcagga cctcttggtg tcacttttta tctgtgcctt ccaaaaatat tttcattatg    15960
gaagtagtca aatcaagtcc aagtgcagtg aaaggtggat ttggtcagat ttccttgagg    16020
ctttggagtt ttgctttaaa tctagaaagt gttcgtggct tctgaattgg ttctgcactc    16080
tgactattgc ttggtccttt cttcgtcatc atcagagctc cataaaagag agcggggagg    16140
ggataacata aataatgctg aaatagccct gagggatgag acatggccca gcaactgaag    16200
ccttcgtctg cccgtggcca cagggcactt tatggttttg cttcttgtca ttcaaccacc    16260
```

```
tgccttgggg tgcttcactt tgcatttcca cgcagagttt cccgcattgc caaacttgat   16320
catgtgcctt atgtgtagca gttttgcatga ggtggaattt gcataaatta tgtgtgcatc   16380
acccaggagc atctgtagtt aaatacttta ttgattctaa attttgccca taatcttaat   16440
tttttaatta ttttatttc ttttcctctt ttagagattg gggtctctct ctattgccca   16500
ggttggagtg cagtggcaca gtcatggctc actgtcgtct tgagctcctg ggctcaagca   16560
gtacttccac ctcagcctcc cgagtagctg ggattacagg ctgaagccac cgagcctgcc   16620
tccgttatct taattattat tataattatt tttttgagtc agggtcgcac tctgtcaccc   16680
acattggagt gcagtgacac aatcacggct cactgcagcc tcagcctcct gggctcaagt   16740
gattctctca cctcaacctc ctgagtagct gggaccacag gttcaggcca ccatgcccaa   16800
ctgttttgtt tttgttttta tttgttttaa tttttgtgg agacgaggtc tcactatgtt   16860
gctcaggctg gtcttgaact cctaggctca agtgattctc ccacttcagc ctcccaaagt   16920
gctatgatta caggcatgag ccactgcacc tggtaatctt aatttttaaa ctgttctttc   16980
ttctcatcaa aaagacatt tattcaagtt agattatatt gtcttggttt agttttgctt   17040
ttgctctttc ttaattttta ttaatttcca gtgatgaaat tatttatata ttgtttaatt   17100
gtttctcctt tgatatcacc aggataggaa gaaaagaaag tttatacctg gttaattcgt   17160
cactgaaaac aattttctgt atccttttat atatagtaga ctacaagcta aatttttat    17220 catctaagtt aacatgtcta taactaaat tcattattac tagctatttt taataagtta   17280
ttgagatata attcatatgc cacaaaattc acccttttcc agtgtacaat tcactggctt   17340
ttagtatatt aagtgagttg tgcaactatc accagtattt aatttcagag cgttttttt    17400 atcatccccc agaaaactg ctcacttgta agctgtcatt ttccatttct tctcaatccc   17460
tgtggctgta cgcagccact gatctgcttt ctgtctctat ggattgactt attctagaca   17520
cttcatataa gtgaatcat acaacatgta gcatttcatg agctattttc acataccata   17580
atgttcttaa ggttcatcct tcattctttt ttatggctaa ataatattcc atgtgtgaat   17640
acgcacattt tgtttatcca catctgggaa ggttccactc ttggaactaa tatggataat   17700
gttgctgtga acaccatgca ggttttgca tgaatatacg ttgttatttc tcttggattt   17760
gctagctgat ttagcatgtt tactaacatg ccatttagt tgtaaccacc attctttcac   17820
acttgggaac tgattatccc tgactcagga tgcctcgtta agtgtattag tgctgttgct   17880
agttgggtta cttccttcat catccaattc tgacagctgc taatatttgc tgtacttctt   17940
tcaatagctt tctgatatac ccttttccat cacataaata atagaataat aattattctt   18000
attatttaaa aattaattt actcttctcc aattataaag taatacttgt tcattagaga   18060
gaatttggaa aatacaggaa aacatagaaa ctaaggaaaa aaaattataa tcccactacc   18120
cagaaacaac cactgttatt atcttgggga cttttttgtt tttgttttct gtccttttct   18180
gctatgtata ttttatgtag ttgaaacttg gttactatta tgatgtaaat attccccaca   18240 cccctgcca tttatttg agacagggt ttactctgtt gcccaggctg gaatgcaggg   18300
tgcaatcacg cctcactgca accttgaact cctgagctca agggagcctc ccaactcagt   18360
ctcctgagta gctgggacta caggcatgtg ccaccatgcc tagctagttt tcttttaac   18420 ttttgtagag acagggtctc cctctgttgc ccaggctggt gtcgaactcc tgggctcaag   18480
tgacccactt gtcttgcct tccaaaatgt tggcattaca ggtgtgagcc accacacctg   18540
gccaattttt ataaactctg taaatgctta tttacatata taagagtgtt ccttagagca   18600
```

```
gcagcattat ttgtgatgat gacaaattag gaaacaatat tcattagatg gtgagtggtt      18660
aagtaaatca tgtctgtctt gtggaattct gtggaacggc tgaaaatgaa tgaggtaaat      18720
ctatgtgtac tgacattaaa agattgccta gaaatattaa atgaatcaca cagtaataca      18780
ggtggtatga tcccatttta gcagaagaaa acaaaactga accatgcagg tgtgcacata      18840
catgtaaata agtggctaga aaagtatcta gagagaaaca catccacctc ctagtaatgt      18900
ctcacactgg gaaggggggct gattagaatt agggtgggta agaaaagtgg ttaagggcag     18960
ggaccgggag ggaagatttt gtcttttaca ttattttctg tgtttgattt ttttttttaat    19020 gatgggaatg tatttctgta ttaaatatgt aagttttaaa agtagaaaaa aacacttttt      19080
tttttttttt tttgggacgg agtctcgctc tgtcgcccag gctggagtgt agtggtgcta      19140
tctcggctca ctgcgagctc cacctcccag gttcatgcca ttctcctgcc tcagcctccc     19200
aagtagctgg gactacaggc acccgccacc acgcccggct aatttctttt tgtatttta      19260 gtagagatgg ggtttcactg tgttagccag gatggtctcc atctcctgac cttgtgatcc     19320
atctgcctcg gcctcccaaa gtgctgggat tacaggcgtg agccacctca cccggccgaa     19380
aacactttta atgtctgcat acttgccat gtttataaac cataaagtta tttatccagc      19440
acactaatta ggagtgttta gatggttttc agtccttac tgttttgaat ggtgctgcag       19500
ggaacatcag cttctttgca taaaaagcat tttctctatt ttagaatatg ttcttaagct     19560
ggactctcag gaatggaatt accagatcaa agggtataat gagcacattg gaggcttgga     19620
ctgtatttca ctaaattgct tcccaaaaga cttgtgttgt ttgcccctca ccagcagtat     19680
gtgaaaatgc tctttgccct atatccttt cactggtggg agacttcatt caaaaagata      19740
tttgtttgtt gaataatatt tgctgtggag atacactgta gttcctcatt gttgacttaa     19800
tgcatatttc tttgatggcc agggaagtgg aaggttttcc cggaagtatg tcatcccttg     19860
ctcctggtct tgcaaaattt gtctgttcag ttcaggggct ttgcctatct ggccatcaga     19920
gtcttactaa ttttctttgt tgatttgtaa aagttccttt taaagcgttc cttgtataga     19980
aaagatattt gactggtttt aaaacacatt tttgttttct tttgactttt aatttggctt     20040 atatatttt gcatatggaa gtacagcatt tgaaagtatt gtgctataag gctttcctta      20100
tatgtgctat gatttcctcc actgttttat gtgtaggaag tcctctcccc acttcagaga     20160
cttgataaat attcatttat atttcatct accaccaatc actttacaga catttgactg      20220
gtcaagcatt accctcctag cttttccccc cacactatct tacaaatata ttgtgatttg     20280
ttttagtttt tgtttttgt ttttgagaca gggtctcact ctgtcactca ggctggagtg      20340
cagtggcatg atcatggctc actgcagcct cgacctctca ggctcaggtg atcttcctac     20400
cttagcctcc tgagtgtcta ggactacagg caccactatg cctggctaat tttgtgtatt    20460
ttttgtagag atgggatttt gccatgttgc ccagactggt ctcgaacttc tgggctgaag     20520
cgatccttcc accttggtct cccaaagtac taggataaaa ggtgtgagcc accacaccca     20580
gccctacaaa tatatttga agatacgaat taagctcatt aaaaggatgc cagcatagaa      20640
ttttcagagt ggtcctttaa tccccaaatt ttgacagttg tattctgcac cttcatggag     20700
aatctaggtc ataactgatg ggcagcagga ggggcatgtt ctgctgcagg tcctccctct     20760
aaggctcctt cccagaggag aaaatggtct taaatatgcc ctaggtttgt tccacaccct     20820
aggtttgttt tacagggaac tgggtcatca catggttagc tcagcctcag ctatatcatt     20880
ttagcaggga tctgagattt gaaatcttaa gaacctccat ttatctttta tgagctcaaa    20940
acatttctgc cctccaaaag acttgaatag acatttctca aaagaagaca cacaaatggc     21000
```

```
aaacagacat atgaaaaggt gctcagcatc attgatcatc agagaaaggc aaatcaaaac    21060
tacaatgaga tatcatctca ccccagttaa aatggcttac atccaaaaga caggcaataa    21120
cgaatactgg tgaggatgtg gagaaaaggg aaccctcgtt cactgggcg ggaatgttaa     21180 ttagtataac cattgtggag aacagtttgg aggttcctca aaacactaaa aattgagcta    21240
ccatatgatc cagcaatccc actgctgggt acacacccaa agaaaggaa atcagtatat     21300 caaagagata cctggaccct tatgtttgtt gcagcactgt ttacaatagc taagatttga    21360
aagcaaccta agtgtgcacg aataaggaat ggataaagaa aatgtgatac aggccgggtg    21420
tggtggctca ctcctgtaat cccagtactt tgggaggcca aggctagcgg atcacttaag    21480
gtcaggagtt cgagaccagc ctggccaaca tggtgaaacc ctgtctctac tgaaaataca    21540
aaaattagct ggcatggtag tgcatgcctg aatcccagc tactcaggag gctgaggcag     21600
gagaattgct tgaatctggg aggcagaggt tgcagtgagc tgagatcaca ccactgcact    21660
ccaacttggg tgacagagtc acactctgtc tcaaaaaaaa aaagaaaaa agaaaatata    21720 gtacatatac acaatggagt actatttggc catgaaaaga atgagatcct gtcatttgca    21780
gcaacatgga tggaactgga gatcatgtta agtgaaacaa gccaggcaca gaaagacaaa    21840
catcacatgt tctcacttat ttgtggaatc taaaaatcaa aacaattgaa ctcatgaaca    21900
cagagagtag aaggatagtt tgcagaggct aggaagggta gtgtgagctg cagggaggt    21960 ggggatggtt aatgggtaca aaaaacagaa agaatgaata agacctacta tctgatagca    22020
ccacatggtg actatagtaa ataataactt aattgcacat ttaaaaataa cttaaacagt    22080
gtaattgggt tgtttgtaat tgaaaggata aatgcttggg ggagtggata ccccattctc    22140
catgatgtgc ttattgcata ctgcatgcct ggaccaaaat atgtaccca taatatata     22200 cacctactat gtgcccacga aaataaaat taataaaaga tttctgccct ggagttgagt     22260
acttttccac tgcttctgga aaagggccag tattgctgat gtactggcat gttgctttgt    22320 gtcttttag gggccacaga gggtggagga tggcttctgc ttttttgggg ggcagagagt     22380 agggatgac ctctgcattt tcagaacgat tttcatgagg aaaaactttc ttcctcctcc     22440
agcaagtaca gcagccccca ctgggagcca ccacactgtt tcgagattgg gggcttggga    22500
tttcttggca atggtgtaga ggatggtgaa ggtgagctgg cctcttcaag gtttgaagct    22560
caattattga ggctgaacca aagagttgaa gactggagct ctctcgaatg cctggtttgg    22620
agatgtctgg gattcgcttc tcctaatgat cttgcttctc tcgcgaaaac tgcagatttc    22680
ttcatcctcc ggttgaacgt tcttggggag ccgcggccga cgcgcctcgc actgatggcc    22740
accaggggga gccccgcgcg cttcctcctt ccccttgtgt tccagggcgc acttcaaaac    22800
gctgacgttc tccttcgtcc ctctggggc gcccgagggg ccctcgcaga agatgaggtg     22860
cctttccagc caggcttctc gcgtgcaggg cttgggaaca gtgcatcccc atcctaccaa    22920
gcagtcccct cctcttcatt tgcatcgcgt ccgtagtctt attttcagt gaactggaga     22980 acagaaaatt ttaaaataga ttttttctaat attccagaag gtcaaacacc tttctgcaaa    23040
gtatctagca tactaaaggg gaagtaattt tacatgtctg gaaggtacca tgtttgcatt    23100
agaaaggagc tcttctattg tactaaagtc tccaacaaac ctcttgaact cttaagcctg    23160
aattgaaaat gtgtcaatgt tttcagaaaa tctgaggcct agaagctaga gcctcagttc    23220
cctcccctgc catttgtaga agccttatag gggatatctg gggttttga agaaaaacac     23280 tttctaagta ggctatttg ctttgcttgt tcatacaaaa gacaggggtt ctgaaagtga    23340
```

-continued

```
gggatgccat tgtgagggaa gctattcaac attaagaatg gccaatatct tttttttttt   23400
tttttgtctt ttgagagggg gtcttgctgt gtttgttgcc caggctggag ggcagtgatg   23460
tgatcatagc tcactacagc ctcgaactcc tgggcaccac tacacccagc taactttttt   23520 tatttttttgt agacacggtc tcactatgtg ctctaggctg gtctcgaact cctggcctca   23580
agagatcctt ccactttgac cttccaaagc actgggatta caggcgtaag gcacagtgtc   23640
tgaccaccaa tatctttttt tttttttttga gacaggatct cactctgtca cctaggctgg   23700
agtgcagtgg cgtgatcact gctcacttca gcctctacct cccaggctca ggtggtcctc   23760
ccacctcagc ctcccaagta gctgggactg caggcacaga ccacaatgcc cagttagttt   23820
ttttgtagag acagggtttt gctatgttgc ccacgctagt ctcgaactcc tgggctcaag   23880
cagtctgtcc acctcagcct cccaaagtgc tgggattaca ggcatgagcc accatgcctg   23940
gctgtatctt tatatgtgat atataatcag gtggaagaac tcaacataga attctttaaa   24000
aggatggatt ggatattaac ataactactg ctaagtggat ctagatctaa cacccatttt   24060
tcattccatt tctgatgata aaacacttaa gaaagacaag acattggatg ttaagtctgt   24120
cagtttattt tgcctctgcc tctatcctaa aattttttca gaggggtaaa tgcaagggac   24180
ttgttttaaa ttgagtacaa gaaagaacta ttttagtaaa gttgcctgaa gatctgctca   24240
tcagtggaat aaaacaggaa ggacagaatt ctgataagct cttttcataat gactatgttg   24300 gaatgtctca tccctctgtc agttgctttg gcttgagctt ctgattcaga gagcatgaaa   24360
aggtgagact aaggaggaaa ttcttttcac agagaagctc agagccgaac caatccttgg   24420
ctgtagagaa ggaggagctt tcagagtttg ctggttccaa gcttttttct gttacttaaa   24480
tttaaagctg gaacagaagg tcaagaaaca ggaaggaaaa ccgtatcaag atatcaagtc   24540
atggtattct ttttcattct tacagaaaag aattcacaag agacttgagg aagcttttttt   24600 atttttattt tgttctgttt atttatttat tttaagatgg ggtctcaccc tgttgcccag   24660
gttggtctca aacttctggg ctcaagtgat ctgcccactt cggcctccca aattgctgtg   24720
attacaggca tgagccactg cgcctggcca atttttttttt ttttttttttt tttgcgacaa   24780 ggtctttctc tagagtgcag tggcatgttc acagcttagt gcagccttga cctcccagcc   24840
tcaagtgatc cttccacctc agcctcctta gtagctagga ctacaggcat cactaggact   24900
acaggtgcca ccaccacgtc cagctaattt tcgtattgtt tgtagagacg gggtttcacc   24960
gtgtttctca ggctggtctc aaactccttg gctcaagcaa tttaaggaag ctttttcatta   25020 gagtctaaaa atacatattt gaattgaatg acacagggtt gacactagtc agagaattag   25080
gaaaatgtga tatgcgtgtt agttccagtg caaaccggag agcccgttaa cctccctggg   25140
actgggtttc ctcctctgca cagcaaggct ccctgtcct tccccatggg agacaagaat   25200
cacatcacca gcatgttttc ctctcccctt tggctgccag gaaactcaag agtcaaattc   25260
aaggctttat tgaaggaact ctgcaggacc caggacgtga tatcttgata ctgttttcct   25320
tcctggtttt tgaccttctg ttccaacttg cgttttccct gattatagca ttttattatt   25380 tttcatatttt agtatgtagt gcacatttttt acactacact tctaatcctt tgtgtaatga   25440
tcatggtaga aataaatggt gaaatgagga ggtcccactt agatgagttt caggggtcct   25500
tccagtccca atttccagg attcttaagg ggaaaaagta attttacatg tctggaaggt   25560 tccaggttg cacagaaggg aactctccta tcgagagtcc tgaggacttc agcagacctc   25620
cagggaggcc tgtccaggat gttctcctac gtctgtaaag gagtgagcac tttgtgctag   25680
tttagggaaa gacagctttt ctgttgggat tttagactta ccctgcttga aattggtgga   25740
```

```
aaaatacctg tctgggatgg ggctcaataa tctgcagctg tattaggaaa tgcaagtagt   25800
tttgatgtgg gtggtttcaa gacatatttg gaaaatgtga gggaaatgtg tatgtgcatt   25860
tgctgagcgg gggactggtg aaggatcacc gatccattta ttcctaatgc tcatctcagc   25920
tttttattgt gccgagtacc ttgataaggc ttgggttatt ttatgagcgt ttatatataa   25980
attgatagtg tccatcagat catgtatatt tagaggcatg ctcctacttt gagtaaatgg   26040
aaagctttag agatatacac taaataaaca tcagttacta attaaaaatt ccctcctcac   26100
tttaccaaag gacccaccat gggttccatt aaatgtctat ttatggtttg ttttgacaaa   26160
gacttttcca agaacacctc tgttctgtaa agcagaagag ctgtgtagat gttccagagt   26220
cgcttggtgt aaatttggtt ctgatttgtg ccgtgaagcc caataacaaa ctggaggcac   26280
acatttcaaa gccagtggta agagtttgag tagtgatcat ctattcctga acataaagtc   26340
tggagccttc tggaatccat aaaaatggaa tgatttgttc ctttcccctc taaccaaatt   26400
ttattcatac ctggctataa atagcttctg ttttgagttt tcactggtca gaccctgctg   26460
ttttagtgcc atcctgttag cttccttgaa caaggtaatg ccacctaaca tgttttttca   26520
gacttccagg acaatgatca gggggacttc tctatgccac actgggaggt gtgaaggtgt   26580
aggctttagg gcaaccccte tgagaagggg tggcaggtgg aggagcccat tgatcctttc   26640
tatcagggat ggatttgctt tctgtgggtg tcaccttcag gggcctgtgt tcccactcat   26700
cacaggagct catatttact cagtggggcc agagtgttct tcatacatgg tgattttact   26760
cctcaccata acctccgtgg tgcgtgctaa catgaccacc attttgcaga tgagaacatg   26820
gaggcttgca ggggaggtaa gttgccccag gttccatgct gaatcagagg tcaagctcag   26880
cacacagcac aggaccaagt ctgctggttc ccaagctcac atccttacct acaactctga   26940
atcaccccac agcagagtca acaagctggc ctggcatgtg aagaagcaag cctgggtgtc   27000
tcctggctgc cagtgccatc cctgccccgg gaccctaatc cacagtttga ttctggtcct   27060
tttgccctct gtccctcacc agaaccctga tatttccaga tgaaaacacg agtatagctt   27120
atttccacaa ctcacctggg cccagcaatc aagatctata gctataggga agtattgagt   27180
tgattatgag ttatataggt caaaatgagt agcttgcttg attgaagcag gtaattcgtg   27240
ccatactttt ctctttggga agacctgtac caacaataac ctctgctaaa cactttcgct   27300
tttttaaatt tgcaggtact ttttttgggg c tgtctttggc tgcctgtctg ttgagagttt   27360
gttttcttta cagtccatct gatttacagt ccctccgggt tgatttgtct catttgggaa   27420
tgagaaattt tattttaatg cattaagtaa tagtgttgag tggccaacaa atgtgaagtt   27480
tgaaaagctc aaatgaaaaa aaagtgtga tagaaacaca gagttggggg ccgggtgcag   27540
tggctcacac ctgtatttcc ggcactgtgg gaggccaaga caggaggatc ccttgagctc   27600
aggagtttga ccccctgggg caacatggca agacccaag accccatctc tacaaaaaaa   27660
atgtaaaaat cagccagggg taatcccagc tacttgggag gctgaggtgg aaggattgct   27720
tgagcccggg aggttgaggc tgcagtgagc tgtgatcgat ctactggact ccagcctgag   27780
tgacagagca agaccctatc taaaaaaaaa aaaaaaaaa aaaaagaag aagaagaaca   27840 caggttggaa tttgaggggg cctgttaaat aggatgctct ttcctgcctt agttttgaat   27900
taattgagaa gataaaataa taaggcatgg agattagagc atcccctttc ttttttttctt   27960 ttctttttct tttttctttt tttctttttt acttttttgct cttcttggcc aggctggagt   28020
gcaatggcac aatcttggct caccacaacc tccgcctcgc gggttcaagc aattctcttg   28080
```

```
cctcagcttc cccagtagct ggggttacag ccacgtgcca tgatgcccag ctaattttgt   28140
attttcagta gagacggggt ttctccatgt tggtcaggct ggtctcgaac tccccacctc   28200
aggtaatcca cccgcctcgg cctcccaaag tgctgggaat acaggcatga gccaccaggc   28260
ccggcagcat cccctttctt attgataaag cagatcttgg agaatgggag atcctgagcg   28320
gggttcctaa tgctagcctt caacatcagg ctgaggctca ccttgtcttc aagtaatggg   28380
cagtgctggc ctgaagggga gcctcctctg tccagggctc agcttatcct tggaaggctt   28440
agcacattga ggagctgctc caggctaaga gggagggact ggggtactct gtagaggttg   28500
ttcttccagt ttcttcaatc agatgagcca cactgtcact ctagtgttga aaggagggaa   28560
gggacagagg tggccaggag tgtgacccta aaagaggcag aggagacctc agagaaagag   28620
aagaagcatt ctcctaacca gagggagaag gagagaggcc tcagttctcc ctctctggga   28680
attaatttga gatttacatt tagtgtctat aaacatgtca gcagatatat aaacttattt   28740
gcttttgctt tgtttccatt tttagattct tgagtatcag aacaccacct tctttggtgg   28800
aacctgtata tccatgattg attacctcct ctggccctgg tttgagcggc tggatgtgta   28860
tgggatactg gagtaagaca tttgacattg tggtgttaaa ttcccggagt cacactgagt   28920
aacaatggtt aagatggtct gcatgccccc tgtagacatg tttcaggatg tctgtgaagt   28980
gaatcaggtt tctaaaccgc agtgtgtgct tccttgttaa aaacatatgt gcttttccac   29040
tgctaacttc agacccacac tttgcccgca tttctgcaga tcagacccct agcccaggag   29100
cctcccgcag acttcagagc ctgctgtcct caccagcgcc cccacatggc cggtctgaga   29160
gcaagtggag agtcacagtc acagtcacag tgcccaacgc ctccacctgg tcctgacggg   29220
tccccagggg acaccatata accttagtca tgtctcattg cccggaggaa tcttccccca   29280
gataggaata accttataaa aaagatttgt gtagtaatat atgcttgata ttggaacata   29340
caaacaaaat ggcagtgaca cactatggaa gtatggaagt gcagggacat taaaggagaa   29400
gaaatagctg tgtaggctcc tgggcagagc agtgctgtgt tacttcaaag ctcagtgaag   29460
ctggacgtgt gcggacgtcc accctaatcc aagccaccct catggtgggt gctggacatt   29520
tctggcactt ggaaatccgg ccctgctgaa gcagaactgt gtctgcacct tcataacccg   29580
tgggctggag cccaaccagc cactgtctcc tgcacttccg acttcagctc tctttgtcag   29640
gatatttaaa actcaatatc aaacataaaa tttacaaaag gctgtatcct ctgaagacag   29700
agcatggagt cacaggttag gaaacctcac ttctagtcct ggattcccga caacccattc   29760
atattatctt cagcttattg ctttataaac cccagaacta aatatcctgg ttgagctttg   29820
aaagagccct gtcggctcca tgacttcaag gtttcatcct tgttttattc atttaaaaaa   29880
tgttttagaa attatttgtc tttatttttt tatatctcct aaagtaaaat ctgagaatga   29940
cccaagaata tttgtttcag agggttgtct ttttgttggc aagcagtgaa gcacatgtaa   30000
gtttctcaag ctttagaata tatatatatt aaaaaacaaa acaaaaaaaa tgaagcacag   30060
acatgttatt tcccagagc catcagtcca agtatttca ctgtattatt agaagcaaca   30120
acttctaaac attcaactat tccaaaaata agatttccct ccagtaagtt atcattctca   30180
cttgataata agataactaa gataacttcc caaataaact cattcttcat atcttgcaaa   30240
tctaaaaagc aacgtgcatc cccttttcctg atgcctaccc ctgcactgtg ctgacgcttc   30300
tttcctgtct tgcagctgtg tgagccacac gccagccctg cggctctgga tatcagccat   30360
gaagtgggac cccacagtct gtgctcttct catggataag agcatttttcc agggcttctt   30420 gaatctctat tttcagaaca accctaatgc ctttgacttt gggctgtgct gagtctcact   30480
```

```
gtccacccct tcgctgtcca gaattcccca gcttgttggg agtctacgtc acggcttgtc    30540
ttgggaacca atccgtctct ctttcttttc tttgaagttc ccaataaaat gaaaacagga    30600
aatgtattct tctgataatc atttgtctga ctcctctag                            30639
```

<210> SEQ ID NO 2
<211> LENGTH: 11
<212> TYPE: PRT
<213> ORGANISM: Homo sapien
<400> SEQUENCE: 2

```
Met Ser Gly Asp Ala Thr Arg Thr Leu Gly Lys
 1               5                  10
```

<210> SEQ ID NO 3
<211> LENGTH: 37
<212> TYPE: PRT
<213> ORGANISM: Homo sapien
<400> SEQUENCE: 3

```
Gly Ser Gln Pro Pro Gly Pro Val Pro Glu Gly Leu Ile Arg Ile Tyr
 1               5                  10                  15

Ser Met Arg Phe Cys Pro Tyr Ser His Arg Thr Arg Leu Val Leu Lys
                20                  25                  30

Ala Lys Asp Ile Arg
        35
```

<210> SEQ ID NO 4
<211> LENGTH: 74
<212> TYPE: PRT
<213> ORGANISM: Homo sapien
<400> SEQUENCE: 4

```
His Glu Val Val Asn Ile Asn Leu Arg Asn Lys Pro Glu Trp Tyr Tyr
 1               5                  10                  15

Thr Lys His Pro Phe Gly His Ile Pro Val Leu Glu Thr Ser Gln Cys
                20                  25                  30

Gln Leu Ile Tyr Glu Ser Val Ile Ala Cys Glu Tyr Leu Asp Asp Ala
        35                  40                  45

Tyr Pro Gly Arg Lys Leu Phe Pro Tyr Asp Pro Tyr Glu Arg Ala Arg
    50                  55                  60

Gln Lys Met Leu Leu Glu Leu Phe Cys Lys
65                  70
```

<210> SEQ ID NO 5
<211> LENGTH: 34
<212> TYPE: PRT
<213> ORGANISM: Homo sapien
<400> SEQUENCE: 5

```
Val Pro His Leu Thr Lys Glu Cys Leu Val Ala Leu Arg Cys Gly Arg
 1               5                  10                  15

Glu Cys Thr Asn Leu Lys Ala Ala Leu Arg Gln Glu Phe Ser Asn Leu
                20                  25                  30

Glu Glu
```

<210> SEQ ID NO 6
<211> LENGTH: 36
<212> TYPE: PRT
<213> ORGANISM: Homo sapien

<400> SEQUENCE: 6

Ile Leu Glu Tyr Gln Asn Thr Thr Phe Phe Gly Gly Thr Cys Ile Ser
1               5                   10                  15

Met Ile Asp Tyr Leu Leu Trp Pro Trp Phe Glu Arg Leu Asp Val Tyr
            20                  25                  30

Gly Ile Leu Asp
        35

<210> SEQ ID NO 7
<211> LENGTH: 51
<212> TYPE: PRT
<213> ORGANISM: Homo sapien

<400> SEQUENCE: 7

Cys Val Ser His Thr Pro Ala Leu Arg Leu Trp Ile Ser Ala Met Lys
1               5                   10                  15

Trp Asp Pro Thr Val Cys Ala Leu Leu Met Asp Lys Ser Ile Phe Gln
            20                  25                  30

Gly Phe Leu Asn Leu Tyr Phe Gln Asn Asn Pro Asn Ala Phe Asp Phe
        35                  40                  45

Gly Leu Cys
    50

<210> SEQ ID NO 8
<211> LENGTH: 732
<212> TYPE: DNA
<213> ORGANISM: Homo sapien

<400> SEQUENCE: 8

```
atgtctgggg atgcgaccag gaccctgggg aaaggaagcc agccccagg gccagtcccg      60
gagggctga tccgcatcta cagcatgagg ttctgcccct attctcacag gacccgcctc     120
gtcctcaagg ccaaagacat cagacatgaa gtggtcaaca ttaacctgag aaacaagcct     180
gaatggtact atacaaagca cccttttggc cacattcctg tcctggagac cagccaatgt     240
caactgatct atgaatctgt tattgcttgt gagtacctgg atgatgctta tccaggaagg     300
aagctgtttc catatgaccc ttatgaacga gctcgccaaa agatgttatt ggagctattt     360
tgtaaggtcc cacatttgac caaggagtgc ctggtagcgt tgagatgtgg gagagaatgc     420
actaatctga aggcagccct gcgtcaggaa ttcagcaacc tggaagagat tcttgagtat     480
cagaacacca ccttctttgg tggaacctgt atatccatga ttgattacct cctctggccc     540
tggtttgagc ggctggatgt gtatgggata ctggactgtg tgagccacac gccagccctg     600
cggctctgga tatcagccat gaagtgggac cccacagtct gtgctcttct catggataag     660
agcattttcc agggcttctt gaatctctat tttcagaaca accctaatgc ctttgacttt     720
gggctgtgct ga                                                         732
```

<210> SEQ ID NO 9
<211> LENGTH: 243
<212> TYPE: PRT
<213> ORGANISM: Homo sapien

<400> SEQUENCE: 9

Met Ser Gly Asp Ala Thr Arg Thr Leu Gly Lys Gly Ser Gln Pro Pro
1               5                   10                  15

Gly Pro Val Pro Glu Gly Leu Ile Arg Ile Tyr Ser Met Arg Phe Cys
            20                  25                  30

-continued

Pro Tyr Ser His Arg Thr Arg Leu Val Leu Lys Ala Lys Asp Ile Arg
         35                  40                  45

His Glu Val Val Asn Ile Asn Leu Arg Asn Lys Pro Glu Trp Tyr Tyr
 50                  55                  60

Thr Lys His Pro Phe Gly His Ile Pro Val Leu Glu Thr Ser Gln Cys
 65                  70                  75                  80

Gln Leu Ile Tyr Glu Ser Val Ile Ala Cys Glu Tyr Leu Asp Asp Ala
                 85                  90                  95

Tyr Pro Gly Arg Lys Leu Phe Pro Tyr Asp Pro Tyr Glu Arg Ala Arg
            100                 105                 110

Gln Lys Met Leu Leu Glu Leu Phe Cys Lys Val Pro His Leu Thr Lys
        115                 120                 125

Glu Cys Leu Val Ala Leu Arg Cys Gly Arg Glu Cys Thr Asn Leu Lys
130                 135                 140

Ala Ala Leu Arg Gln Glu Phe Ser Asn Leu Glu Glu Ile Leu Glu Tyr
145                 150                 155                 160

Gln Asn Thr Thr Phe Phe Gly Gly Thr Cys Ile Ser Met Ile Asp Tyr
                165                 170                 175

Leu Leu Trp Pro Trp Phe Glu Arg Leu Asp Val Tyr Gly Ile Leu Asp
            180                 185                 190

Cys Val Ser His Thr Pro Ala Leu Arg Leu Trp Ile Ser Ala Met Lys
        195                 200                 205

Trp Asp Pro Thr Val Cys Ala Leu Leu Met Asp Lys Ser Ile Phe Gln
210                 215                 220

Gly Phe Leu Asn Leu Tyr Phe Gln Asn Asn Pro Asn Ala Phe Asp Phe
225                 230                 235                 240

Gly Leu Cys

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tgtaaaacga cggccagt                                                      18

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
caggaaacag ctatgacc                                                      18

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
tgtaaaacga cggccagtgg gcaggagtca gcaataaa                                38

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
caggaaacag ctatgaccgg tcttcagggc aacaata        38

<210> SEQ ID NO 14
<211> LENGTH: 40
<212> TYPE: DNA
<213> ORGANISM: Artificial Sequence
<220> FEATURE:
<223> OTHER INFORMATION: Primer

<400> SEQUENCE: 14
tgtaaaacga cggccagttg ctctcttgtt gcttgtcttc        40

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
caggaaacag ctatgaccag cctgctgaat cggaaat        37

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
tgtaaaacga cggccagttt cgccattgag agaaacct        38

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
caggaaacag ctatgaccct caaacccctc ttcccttc        38

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
tgtaaaacga cggccagtta gttggcgggt aggatcac        38

<210> SEQ ID NO 19
<211> LENGTH: 38
<212> TYPE: DNA
<213> ORGANISM: Artificial Sequence
<220> FEATURE:
<223> OTHER INFORMATION: Primer

```
<400> SEQUENCE: 19
caggaaacag ctatgaccgt ggtttgcgaa ggtttcat                              38

<210> SEQ ID NO 20
<211> LENGTH: 41
<212> TYPE: DNA
<213> ORGANISM: Artificial Sequence
<220> FEATURE:
<223> OTHER INFORMATION: Primer

<400> SEQUENCE: 20
tgtaaaacga cggccagttc tttggtggca ttattttcct a                          41

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
caggaaacag ctatgaccaa ccttttttgga tttcactttc c                         41

<210> SEQ ID NO 22
<211> LENGTH: 38
<212> TYPE: DNA
<213> ORGANISM: Artificial Sequence
<220> FEATURE:
<223> OTHER INFORMATION: Primer

<400> SEQUENCE: 22
tgtaaaacga cggccagtag ccgggaacca atatgtct                              38

<210> SEQ ID NO 23
<211> LENGTH: 38
<212> TYPE: DNA
<213> ORGANISM: Artificial Sequence
<220> FEATURE:
<223> OTHER INFORMATION: Primer

<400> SEQUENCE: 23
caggaaacag ctatgacccg taatggctgc tcaacaaa                              38

<210> SEQ ID NO 24
<211> LENGTH: 41
<212> TYPE: DNA
<213> ORGANISM: Artificial Sequence
<220> FEATURE:
<223> OTHER INFORMATION: Primer

<400> SEQUENCE: 24
tgtaaaacga cggccagtgc tgtacttact taccaaagag t                          41

<210> SEQ ID NO 25
<211> LENGTH: 41
<212> TYPE: DNA
<213> ORGANISM: Artificial Sequence
<220> FEATURE:
<223> OTHER INFORMATION: Primer

<400> SEQUENCE: 25
caggaaacag ctatgaccga ccccatggag agcactcacc t                          41

<210> SEQ ID NO 26
<211> LENGTH: 42
```

```
<212> TYPE: DNA
<213> ORGANISM: Artificial Sequence
<220> FEATURE:
<223> OTHER INFORMATION: Primer

<400> SEQUENCE: 26
tgtaaaacga cggccagtga gctccgggag ctgcgcaaac ca                    42

<210> SEQ ID NO 27
<211> LENGTH: 45
<212> TYPE: DNA
<213> ORGANISM: Artificial Sequence
<220> FEATURE:
<223> OTHER INFORMATION: Primer

<400> SEQUENCE: 27
caggaaacag ctatgaccgg gctcctgtga ggcgctgggt ttgct                 45

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
tgtaaaacga cggccagtct gattgcttct gctttcaaga aga                   43

<210> SEQ ID NO 29
<211> LENGTH: 42
<212> TYPE: DNA
<213> ORGANISM: Artificial Sequence
<220> FEATURE:
<223> OTHER INFORMATION: Primer

<400> SEQUENCE: 29
caggaaacag ctatgaccca tgctagctaa tctcctgagg at                    42

<210> SEQ ID NO 30
<211> LENGTH: 44
<212> TYPE: DNA
<213> ORGANISM: Artificial Sequence
<220> FEATURE:
<223> OTHER INFORMATION: Primer

<400> SEQUENCE: 30
tgtaaaacga cggccagtgc tggagttata aagcttcgct gcct                  44

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
tgtaaaacga cggccagtga aaggaagcaa ttcatggcat gt                    42

<210> SEQ ID NO 32
<211> LENGTH: 43
<212> TYPE: DNA
<213> ORGANISM: Artificial Sequence
<220> FEATURE:
<223> OTHER INFORMATION: Primer

<400> SEQUENCE: 32
```
caggaaacag ctatgaccga gaagaagcat tctcctaacc aga       43

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
tgtaaaacga cggccagtct gattcacttc acagacatcc tga       43

<210> SEQ ID NO 34
<211> LENGTH: 44
<212> TYPE: DNA
<213> ORGANISM: Artificial Sequence
<220> FEATURE:
<223> OTHER INFORMATION: Primer

<400> SEQUENCE: 34
caggaaacag ctatgaccct cattcttcat atcttgcaaa tcta      44

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
caggaaacag ctatgaccca agctggggaa ttctggacag cga       43

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
tgtaaaacga cggccagttt tcctgtcttg cagctgtg             38

<210> SEQ ID NO 37
<211> LENGTH: 38
<212> TYPE: DNA
<213> ORGANISM: Artificial Sequence
<220> FEATURE:
<223> OTHER INFORMATION: Primer

<400> SEQUENCE: 37
caggaaacag ctatgacctc ccaaaatgtg ctctgaca             38

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
tgtaaaacga cggccagtcc tgcctagcct gtagcttct            39

<210> SEQ ID NO 39
<211> LENGTH: 39
<212> TYPE: DNA
<213> ORGANISM: Artificial Sequence

```
<220> FEATURE:
<223> OTHER INFORMATION: Primer

<400> SEQUENCE: 39
caggaaacag ctatgacctc aactttatcc ccagtgtgc                              39

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
aggacccgcc tcatcctcaa g                                                 21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
cttgaggatg aggcgggtcc t                                                 21

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
accaaggagt acctggtagc gttg                                              24

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
caacgctacc aggtactcct tggt                                              24

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
gaatgcacta atctgaaggc a                                                 21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
tgccttcaga ttagtgcatt c                                                 21
```

```
<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
gaagagatta ttgagtatca g                                              21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ctgatactca ataatctctt c                                              21
```